United States Patent
Schwartz

(10) Patent No.: US 9,814,581 B2
(45) Date of Patent: Nov. 14, 2017

(54) MOBILE PROSTHESIS FOR INTERPOSITIONAL LOCATION BETWEEN BONE JOINT ARTICULAR SURFACES AND METHOD OF USE

(71) Applicant: Marvin Schwartz, Toronto (CA)

(72) Inventor: Marvin Schwartz, Toronto (CA)

( * ) Notice: Subject to any disclaimer, the term of this patent is extended or adjusted under 35 U.S.C. 154(b) by 237 days.

(21) Appl. No.: 14/722,837

(22) Filed: May 27, 2015

(65) Prior Publication Data
US 2015/0320563 A1    Nov. 12, 2015

Related U.S. Application Data

(63) Continuation-in-part of application No. 13/939,653, filed on Jul. 11, 2013, now abandoned, which is a
(Continued)

(51) Int. Cl.
*A61F 2/30*  (2006.01)
*A61F 2/00*  (2006.01)
(Continued)

(52) U.S. Cl.
CPC ........ *A61F 2/30756* (2013.01); *A61B 17/562* (2013.01); *A61F 2/0077* (2013.01); *A61F 2/3099* (2013.01); *A61F 2/30907* (2013.01); *A61B 17/82* (2013.01); *A61B 17/842* (2013.01); *A61B 17/86* (2013.01); *A61F 2/30942* (2013.01); *A61F 2/32* (2013.01); *A61F 2/38* (2013.01); *A61F 2/40* (2013.01); *A61F 2/42* (2013.01); *A61F 2002/30069* (2013.01); *A61F 2002/30495* (2013.01); *A61F 2002/30578* (2013.01); *A61F 2002/30754* (2013.01);
(Continued)

(58) Field of Classification Search
CPC ....................................................... A61F 2/30
See application file for complete search history.

(56) References Cited

U.S. PATENT DOCUMENTS 3,053,251 A   9/1962  Black et al.
3,178,728 A   4/1965  Christensen
(Continued)

FOREIGN PATENT DOCUMENTS

FR      1061009     4/1954
WO    WO02054992   7/2002
(Continued)

*Primary Examiner* — Matthew Schall
(74) *Attorney, Agent, or Firm* — Riches, McKenzie & Herbert LLP

(57) ABSTRACT

A biocompatible prosthetic device comprising a thin low friction spacer for location to overlie a bone member in an interpositional location between opposed bone joint articular surfaces. The prosthesis is preferably a thin spacer with at least one low friction surface, the spacer being adapted for location about a bone member in an interpositional location between opposed bone joint articular surfaces preferably about a margin of articular cartilage of a bone member's condyle, preferably without any modification of the articular surface of the condyle. One preferred use of a prosthesis is in a human temporomandibular joint as a thin cap-like member fitted closely over the mandibular condyle to be disposed intermediate of the mandibular condyle and the mandibular fossa of the temporomandibular joint.

6 Claims, 61 Drawing Sheets

Related U.S. Application Data continuation of application No. 13/352,399, filed on Jan. 18, 2012, now Pat. No. 8,506,637, and a continuation-in-part of application No. 12/591,845, filed on Dec. 2, 2009, now abandoned, which is a continuation of application No. 11/710,614, filed on Feb. 26, 2007, now Pat. No. 7,670,381.

(60) Provisional application No. 61/435,017, filed on Jan. 21, 2011.

(51) Int. Cl.
    *A61B 17/56*     (2006.01)
    *A61F 2/32*     (2006.01)
    *A61F 2/38*     (2006.01)
    *A61F 2/40*     (2006.01)
    *A61F 2/42*     (2006.01)
    *A61B 17/82*     (2006.01)
    *A61B 17/84*     (2006.01)
    *A61B 17/86*     (2006.01)

(52) U.S. Cl.
    CPC ............... *A61F 2002/30757* (2013.01); *A61F 2002/30919* (2013.01); *A61F 2002/30934* (2013.01); *A61F 2002/30957* (2013.01); *A61F 2310/00023* (2013.01); *A61F 2310/00089* (2013.01); *A61F 2310/00131* (2013.01); *A61F 2310/00365* (2013.01)

(56) References Cited

U.S. PATENT DOCUMENTS

| | | |
|---|---|---|
| 3,579,643 A | 5/1971 | Morgan |
| 4,224,699 A | 9/1980 | Weber |
| 4,385,404 A | 5/1983 | Sully et al. |
| 4,502,161 A | 3/1985 | Wall |
| 4,627,853 A | 12/1986 | Campbell et al. |
| 4,778,472 A | 10/1988 | Homsy et al. |
| 4,911,720 A | 3/1990 | Collier |
| 4,917,701 A | 4/1990 | Morgan |
| 5,108,441 A | 4/1992 | McDowell |
| 5,123,927 A | 6/1992 | Duncan et al. |
| 5,171,322 A | 12/1992 | Kenny |
| 5,358,525 A | 10/1994 | Fox et al. |
| 5,401,234 A | 3/1995 | Libin |
| 5,445,650 A | 8/1995 | Nealis |
| 5,489,305 A | 2/1996 | Morgan |
| 5,549,680 A | 8/1996 | Gordon |
| 5,624,463 A | 4/1997 | Stone et al. |
| 5,769,891 A | 6/1998 | Clayton |
| 5,919,232 A | 7/1999 | Chaffingeon et al. |
| 6,056,777 A | 5/2000 | McDowell |
| 6,171,340 B1 | 1/2001 | McDowell |
| 6,206,927 B1 | 3/2001 | Fell et al. |
| 6,352,558 B1 | 3/2002 | Spector |
| 6,558,421 B1 | 5/2003 | Fell et al. |
| 6,629,997 B2 | 10/2003 | Mansmann |
| 6,648,920 B2 | 11/2003 | Ferree |
| 6,652,587 B2 | 11/2003 | Felt et al. |
| 6,827,742 B2 | 12/2004 | Hayes, Jr. |
| 6,994,730 B2 | 2/2006 | Posner |
| 7,141,072 B2 | 11/2006 | Geistlich et al. |
| 7,148,209 B2 | 12/2006 | Hoemann et al. |
| 2003/0023313 A1 | 1/2003 | Byers |
| 2003/0060885 A1 | 3/2003 | Fell et al. |
| 2004/0030402 A1 | 2/2004 | Armin et al. |
| 2004/0204760 A1 | 10/2004 | Fitz et al. |
| 2005/0267584 A1 | 12/2005 | Burdulis, Jr. |
| 2006/0041262 A1 | 2/2006 | Calvert et al. |
| 2006/0085079 A1 | 4/2006 | Carroll |
| 2006/0149389 A1 | 7/2006 | Romagnoli |
| 2007/0026053 A1 | 2/2007 | Pedrozo et al. |
| 2007/0067032 A1 | 3/2007 | Felt et al. |
| 2007/0100462 A1 | 5/2007 | Lang et al. |

FOREIGN PATENT DOCUMENTS

| | | |
|---|---|---|
| WO | WO2004032987 | 4/2004 |
| WO | WO2006133711 | 12/2006 |

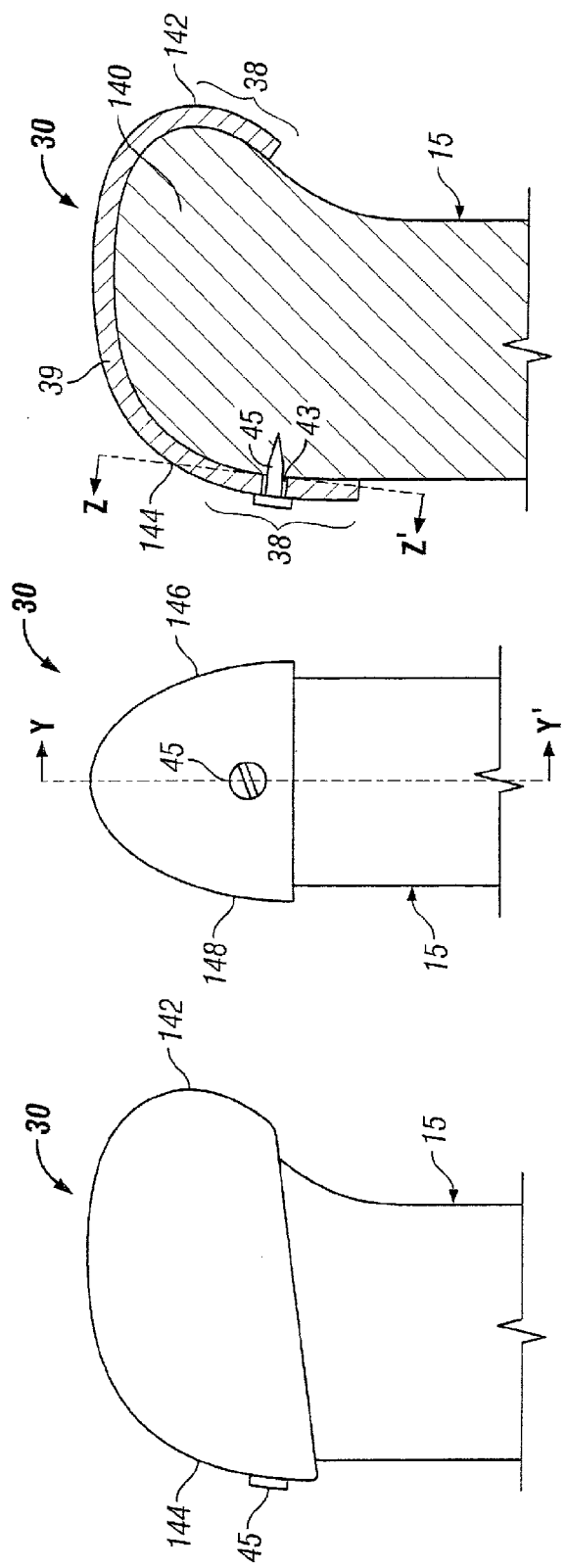

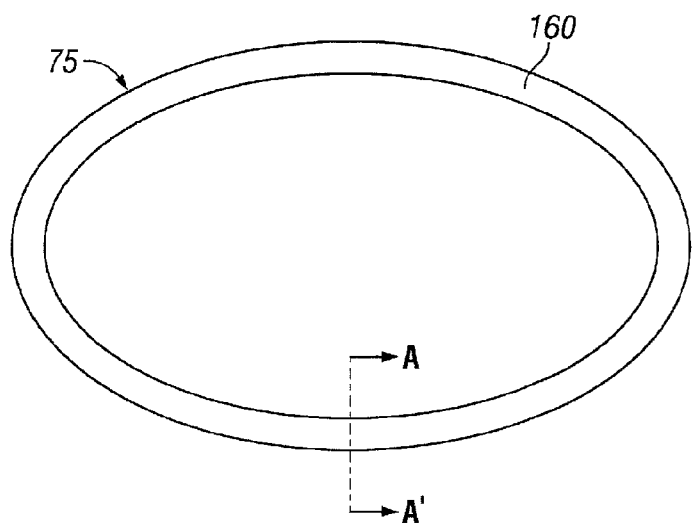
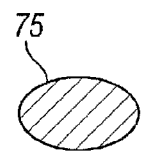
*FIG. 35*
*FIG. 34*
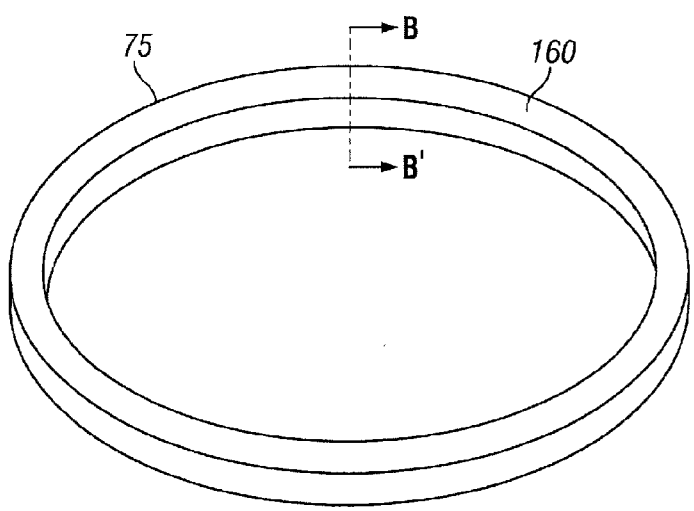
*FIG. 37*
*FIG. 36*

MOBILE PROSTHESIS FOR INTERPOSITIONAL LOCATION BETWEEN BONE JOINT ARTICULAR SURFACES AND METHOD OF USE

RELATED APPLICATIONS

This application is a continuation-in-part of U.S. patent application Ser. No. 13/939,653 filed Jul. 11, 2013 which is a continuation of U.S. patent application Ser. No. 13/352,399 filed Jan. 18, 2012, issued as U.S. Pat. No. 8,506,637 on Aug. 13, 2013 which is a continuation-in-part of U.S. application Ser. No. 12/591,845 filed Dec. 2, 2009 which is a continuation of U.S. patent application Ser. No. 11/710,614 filed Feb. 26, 2007, issued as U.S. Pat. No. 7,670,381 on Mar. 2, 2010; and which claims the benefit of priority to U.S. provisional patent application Ser. No. 61/435,017 filed Jan. 21, 2011, pursuant to 35 U.S.C. §119(e).

SCOPE OF THE INVENTION

This invention relates generally to medical implant devices and, more particularly, to a biocompatible prosthetic device comprising a thin low friction spacer for location to overlie a bone member in an interpositional location between opposed bone joint articular surfaces.

BACKGROUND OF THE INVENTION

Mammalian, and notably human joints, are subject to damage notably from trauma and disease. Both repetitive micro-trauma with occurrence more frequently than a capacity for healing and macro-trauma with significant immediate damage which cannot be recoverable by healing can lead to advancing bone damage. Early stage joint trauma and disease which are not healed typically can lead to a spectrum of pathological conditions of minor joint damage, advancing bone damage, degenerative joint disease and osteoarthritis.

Mammalian joints characteristically join a first bone member to a second bone member and include diarthrodial joints particularly those in which load bearing contiguous bone surfaces of each of the first and second bone members are covered with articular cartilage forming a respective margin of each of the first and second bone members. The contiguous bony surfaces of the surfaces which are normally in contact during movement of the joint are to be contrasted with non-contiguous surfaces of the bone members being surfaces which are not normally in contact during movement of the joint. The articular cartilage is provided as an outer layer over the sub-chondral bone, that is, the bone underlying the cartilage on the condyle at the end of the bone member. A condyle is a round projection or rounded articular area which can generally be characterized as a load bearing surface of a bone member. Articular cartilage is very poorly vascularized and, when damaged by trauma or disease, heals extremely slowly.

Most mammalian joints have, in addition to merely opposing bone members and their cartilage, synovial membranes which may provide synovial fluid proximate or intermediate the bearing surfaces and many joints are also provided with, to be divided completely or incompletely, by an articular disk or meniscus typically provided intermediate opposing articular cartilages.

Joint traumas and disease include damage and disease to the synovial membranes and the articular disk and meniscus if present which lead towards destruction and tearing away of the articular disks or meniscus and subsequent damage to the articular cartilage and subsequent bone to bone contact and damage to the sub-chondral bone.

Presently existing techniques for treating advancing bone damage include firstly biological resurfacing for early stages of the bone damage and, secondly, prosthetic replacement for late stages of bone damage. Biological resurfacing techniques for reconstituting the cartilage include debridement, abrasion arthroplasty, drilling, microfracture techniques, autologous chondrocyte transplant techniques and stem cell seeded transplants. Biological resurfacing has numerous disadvantages and is often unsuccessful, notably due to the fact that cartilage is not vascularized, heals extremely slowly and due to the fact that loading to which the cartilage is subjected due to normal use of the joints destroys the cartilage. Thus, biological resurfacing techniques have a high failure rate. Dilemmas which face biological resurfacing include the requirement that joints must move to remain functional yet movement destroys the new cartilage and prevents new cartilage formation. Thus, only extensive protracted and functionally limited rehabilitation is available which results in significant health care and social costs.

Prosthetic replacement is a treatment technique in which, for example, the entire articular cartilage and sub-chondral bone is replaced by a synthetic member. Typically in prosthetic replacement, as for example in the hip which comprises a ball and socket type joint, the ball on one bone member is completely removed and replaced by the synthetic ball and the interior surface of the socket on the other bone member is completely replaced by a new synthetic socket. Prosthetic replacement suffers significant disadvantages that a patient suffers while its natural joint deteriorates to a sufficient extent that surgery is necessary; the surgery is expensive; and the surgery is biologically destructive and irreversible. Moreover, the new joint is destined to failure after a period of time. Huge health care and social costs are associated with prosthetic replacement.

SUMMARY OF THE INVENTION

To at least partially overcome these disadvantages of previously known devices and methods, the present invention provides a thin spacing prosthesis with preferably at least one low friction surface, the prosthesis being adapted for location about a bone member in an interpositional location between opposed bone joint articular surfaces preferably about a margin of articular cartilage of a bone member's condyle, preferably without any modification of the articular surface of the condyle.

The invention also provides a biomimetic technique and prosthesis for joints with menisci that have been removed such as the temporomandibular joint or knee joint and a meniscus-like biomimetic technique and prosthesis for joints that do not usually have menisci such as, for example, the hip joint.

An object of the present invention is to provide an improved method for treating bone disorders, deformities and diseases including a prosthesis for use in treatment of bone disease, a method of manufacturing the prosthesis and a surgical method for implantation of the prosthesis.

The present invention particularly provides a method of modification of an orthopaedic joint which joins a first bone member to a second bone member within a mammalian body.

The prosthesis preferably is a thin sheet-like member to overlie contiguous bony surfaces of a first of the bone member. The joint preferably is a diarthroidial joint in which contiguous bony surfaces on each of the first bone member and the second bone member are covered in articular cartilage forming a respective margin of the first bone member and a respective margin of the second bone member. In a preferred embodiment, a thin sheet-like prosthesis is placed to overlie the margin of the articular cartilage of the first bone member with the sheet member conforming to the shape of the margin of the articular cartilage of the first bone member. The prosthesis is preferably coupled to the first bone member at a non-contiguous surface of the first bone member with the prosthesis disposed in between the margin of the articular cartilage of the first bone member and the margin of the articular cartilage of the second bone member. The contiguous bony surfaces of each of the first and second bone members are surfaces which are normally in contact during movement of the joint. The non-contiguous surface of a bone member is a surface which is not normally in contact during movement of the joint.

The sheet-like prosthesis preferably has an inner surface and an outer surface with the inner surface overlying the margin of the articular cartilage of the first bone member in engagement therewith and substantially corresponding in shape to the margin of the articular cartilage of the first bone member. The prosthesis may be a sheet-like member with uniform thickness and therefore the outer surface of the sheet member will also substantially correspond in shape to the margin of the articular cartilage of the second bone member. On the other hand, the prosthesis may have varying thicknesses.

Preferably, the margin of the articular cartilage of the first bone member forms a convexly rounded articular outer surface of the bone member as, for example, of a condyle of the first bone member. The prosthesis may form a cap-like member over such convexly rounded articular outer surface. The outer surface of the prosthesis is preferably smooth and has a coefficient of friction sufficiently low to facilitate movement relative thereto of the articular cartilage forming the margin of the second bone member in normal movements of the joint and reduce friction without wear by engagement. Preferably, the prosthesis also has an inner surface which is smooth and also has a coefficient of friction sufficiently low to facilitate movement relative thereto of the articular cartilage forming the margin of the first bone member and reduce friction without wear by engagement. The inner surface preferably may resist bonding of the articular cartilage on the margin of the first bone member thereto. Preferably, both the outer surface and the inner surface are smooth.

In accordance with a preferred method, a scan such as a CT scan, is made of the body joint and a model, whether computerized and/or a three-dimensional physical model, is made of portions of the bone member to which the prosthesis is to be engaged. The model may either be a model in conformance with the exact shape of the bone member or may preferably be made to have an exterior surface similar to the margin of the articular cartilage but insofar as the articular cartilage may have depressions or the like, the model may be provided with a smooth surface as to eliminate any recesses in the margin due to pathology.

Thus, the model may have an exterior surface similar to the expected margin of the articular cartilage of the first bone member prior to being deformed due to pathology.

In accordance with manufacture of the prosthesis of the present invention, scanning of the bone member about which the prosthesis is to be fitted, may be carried out by conventional technologies. The creation of a model and mechanically forming, for example, a sheet of tantalum about the model is one way of making the prosthesis. However, the manufacture of a model is not necessary and it is possible, for example, to scan the bone member about which the prosthesis is to be fitted and develop a computer generated version of the prosthesis, suitably adapted for example to adjust or avoid irregularities or depressions in the scanned bone and then to directly arrange for manufacture of the prosthesis. For example, where the prosthesis is to be made from metal, this may be accomplished in a variety of known techniques such as, for example, machining, casting, bending, thermoforming, hydroforming and various other specialized metallurgical techniques. Other techniques may involve the use of complex models and moulds which can readily be made from the scan. Insofar as models or moulds are used, additional techniques for forming could include vacuum sputtering and the like. The particular manner of manufacture of the prosthesis is not limited.

The prosthesis may preferably be formed from metal and notably medically acceptable metals which are preferred because of their biocompatibility and of their ability to be selected to be relatively thin yet, to some extent, bear loads under some conditions and, to some extent, have some flexibility. The prosthesis need not be limited to being provided by metals and may, for example, comprise organic biocompatible materials, polymers, and plastic materials such as formed from a sheet or layer of low friction plastic or polymer materials. The material of the prosthesis could be biologic in origin as, for example, in vitro collagen which may be the patient's own cultured cells or biologically engineered product. The materials of the prosthesis may preferably be pliable, but may be rigid. The sheet member may comprise a composite of plastic or polymer materials as, for example, with metals or other materials preferably providing a smooth low friction outer surface as, for example, of metal or a coating such as low friction nylon and the like. Preferably, coatings which may have an inherent low friction or lubricity and biocompatibility.

In one preferred embodiment, the prosthesis may comprise metal and have a thickness in the range of 0.0005 inches to 0.05 inches and, preferably, in the range of 0.001 inches to 0.01 inches and, more preferably, in the range of 0.001 inches to 0.003 inches. Preferred metals are selected from biocompatible metals including, for example, tantalum, zirconium and titanium and alloys thereof.

One method of forming the prosthesis from sheet metal is to scan portions of the first bone member including the margin of the articular cartilage and non-contiguous surfaces of the first bone member approximate thereto, then form a three-dimensional model of the scanned portions and, subsequently, form a planar sheet of material about the model substantially in conformance with the shape of the model. Where the prosthesis is to be metal, a thin sheet or foil of the desired metal may be mechanically placed over the model and formed to conform to the shape of the margin of the articular cartilage over the model.

In use, the prosthesis is positioned within the body so that portions of the prosthesis overlie contiguous bony surfaces of the first bone member. The prosthesis is retained positioned on the bone member against displacement from desired positions and preferably against displacement which may lead to removal. Preferably, the prosthesis is retained positioned on the bone member with some relative movement permitted between the prosthesis and the articular surface of the first bone member and it is believed that such relative movement may be advantageous and renders the prosthesis a preferred biomimetic.

With many configurations of the prosthesis and with particular condyles of the first bone member, the complementary shape alone of the prosthesis and the condyle of the joint may be sufficient to retain the prosthesis on the margin of the articular cartilage of the first bone member in an acceptable relative position. For example, the prosthesis may also be secured to the first bone member by having a shape which sufficiently envelops the first bone member to resist removal. The prosthesis may be secured to the first bone member by being engaged about a reduced circumference neck of the first bone member leading to larger circumference portions of the bone member. Accomplishment of such circumferential technique for securing the prosthesis may utilize some mechanism for reducing the circumference of the prosthesis on installation including folding, or an inherent resiliency or a ligature such as a wire or strap for engaging about the reduced circumference neck of the bone. Portions of the prosthesis to engage about a reduced circumference neck may have the ability to expand over the larger circumference portions yet return to a reduced circumference as by being elastic, or resilient or having a shape memory. The prosthesis may be capable of being one piece, folded or gathered upon itself to permit insertion arthroscopically to be uncollapsed and unfolded within the body.

In one preferred embodiment, the prosthesis may comprise a sheet member comprising a cap-like portion with an opening defined by an edge of the sheet member. The opening having a circumferential extent. The sheet member about the opening being movable between a first configuration in which the circumferential extent of the opening is a first length and a second configuration in which the circumferential extent of the opening is a second length which is less than the first length. A circumferential ligature can be provided to engage the sheet member about the opening of the cap-like portion to move the sheet member about the opening from the first configuration to the second configuration and to maintain the sheet member about the opening in the second configuration. Preferably, a clasp member may be provided to secure opposite ends of the circumferential ligature together and maintain the sheet member about the opening in the second configuration. Preferably, a plurality of eyelet holes are provided on the sheet member circumferentially about the opening spaced from the edge with the circumferential ligature passing through the eyelet holes circumferentially about the opening. Loops may be provided spaced circumferentially near the edge about the opening with the eyelet openings provided through the loops. The circumferential ligature preferably has a circumferential extent about the opening which can be reduced. Preferably, spaced inwardly into the cap-like portion from the opening, the inner surface of the sheet member has a circumferential extent of a length which is greater than the second length. In one arrangement, one or more screw members are secured to a reduced circumference neck of a first bone member which is not normally in contact with the second bone member during movement of the joint. The circumferential ligature can be coupled to each screw member to limit relative rotation of the opening of the cap-like member about the neck. Preferably, the coupling of the circumferential ligature to each screw member prevents marginal movement of the sheet member relative the outer surface of the articular cartilage of the first bone member without displacement from engagement with the outer surface of the cartilage surface of the first bone member. The circumferential ligature may be coupled to each screw member in many manners. One simple preferred manner is to provide a loop of the circumferential ligature around a shank of a screw member as to be captured underneath an enlarged head of the screw member. Insofar as the prosthesis includes a clasp member to secure opposite ends of the circumferential ligature together, the clasp member may carry a coupling portion and the screw member may secure the coupling portion of the clasp member to the neck of the first bone member or to another portion of the first bone member which is not normally in contact with the second bone member during movement of the joint. The circumferential ligature may be secured to the first bone member via one or more screw members with each screw member preferably circumferentially spaced about the bone and cap-like portion from adjacent screw members.

It is believed to be preferred that the prosthesis may need merely to be stabilized relative to the non-articular surface of the first bone member, that is, located thereon against removal but with some movement permitted between the prosthesis and the articular surface of the first bone member. Thus, the prosthesis is coupled, secured or stabilized relative the first bone member but preferably not fixated, cemented or glued to the first bone member in a manner which prevents at least some minor relative movement. The prosthesis may be fixedly secured, fixated, secured with fasteners, cemented or glued to the first bone member against any relative movement, however, this is generally not considered preferable.

The prosthesis may be characterized as comprising an interpositional sheath portion of a spacer member which spacer member further includes a coupling portion connected to the sheath portion for coupling the spacer member to the first bone member at the non-contiguous surface of the bone member. The coupling portion may extend from the interpositional sheath portion overlying the contiguous surface of the first bone member to overlie the non-contiguous surface of the bone member. The coupling portion may be secured to the non-contiguous surface of the bone member by various methods. A preferred method uses a circumferential technique and has the coupling portion engaged about a reduced circumference neck of the first bone member leading to a larger circumference portion of the first bone member carrying the contiguous surface to be covered by the interpositional sheath portion. That is, the interpositional sheath portion may overlie contiguous surfaces including enlarged circumference bulbous portions of a bone condyle and the coupling portion may encircle a reduced circumference neck of the condyle.

The coupling portion may be secured to the non-contiguous surface of the bone member by mechanical fasteners such as known threaded surgical screws, preferably coupling or fastening the coupling portion to the non-contiguous surface of the bone member to permit relative movement between the coupling portion and the non-contiguous surface of the first bone member at least preferably between the interpositional sheath portion and the contiguous surface of the first bone member.

The prosthesis in its interpositional position preferably permits physiological loading of forces applied across the joint, that is, loading which is appropriate to healthy, normal functioning of the joint. Preferably, the prosthesis is adapted to distribute loading forces which may be applied to the sheet member on one of its surfaces over an increased area on the other opposite of its surfaces. This can be of assistance in distributing loading which might normally be applied to a damaged area of the bone member or its cartilage to areas adjacent of the bone member or its cartilage which are not damaged. This is believed to avoid continued damage to the damaged areas of the bone member as to its cartilage or underlying bone and will assist in protecting existing cartilage or underlying bone; preserving the same without further damage and facilitating healing. Preferably, the prosthesis assists in absorbing at least some of any load and distributing localized forces of any load over wider areas. The prosthesis may have a memory such that it returns to the shape of the model when deformed from such shape. The prosthesis may be a resilient member which has an inherent bias to return to the shape of the model when deformed from such shape and which resists deformation from the shape of the model. Some deformation of the prosthesis, whether resilient or permanent, in adapting to dynamic loading may be desirable, for example, to avoid having a small surface area location or "high spot" where focused, increased loading may arise if there were no deformation.

The interpositional location of the prosthesis is advantageous since it requires no destruction of existing tissue of the bone member, preferably no modification of the bone member whatsoever. A preferred prosthesis in providing protection, particularly to the margin of the articular cartilage of the first bone member over which it is closely received provides a protective function in the sense that it protects and preserves the underlying cartilage or bone, halts the advance of pathology and provides a respite for cellular repair in the normal healing courses of the underlying articular cartilage and/or bone member.

In some instances, damage to the first bone member whether to the articular cartilage or underlying bone may advantageously be at least partially treated to promote healing, or, repaired as for example by providing grafts, that is, transplanted living tissue surgically implanted and the prosthesis provides a protective outer cover.

The prosthesis in accordance with the present invention has the advantage of being non-destructive in the sense that it preserves existing tissue necessary for healing. This is believed to assist in faster rehabilitation after surgically applying the prosthesis and providing the increased potential for return to normal function. Use of a prosthesis in accordance with the present invention retains future options including removal; resurfacing of the joint; and joint replacement. The prosthesis is useful for joints in younger, more active patients as a first preferred option and does not prevent the use in the future of other treatment processes.

The prosthesis may be preferably inserted in a surgical operation with open arthrotomy, that is, cutting an incision into a joint.

The prosthesis in accordance with the present invention preferably is for insertion in a joint and to be left inserted as for the life of the patient. Since it is believed that since the presence of the prosthesis will assist in permitting cellular repair of the underlying cartilage and bone, it is also possible and appropriate to surgically remove the prosthesis after some period of time when the cartilage and/or bone member has sufficiently repaired itself.

The prosthesis of the present invention may be used in a wide variety of mammalian joints as for humans and, as well, for veterinary practice for animals. Preferred joints are diarthrodial joints which permit relatively free movement including ginglymus (hinge-type) joints; condyloid articulation joints; trochoid (pivot) joints; joints with articular reciprocal rotation; enarthrosis (ball-and-socket) joints; and arthrodia (gliding) joints, but not limited to these joints. The prosthesis may be advantageously used in humans in the temporomandiubular joint; ball and socket joints as in the shoulder joints, hip joints; knee joints; ankle joints; carpometacarpal joint of the thumb; wrist joints, carpal joints and most tarsal joints but not limited to use in such joints.

Insofar as the joints may have a synovial membrane, an articular disk or meniscus, the prosthesis of this invention may be utilized whether or not the membrane, articular disk or meniscus is present, intact or removed or altered. The prosthesis may also be used with joints that do not usually have menisci such as the hip joint and can provide, in effect, an artificial meniscus where none was previously.

One preferred use of a prosthesis of the present invention is in a human temporomandibular joint as a thin cap-like member fitted closely over the mandibular condyle to be located intermediate of the mandibular condyle and the mandibular fossa of the temporomandibular joint.

The prosthesis in accordance with the present invention may be customized as to shape to fit a particular condyle of the bone member upon which it is to be placed. The prosthesis may also be customized so as to provide a desired functionality of the prosthesis for the bone member and joint in question. For example, the prosthesis may be customized as to the extent that it has sufficient strength to withstand forces to which it is subjected without any significant deformation or deflection. For example, in the case of a severely damaged bone member, almost no deflection of a central portion of the prosthesis may be desired. The magnitude of the forces to be transferred through the prosthesis at any joint will vary, for example, with greater forces transferred through a knee joint than a temporomandibular joint and, therefore, different thicknesses of the prosthesis will be required to provide similar rigidity. Where a bone member has minimal damage, a thinner prosthesis may be preferred, possibly with increased resiliency.

Having regard to many factors such as to the nature of the material or materials from which the prosthesis is to be made, the nature of the joint and bone member onto which the prosthesis is to be applied; the nature and extent of the damage to the bone member; and the intended protective surface of the prosthesis; the relative shape, thickness, rigidity, resiliency and strength of the prosthesis may be suitably selected by persons skilled in the medical and material sciences arts.

While in the most preferred use of the prosthesis in accordance with the present invention, a first single sheet-like prosthesis is provided over at least part of the margin of the articular cartilage of a first bone member, in accordance with the present invention, it is also possible in the same joint to provide a second prosthesis, namely, a second sheet-like member to overlie at least part of the margin of the articular cartilage of the second bone member preferably with coupling the second prosthesis to the second bone member at a non-contiguous surface of the second bone member with the second sheet member disposed in between the margin of the articular cartilage of the second bone member and the outer surface of the first sheet member.

In a first aspect, the present invention provides a sock-like spacing prosthesis for enveloping an end and a neck of a first bone member in an orthopaedic joint and spacing the end of the first bone member from a second bone member normally in contact with the end of first bone member within a mammalian body, the prosthesis comprising a thin member having an inner surface and an outer surface, the thin member comprising an inner closed cap-like portion and an outer tubular coupling portion extending outwardly from the cap-like portion, the cap-like portion having an inner closed end and extending outwardly to a circumferentially extending peripheral cap opening, the coupling portion extending outwardly from a circumferentially extending inner opening at a peripheral inner end of the coupling portion to a circumferentially extending peripheral outer opening at a peripheral outer end of the coupling portion, the cap opening of the cap-like portion coupled to the inner opening of the coupling portion whereby the inner surface of the sheet member over the cap-like portion and the coupling portion defines a bone receiving cavity from the inner closed end of the cap-like portion outwardly through the cap-like portion to the coupling portion and through the coupling portion to the outer opening, the sheet member over the cap-like portion consisting of a sheet-like substrate carrying as each of the inner surface and the outer surface a layer of metal, the inner surface over the cap-like portion conforming in shape and size to an outer surface of the end of the first bone member and permitting the cap-like member to be longitudinally slidable over the end of first bone member through the outer opening to receiving the first bone member within the first bone receiving cavity within the cap-like portion, the coupling portion being changeable from an open position to a closed position, in the open position the tubular portion longitudinally slidable over the end of the first bone member through the tubular portion and its outer opening to locate the end of the first bone member within the cap-like portion and the coupling portion about the neck of the first bone member, the coupling portion changeable from the open position to the closed position in which closed position the inner surface over the coupling portion adopts a closed shape and size that conforms in shape and size to the shape and size of the outer surface of the neck of the first bone member to resist relative movement of the prosthesis relative the first bone member.

Preferably in the prosthesis of the first aspect, when in the closed position, the inner surface over the coupling portion conforming to the closed shape to locate the prosthesis on the first bone member in a desired position circumferentially and axially relative the first bone member and, more preferably, the coupling portion has an inherent memory to adopt an inherent shape corresponding to the closed shape.

Preferably in the prosthesis of the first aspect, the coupling portion is resilient and has an inherent bias to assume an inherent shape when displaced from the inherent shape, the coupling portion being changeable from the open position to the closed position due to the resiliency of the coupling portion and, more preferably, the inherent shape corresponding to the closed shape and wherein in the closed position the inner surface over the coupling portion conforming in shape and size to an outer surface of the neck of the first bone member to locate the prosthesis on the first bone member in a desired position circumferentially and axially relative the first bone member. The inherent shape may have a circumference less than the closed shape. The material of the coupling portion may have an inherent tendency, when located about the neck of first bone member within a mammalian body in the closed shape, with the passing of time to set adopting an inherent memory to the closed shape.

Preferably in the prosthesis of the first aspect, the coupling portion is changeable from the open position to the closed position due to the coupling portion comprising of a material which shrinks circumferentially when subjected to one of: (a) radiation of selected wavelength, such as light and ultraviolet light, (b) heat, or (c) a chemical shrinking reagent and, in the closed position, the coupling portion having an inherent memory to adopt a shape corresponding to the closed shape.

Preferably in the prosthesis of the first aspect, the sheet-like substrate having a thickness between the inner surface and the outer surface not greater than 0.01 inches and, preferably, the sheet-like substrate is selected from the group consisting of: a member consisting of metal, and a member comprising a composite of plastic or polymer materials with metal providing the inner surface and the outer surface as metal. The thin member over the coupling portion may comprise plastic or polymer materials. The sheet-like substrate may consisting of metal. The coupling portion preferably has a thickness between the inner surface and the outer surface not greater than 0.1 inches.

In a second aspect the present invention provides a combination of a sock-like spacing prosthesis and a first bone member in a mammalian bone joint, the first bone having an end and a neck, the prosthesis disposed about the end and the neck of a first bone member enveloping the end and the neck and spacing the end of the first bone member from a second bone member normally in contact with the end of the first bone member within the joint, the first bone member having an outer surface over the end and neck, the outer surface of the first bone member over the end of the first bone member comprising a contiguous outer surface which engages with a contiguous outer surface of the second bone member in normal movement of the joint, the neck of the first bone member comprising a non-contiguous surface of the first bone member which non-contiguous surface is not normally in contact with the second bone member during movement of the joint, the prosthesis comprising a thin member having an inner surface and an outer surface, the thin member comprising an inner closed cap-like portion and an outer tubular coupling portion extending outwardly from the cap-like portion, the cap-like portion having an inner closed end and extending outwardly to a circumferentially extending peripheral cap opening, the coupling portion extending outwardly from a circumferentially extending inner opening at a peripheral inner end of the coupling portion to a circumferentially extending peripheral outer opening at a peripheral outer end of the coupling portion, the cap opening of the cap-like portion coupled to the inner opening of the coupling portion whereby the inner surface of the sheet member over the cap-like portion and the coupling portion defines a bone receiving cavity from the inner closed end of the cap-like portion outwardly through the cap-like portion to the coupling portion and through the coupling portion to the outer opening, the sheet member over the cap-like portion consisting of a sheet-like substrate carrying as each of the inner surface and the outer surface a layer of metal, the inner surface over the cap-like portion conforming in shape and size to a shape and size of the outer surface of the first bone member over the end of the first bone member and permitting the cap-like member to be longitudinally slidable over the end of first bone member through the outer opening to receiving the first bone member within the first bone receiving cavity within the cap-like portion, the coupling portion being changeable from an open position to a closed position, in the open position the tubular portion longitudinally slidable over the end of the first bone member through the tubular portion and its outer opening to locate the end of the first bone member within the cap-like portion and the coupling portion about the neck of the first bone member, the coupling portion changeable from the open position to the closed position in which closed position the inner surface over the coupling portion adopts a closed shape and size that conforms in shape and size to the shape and size of the outer surface of the neck of the first bone member to resist relative movement of the prosthesis relative the first bone member, in the closed position with the prosthesis disposed about the first bone member, (a) the prosthesis receiving the first bone member within the first bone receiving cavity, (b) the inner surface of the cap-like portion engaging and closely overlying the outer surface of the first bone member over the end of the first bone member, and (c) the inner surface of the coupling portion engaging the outer surface of the first bone member over the neck circumferentially about the neck.

In the second aspect, preferably the joint is a diarthrodial joint in which the contiguous outer surfaces comprise contiguous bony surfaces on each of the first bone member and second bone member which are each covered with articular cartilage forming the respective contiguous outer surface of the first bone member and second bone member, and the contiguous bony surfaces on each of the first and second bone members are surfaces which are in contact during normal movement of the joint, and the neck comprises a non-contiguous surface adjacent the articular cartilage of the first bone member.

In a third aspect, the present invention provides a method of use of a sock-like spacing prosthesis for enveloping an end and a neck of a first bone member in a mammalian bone joint and spacing the end of the first bone member from a second bone member normally in contact with the end of first bone member within the joint, the outer surface of the first bone member over the end of the first bone member comprising a contiguous bony outer surface which engages with a contiguous bony outer surface of the second bone member in normal movement of the joint, the neck of the first bone member comprising a non-contiguous surface of the first bone member which non-contiguous surface is not normally in contact with the second bone member during movement of the joint, the prosthesis comprising a thin member having an inner surface and an outer surface, the thin member comprising an inner closed cap-like portion and an outer tubular coupling portion extending outwardly from the cap-like portion, the cap-like portion having an inner closed end and extending outwardly to a circumferentially extending peripheral cap opening, the coupling portion extending outwardly from a circumferentially extending inner opening at a peripheral inner end of the coupling portion to a circumferentially extending peripheral outer opening at a peripheral outer end of the coupling portion, the cap opening of the cap-like portion coupled to the inner opening of the coupling portion whereby the inner surface of the sheet member over the cap-like portion and the coupling portion defines a bone receiving cavity from the inner closed end of the cap-like portion outwardly through the cap-like portion to the coupling portion and through the coupling portion to the outer opening, the sheet member over the cap-like portion consisting of a sheet-like substrate carrying as each of the inner surface and the outer surface a layer of metal, the inner surface over the cap-like portion conforming in shape and size to an outer surface of the end of the first bone member and permitting the cap-like member to be longitudinally slidable over the end of first bone member through the outer opening to receiving the first bone member within the first bone receiving cavity within the cap-like portion, the coupling portion being changeable from an open position to a closed position, in the open position the tubular portion longitudinally slidable over the end of the first bone member through the tubular portion and its outer opening to locate the end of the first bone member within the cap-like portion and the coupling portion about the neck of the first bone member, the coupling portion changeable from the open position to the closed position in which closed position the inner surface over the coupling portion adopts a closed shape and size that conforms in shape and size to the shape and size of the outer surface of the neck of the first bone member to resist relative movement of the prosthesis relative the first bone member, the method comprising:

longitudinally sliding the prosthesis over the end of the first bone member through the tubular portion in the open position and its outer opening to locate the end of the first bone member within the cap-like portion and the coupling portion about the neck of the first bone member and, subsequently, changing the tubular portion from the open position to the closed position.

The method of the third aspect may include locating the cap-like portion relative the end of the first bone member so that the shape and size of the inner surface of the cap-like portion and the matching shape and size of the outer surface of the end of the first bone member complementarily coincide. Preferably, the method includes after the step of changing the tubular portion from the open position to the closed position, the setting the material comprising the coupling portion in the closed position so that the coupling portion has an inherent memory to maintain the closed shape.

The method of the third aspect may include providing the coupling portion to be resilient and having an inherent bias to assume an inherent shape when displaced from the inherent shape, with the coupling portion being changeable from the open position to the closed position due to the resiliency of the coupling portion, with the inherent shape corresponding to the closed shape, and with the method including locating the coupling portion relative the neck so that closed shape of the coupling portion and the matching shape and size of the outer surface of the neck of the first bone member complementarily coincide.

In the method of the third aspect, the sheet-like substrate may preferably have a thickness between the inner surface and the outer surface not greater than 0.01 inches, with the sheet-like substrate is selected from the group consisting of: a member consisting of metal, and a member comprising a composite of plastic or polymer materials with metal providing the inner surface and the outer surface as metal, with the thin member over the coupling portion comprising plastic or polymer materials, and with the sheet-like substrate preferably consisting of metal.

In the method of the aspect, the joint is preferably a diarthrodial joint with the bony outer surfaces of the first bone member and the second bone member, each covered with articular cartilage and the neck adjacent the articular cartilage of the first bone member.

In another aspect, the present invention provides a method of modification of an orthopaedic joint joining a first bone member to a second bone member within a mammalian body:

the first bone member having a contiguous outer surface which engages with a contiguous outer surface of the second bone member in normal movement of the joint, the method comprising coupling a spacer member to the first bone member to overlie the contiguous outer surface of the first bone member conforming to the shape the first bone member with the sheet member disposed in between the contiguous outer surface of the first bone member and contiguous outer surface of the second bone member.

In another aspect, the present invention provides a prosthesis for use in an orthopaedic joint joining a first bone member to a second bone member within a mammalian body, wherein the joint is a diarthrodial joint in which contiguous bony surfaces on each of the first and second bone are each covered with articular cartilage forming the respective margin of the first and second bone members;

the prosthesis comprising an interpositional sheath portion, the sheath portion comprising a thin sheet member having an inner surface and an outer surface, the inner surface of the sheet member conforming to the shape of the outer surface margin of the articular cartilage such that the sheath portion is adapted to over lie the outer surface of the articular cartilage of the first bone member, the sheath portion adapted to be disposed in between the outer surface of the articular cartilage of the first bone member and the outer surface of the articular cartilage of the second bone member.

In another aspect, the present invention provides a diarthrodial orthopaedic mammalian joint bone member spacing prosthesis, the prosthesis comprising a thin spacer sheet member having a continuous inner surface and a continuous outer surface and a thickness between the inner surface and the outer surface not greater than 0.01 inches, the sheet member consisting of a sheet-like substrate carrying as each of the inner surface and the outer surface a layer of metal, the sheet member comprising a cap-like portion with an opening defined by an edge of the sheet member, the inner surface of the sheet member over the cap-like portion is generally concave, the outer surface of over the sheet member the cap-like portion is generally convex, the opening having a circumferential extent, the sheet member about the opening is movable between a first configuration in which the circumferential extent of the opening is a first length and a second configuration in which the circumferential extent of the opening is a second length which is less than the first length, a circumferential ligature engaging the sheet member about the opening of the cap-like portion to move the sheet member about the opening from the first configuration to the second configuration. Preferably, a clasp member is provided to secure opposite ends of the circumferential ligature together and maintain the sheet member about the opening in the second configuration.

In another aspect, the present invention provides a spacing prosthesis between a first bone member and a second bone member in an orthopaedic joint within a mammalian body providing a resultant modified joint, prior to the joint being modified (a) the first bone member having a contiguous outer surface which engages with a contiguous outer surface of the second bone member in normal movement of the joint, (b) the joint is a diarthrodial joint in which the contiguous outer surfaces comprise contiguous bony surfaces on each of the first bone member and second bone member which are each covered with articular cartilage forming the respective contiguous outer surface of the first bone member and second bone member, and (c) the contiguous bony surfaces on each of the first and second bone members are surfaces which are in contact during normal movement of the joint, characterized by:

the prosthesis comprising a spacer member consisting of a thin sheet member having a continuous inner surface and a continuous outer surface and a thickness between the inner surface and the outer surface not greater than 0.01 inches, the sheet member consisting of a sheet-like substrate carrying as each of the inner surface and the outer surface a layer of metal, the inner surface of the spacer member conforming to the shape of the outer surface of the articular cartilage of first bone member, the sheet member disposed in between the contiguous outer surface of the first bone member and the contiguous outer surface of the second bone member with the inner surface of the sheet member overlying the contiguous outer surface of the first bone member in engagement therewith and with the outer surface of the sheet member facing the outer surface of the articular cartilage of the second bone member in engagement therewith, the inner surface of the sheet member having a coefficient of friction sufficiently low to facilitate relative movement of the inner surface of the sheet member and the articular cartilage forming the contiguous outer surface of the first bone member in engagement with the inner surface of the sheet member, the outer surface of the sheet member having a coefficient of friction sufficiently low to facilitate relative movement of the outer surface of the sheet member and the articular cartilage forming the contiguous outer surface of the second bone member in engagement with the outer surface of the sheet member, the contiguous outer surface of the first bone member forms a convexly rounded outer surface over a bulbous end of the first bone member joined to the first bone member by a neck of a reduced circumference than a larger circumference of a portion of the bulbous end, the sheet member comprising a cap-like portion with an opening defined by an edge of the sheet member, the cap-like portion overly the bulbous end with the opening about the neck, the inner surface of the sheet member over the cap-like portion is generally concave, the outer surface of over the sheet member the cap-like portion is generally convex, the sheet member about the opening is movable between a first configuration and a second configuration, in the first configuration the circumferential extent of the opening is greater than the circumferential extent of the opening in the second configuration, in the first configuration the opening being sufficiently large to permit passing of the bulbous end of the first bone member through the opening of the cap-like portion to locate the cap-like portion over the bulbous end with the edge disposed circumferentially around the neck, in the second configuration the circumferential extent of the opening being less than a circumferential extent of the larger circumference of the portion of the bulbous end, the sheet member is disposed about the opening in the second configuration with the opening engaged about the neck to resist removal of the sheet member from the first bone member, the neck of the first bone member comprising a non-contiguous surface of the first bone member adjacent the articular cartilage on of the first bone member which non-contiguous surface is not normally in contact with the second bone member during movement of the joint, a circumferential ligature engaging the sheet member about the opening of the cap-like portion to move the sheet member about the opening from the first configuration to the second configuration and maintain the sheet member about the opening in the second configuration.

In another aspect, the present invention provides a method of modification of an orthopaedic joint joining a first bone member to a second bone member within a mammalian body to provide a resultant modified joint including a spacer member, the first bone member having a contiguous outer surface which engages with a contiguous outer surface of the second bone member in normal movement of the joint, the joint is a diarthrodial joint in which the contiguous outer surfaces comprise contiguous bony surfaces on each of the first bone member and second bone member which are each covered with articular cartilage forming the respective contiguous outer surface of the first bone member and second bone member, the contiguous bony surfaces on each of the first and second bone members are surfaces which are in contact during normal movement of the joint, the first bone member having an adjacent outer surface adjacent to the contiguous outer surface of the first bone member which adjacent outer surface is not normally in contact with the second bone member during movement of the joint, the contiguous outer surface of the first bone member forms a convexly rounded outer surface over a bulbous end of the first bone member joined to the first bone member by a neck of a reduced circumference than a larger circumference of a portion of the bulbous end, the neck comprising the adjacent outer surface, the spacer member consisting of a thin sheet member having a smooth continuous inner surface and a smooth continuous outer surface and a thickness between the inner surface and the outer surface in the range of 0.0005 inches to 0.01 inches, the sheet member selected from a sheet of metal and a sheet member comprising a composite of plastic or polymer materials with metal providing the inner and outer surfaces as metal, the sheet member comprising a cap-like member with an opening defined within an edge of the sheet member, the method comprising coupling the sheet member to the first bone member with the inner surface of the sheet member to overlie the contiguous outer surface of the first bone member with the sheet member disposed in between the outer surface of the articular cartilage of the first bone member and the outer surface of the articular cartilage of the second bone member, the method including:

(a) passing the bulbous end of the first bone member through the opening of the cap-like member to locate the cap-like member over the bulbous end with the edge disposed circumferentially around the neck, (b) securing the sheet member about the neck with a circumferential ligature which extends circumferentially around the neck about the sheet member where the sheet member extends circumferentially about the neck, and (c) reducing a circumferential extent of the opening proximate the edge about the neck and maintaining the circumferential extent of the opening reduced with a circumferential ligature.

In another aspect, the present invention provides a prosthesis for use in an orthopaedic joint to join a first bone member to a second bone member within a mammalian body to provide a resultant modified joint, the first bone member having a contiguous outer surface which engages with a contiguous outer surface of the second bone member in normal movement of the joint, the joint is a diarthrodial joint in which the contiguous outer surfaces comprise contiguous bony surfaces on each of the first bone member and second bone member which are each covered with articular cartilage forming the respective contiguous outer surface of the first bone member and second bone member, and the contiguous bony surfaces on each of the first and second bone members are surfaces which are in contact during normal movement of the joint, wherein:

the prosthesis comprising a spacer member consisting of a thin sheet member having an inner surface and an outer surface and a thickness between the inner surface and the outer surface not greater than 0.01 inches, the sheet member consisting of a sheet-like substrate carrying as each of the inner surface and the outer surface a layer of metal, the inner surface of the spacer member conforming to the shape of the outer surface of the articular cartilage of first bone member, the sheet member adapted to be disposed in between the contiguous outer surface of the first bone member and the contiguous outer surface of the second bone member with the inner surface of the sheet member overlying the contiguous outer surface of the first bone member in engagement therewith and with the outer surface of the sheet member facing the outer surface of the articular cartilage of the second bone member in engagement therewith, the inner surface of the sheet member having a coefficient of friction sufficiently low to facilitate relative movement of the inner surface of the sheet member and the articular cartilage forming the contiguous outer surface of the first bone member in engagement with the inner surface of the sheet member, the outer surface of the sheet member having a coefficient of friction sufficiently low to facilitate relative movement of the outer surface of the sheet member and the articular cartilage forming the contiguous outer surface of the second bone member in engagement with the outer surface of the sheet member;

the contiguous outer surface of the first bone member forms a convexly rounded outer surface over a bulbous end of the first bone member joined to the first bone member by a neck of a reduced circumference smaller than a larger circumference of a portion of the bulbous end, the sheet member comprising a cap-like portion with an opening defined by an edge of the sheet member, the cap-like portion adapted to overly the bulbous end with the opening about the neck, the inner surface of the sheet member over the cap-like portion is generally concave, the outer surface of over the sheet member the cap-like portion is generally convex, the prosthesis being changeable from an opened position to a closed position, wherein, in the closed position of the prosthesis, the cap-like portion is adapted to overlie the bulbous end with the opening about the neck, in which closed position, the opening has a circumference which corresponds to the circumference of the neck. Preferably, the neck of the first bone member comprising a non-contiguous surface of the first bone member adjacent the articular cartilage of the first bone member which non-contiguous surface is not normally in contact with the second bone member during movement of the joint. More preferably, the sheet member is adapted for coupling to the first bone member with the inner surface of the sheet member to overlie both the contiguous outer surface of the first bone member and the adjacent non-contiguous surface of the first bone member, the sheet member comprising the closed cap-like portion and a circumferential neck coupling portion, the coupling portion including the opening through the coupling portion defined by an edge of the sheet member, the coupling portion extending circumferentially about the opening between the opening and the cap-like portion, the cap-like portion overlies in the closed position of the prosthesis the bulbous end with the coupling portion and its opening about the neck, in which closed position the opening has a circumference which corresponds to the circumference of the neck.

BRIEF DESCRIPTION OF THE DRAWINGS

Further aspects and advantages of the present invention will become apparent to one skilled in the art upon reading the following specification and the following drawings:

FIG. 25 is a front elevation view showing a prosthesis in accordance with a seventh embodiment of the present invention as applied to a condyle of a diarthrodial joint;

FIG. 26 is a side elevation view of the prosthesis and condyle shown in FIG. 25;

FIG. 27 is a cross-sectional view along section line Y-Y' in FIG. 26;

FIG. 34 is a pictorial view of a first ring useful as a circumferential ligature;

FIG. 35 is a cross-sectional view along section line A-A' in FIG. 34;

FIG. 36 is a pictorial view of a second ring useful as a circumferential ligature;

FIG. 37 is a cross-sectional view along section line B-B' in FIG. 36;

DETAILED DESCRIPTION OF THE DRAWINGS

Figure 1:
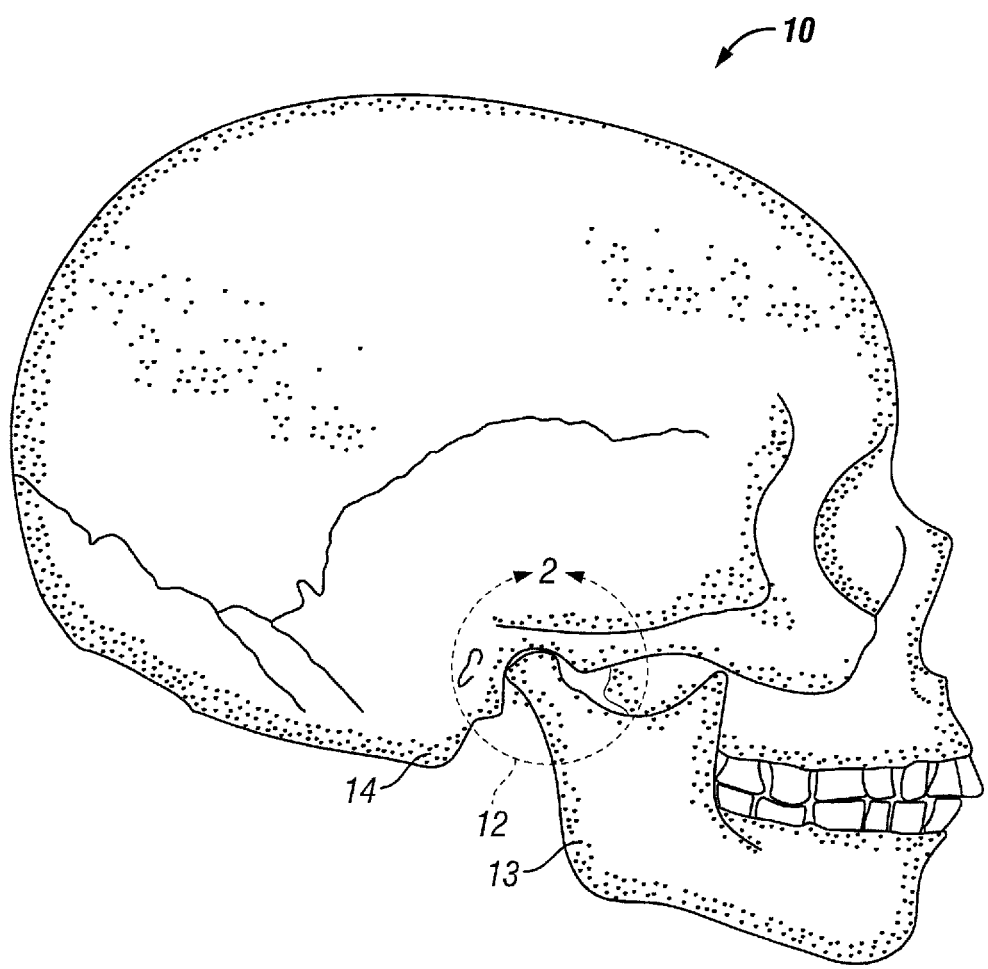
FIG. 1 is a side view of a human skull illustrating the natural environment of a temporomandibular joint.
Figure 2:
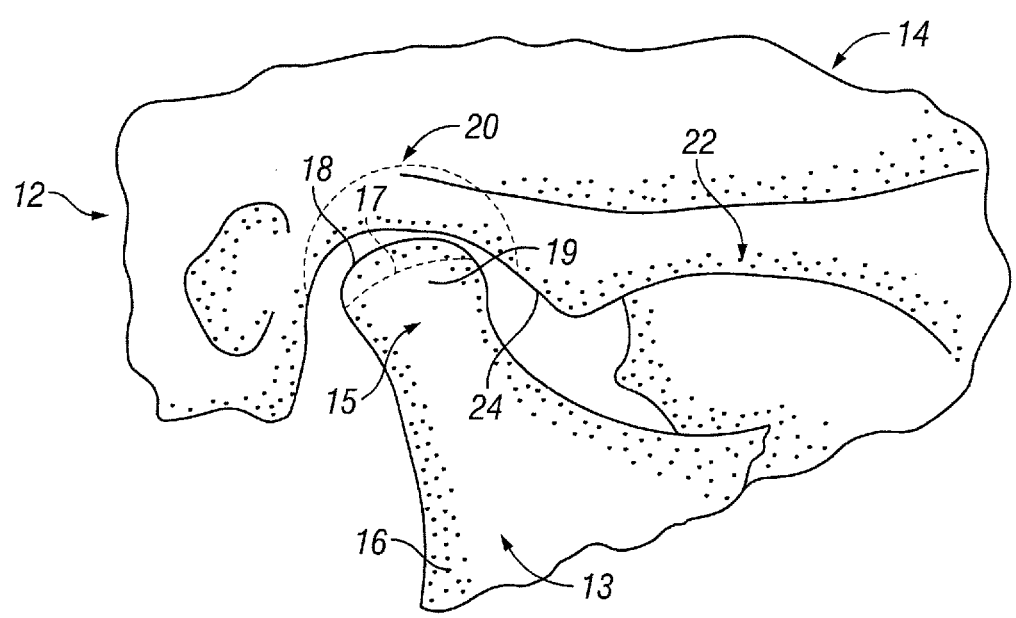
FIG. 2 is an enlarged side view illustrating the temporomandibular joint region shown in FIG. 1.
Figure 3:
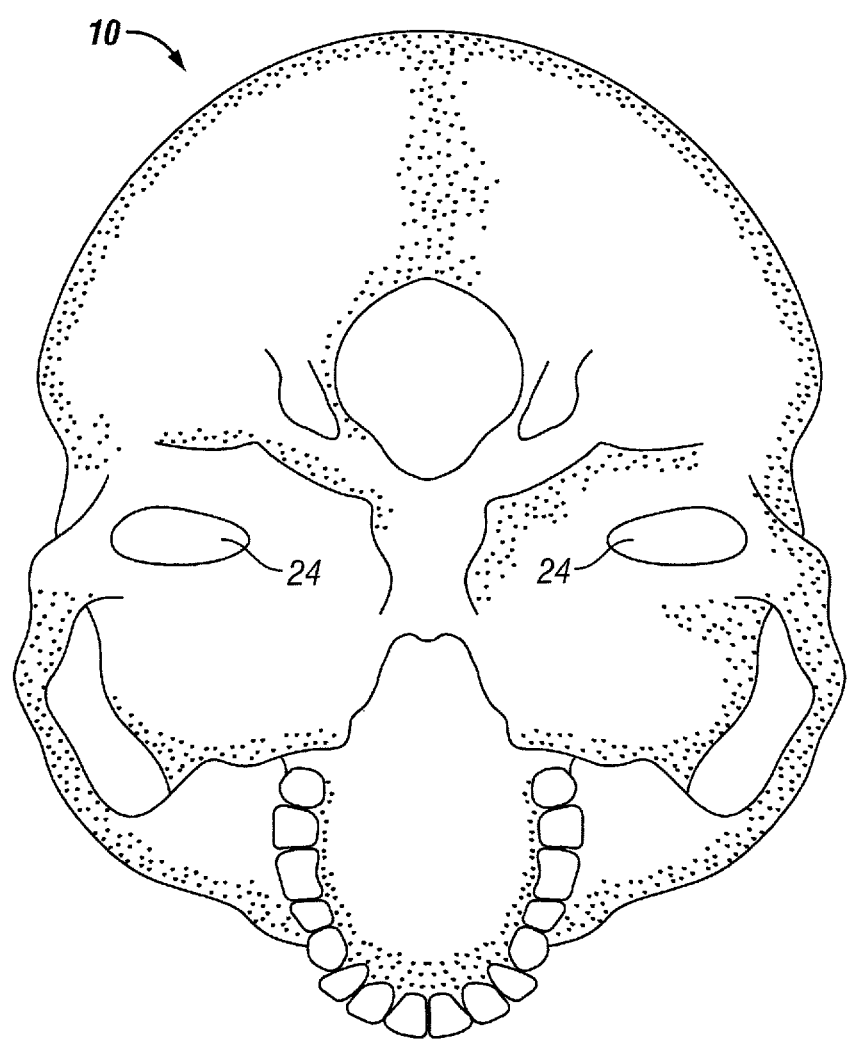
FIG. 3 is a bottom view of a human maxilla illustrating a natural mandibular fossa of a temporomandibular joint.

Referring now to FIG. 1, there is shown a side view of a human skull 10 illustrating the natural environment of a temporomandibular joint region 12. The temporomandibular joint region 12 is shown in enlarged fashion in FIG. 2 as including a mandible 13 and a temporal bone 14. As seen in FIG. 2, the mandible 13 includes a condyle 15 which is a natural protrusion of the ramus 16. The condyle 15 is further shown to include an articular surface 18 which is naturally of a generally rounded convex configuration. The temporomandibular joint region 12 also includes a mandibular fossa 20 which is a region adjoining the zygomatic arch 22. The mandibular fossa 20 includes an articular surface 24 which is of a generally rounded concave configuration.

Figure 5:
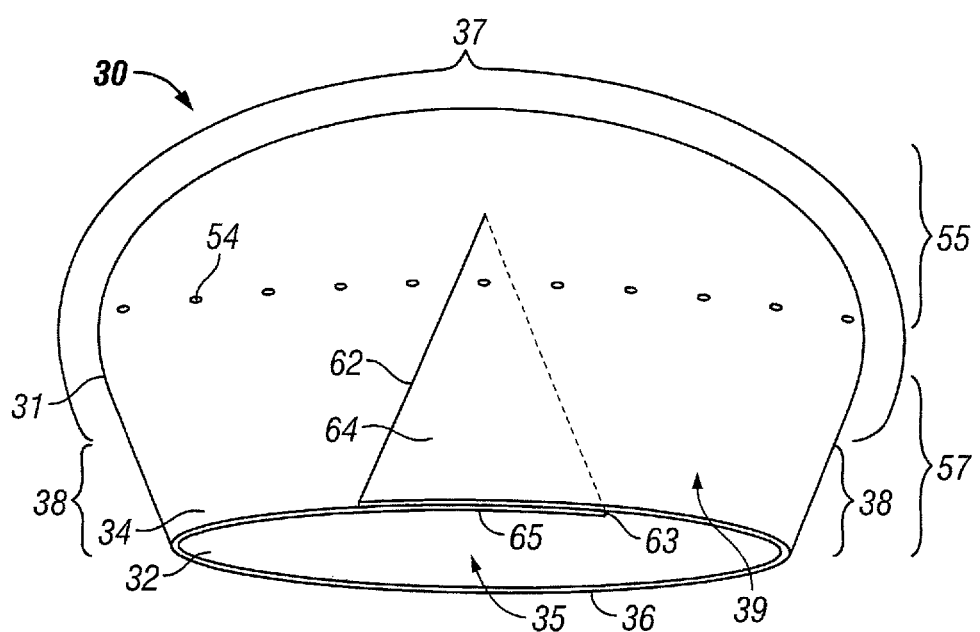
FIG. 5 is a pictorial view of a first embodiment of a prosthesis in accordance with the present invention in a closed configuration it is to assume when applied onto the condyle of the temporomandibular joint shown in FIG. 4.

Reference is made to FIG. 5 which illustrates a preferred embodiment of a prosthesis 30 in accordance with the present invention. The prosthesis 30 comprises a hollow cap-like member with a wall 31 providing an inwardly directed inner surface 32 and an outwardly directed outer surface 34. The prosthesis 30 as a cap-like member has an opening 35 surrounded by edge 36 of the wall 31. In the preferred embodiment, the inwardly directed surface 32 is generally concavely rounded and the outwardly directed surface 34 is a parallel mirror image of the inwardly directed surface 32 and, accordingly, the outer surface 34 is convexly outwardly rounded. The inner surface 32 of the prosthesis 30 is formed to have a shape which is substantially identical to the articular surface 18 of the condyle 15 onto which the prosthesis 30 is to be coupled.

Figure 4:
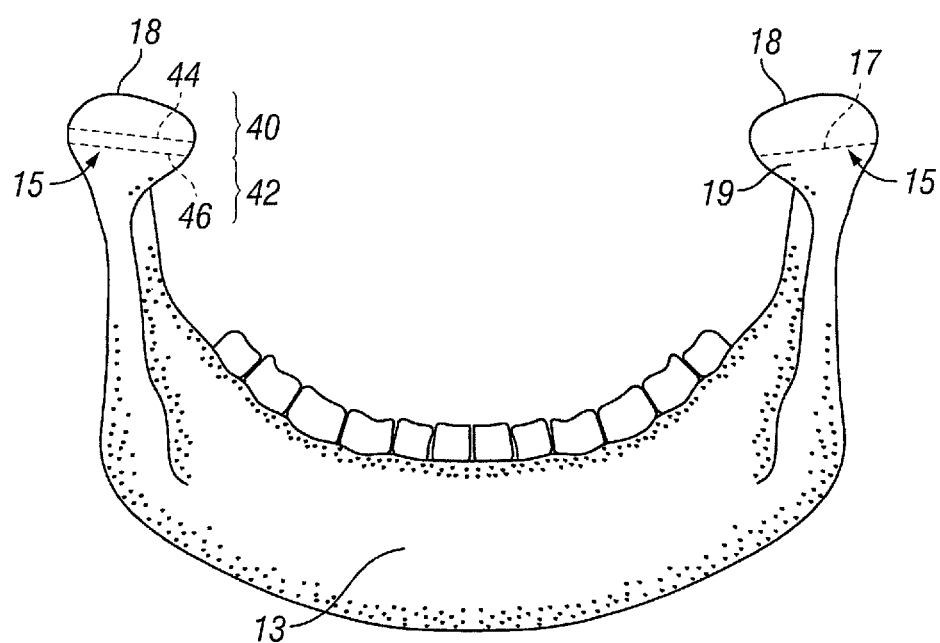
FIG. 4 is a posterior-to-anterior view of a human mandible illustrating the environment of a natural condyle of a temporomandibular joint.

The condyle 15 as seen in FIG. 4 has a bulbous end 40 joined to the remainder of the bone by a neck 42. The bulbous end 40 has portions with larger circumferences than portions of the neck 42. For example, the bulbous end has a largest circumference 44 as indicated by a single dot line, and the neck 42 has a smaller circumference 46 as indicated by a double dot line.

The internal surface of prosthesis 30, as seen in FIG. 5, similarly has a largest circumference at 54 indicated by a single dot line and corresponding to largest circumference 44 of the bulbous end 40 of the condyle 15. The prosthesis 30, as seen in FIG. 5, has a smaller circumference at its opening 35 which corresponds to smaller circumference 46 of the neck of the condyle 15.

The prosthesis 30 is shown in FIG. 5 in a closed configuration which it is to assume when applied over the condyle 15 and which shape it may be formed to inherently adopt. The prosthesis 30 of FIG. 5 is adapted to assume the opened configuration shown in FIG. 6 for insertion of the prosthesis onto the condyle 15, and which opened configuration can represent one configuration which a pre-form of the prosthesis 30 may assume during its manufacture. The opened prosthesis 30 of FIG. 6 has a largest circumference at the single dot line 54 and an inner portion 55 above its largest circumference 54 corresponding to the upper portion of the bulbous end 40 of the condyle 15 above its largest circumference 44.

Figure 6:
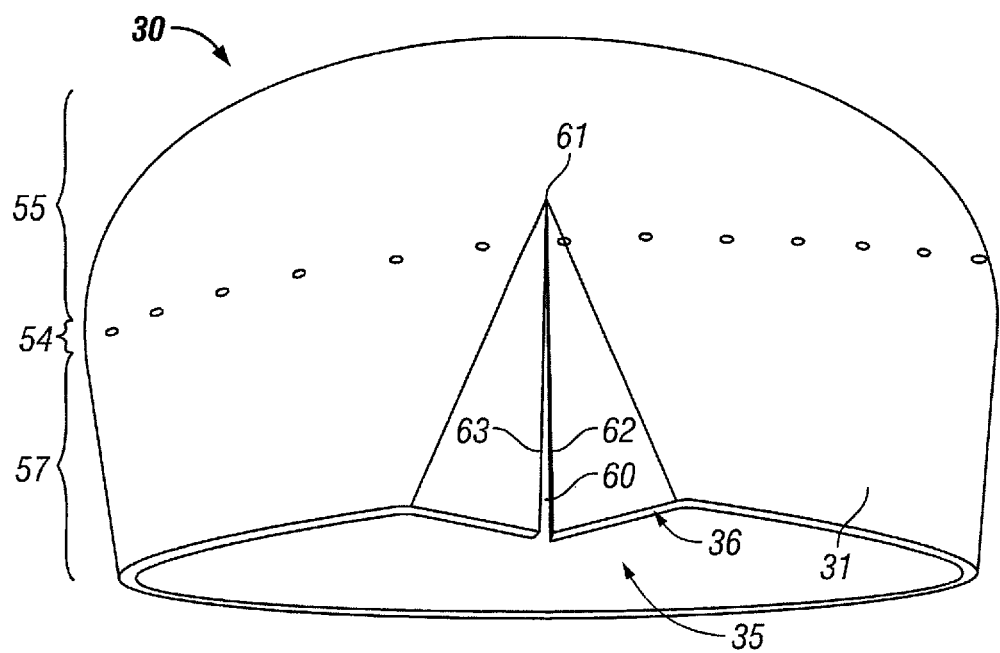
FIG. 6 is a pictorial view of the prosthesis of FIG. 5 in an expanded configuration.

A cut 60 through the wall 31 extends from the edge 36 of the wall 31 inwardly to a point 61 defining two cut edges 62 and 63. Having regard to the circumference of the wall 31 outward of the circumference 54 and the ability of the cut edges 62 and 63 to be moved apart to increase such circumference, the prosthesis 30 of FIG. 6 is adapted to be slid down over the condyle 15 to seat the bulbous end 40 of the condyle 15 in the upper portion 55 of the opened prosthesis 30. Subsequently, the cut edges 62 and 63 may be moved to the closed position of FIG. 5 that is moved circumferentially past each other so that a flap 64 adjacent the cut edge 62 overlies a flap 65 adjacent the cut edge 63, reducing the circumference of a lower portion 57 of the prosthesis 30 to assume the reduced circumferences of the neck 42 of the condyle 15 as at the opening 35 of the closed prosthesis 30 in FIG. 5.

In the embodiment of FIG. 6, the circumference of the prosthesis 30 outward of the largest circumference 54 is generally proximate to that of the largest circumference 54, albeit reducing marginally towards the opening 35.

As seen in FIGS. 7 to 10, the prosthesis 30 is coupled to the mandibular 13 so as to overlie the articular surface 18 of the condyle 15.

The temporomandibular joint is one example of a diarthrodial joint in which contiguous bony surfaces on each of the condyles 15 of the mandibular 13 and the articular surface 24 on the mandibular fossa 20 are each covered with articular cartilage forming the respective outer surfaces or margins of these bone members. Adjacent surfaces of these bone members are non-contiguous surfaces in a sense that they are not normally in contact in a manner to be force transferring through the joint during movement of the joint. In FIGS. 2 and 4, a dashed line 17 schematically illustrates a boundary between the contiguous bony surfaces carrying articular cartilage 18 and non-contiguous surfaces 19 of the mandibular 13.

Figure 7:
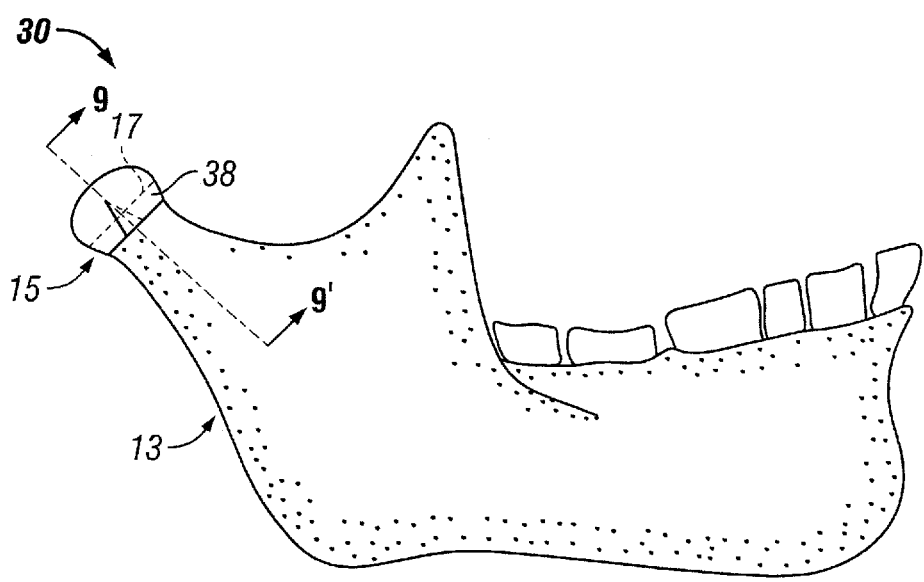
FIG. 7 is an enlarged right side view of the mandibular shown in FIG. 3 with the prosthesis of FIG. 5 coupled to the right side condylar process of the mandibular.
Figure 8:
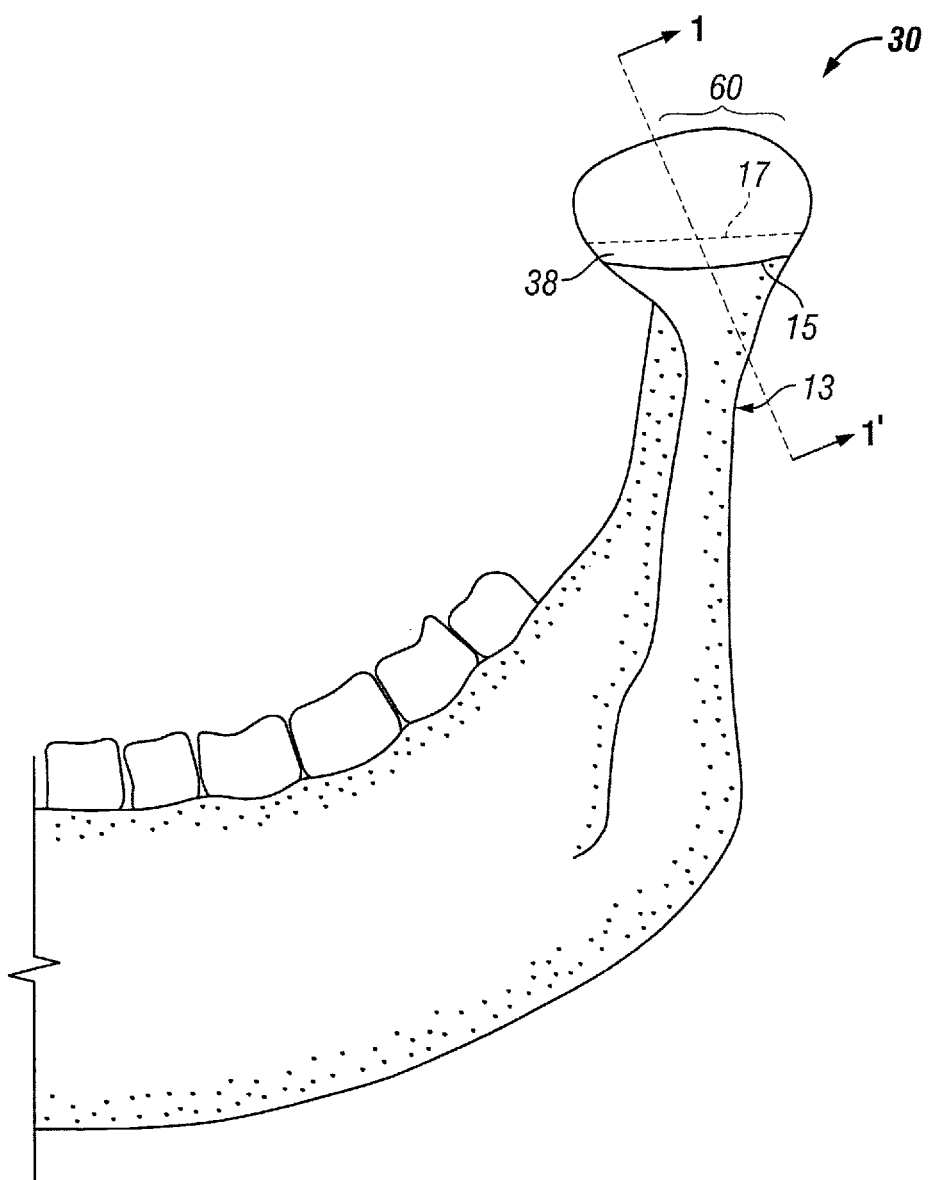
FIG. 8 is an enlarged posterior-to-anterior view of the right side condylar process of the mandibular shown in FIG. 7 with the prosthesis applied thereto.

Referring to FIGS. 7 and 8, the prosthesis 30 is shown as applied to the mandibular 13 to substantially entirely cover the outer surface of the articular cartilage 18 of the contiguous bony surfaces, that is, of the condyle 15 on the mandibular 13. The prosthesis 30 includes a coupling portion 38 which, as seen in FIG. 7, extends clearly beyond the articular cartilage 18 and over the non-contiguous surface 19 of the mandibular 13. The prosthesis 30 is marked to indicate the coupling portion 38, as seen in FIG. 5, which is provided over the non-contiguous surface 19 and is of reduced circumference to couple the prosthesis about the neck of the condyle. As is to be appreciated from the Figures with the prosthesis 30 applied to the joint, in the resultant modified joint during normal movement of the joint, the prosthesis 30 consists of the only element foreign to the joint which engages the contiguous bony surfaces on each of the condyle 15 and the mandibular 13, and the prosthesis 30 consists of the only element foreign to the joint which is located between the contiguous outer surface of the condyle 15 and the contiguous outer surface of the mandibular 13.

Figure 9:
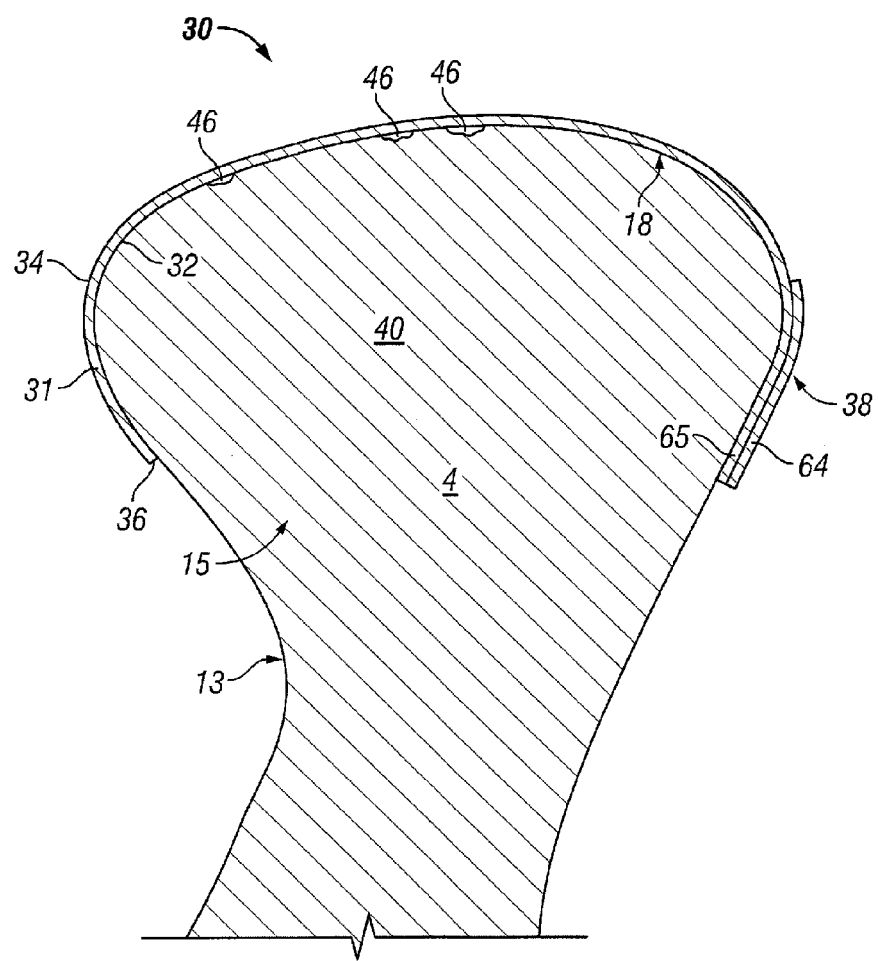
FIG. 9 is a cross-sectional side view along section line 9-9' in FIG. 7 of the right side condylar process of the mandibular shown in FIG. 7 with the prosthesis applied thereto.
Figure 10:
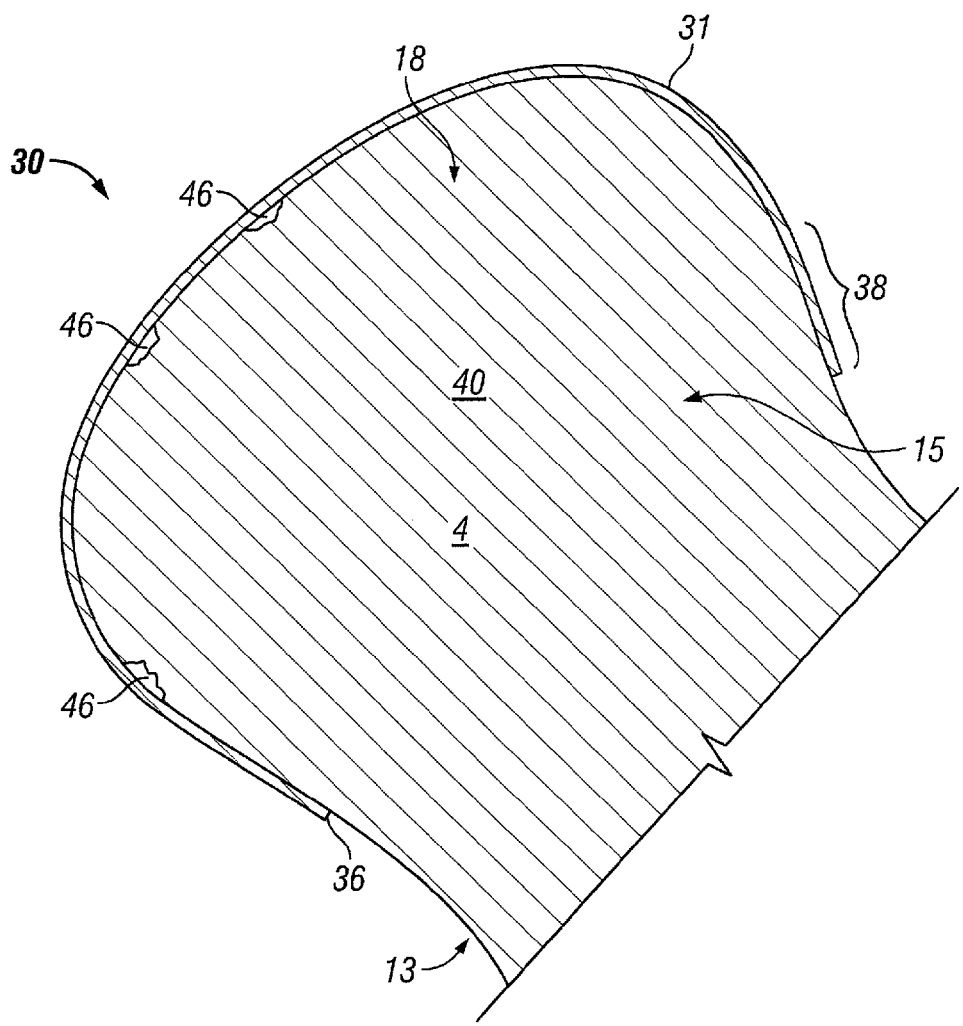
FIG. 10 is a cross-sectional side view of the right side condylar process of the mandibular shown in FIG. 7 along section line 1-1' in FIG. 8.

The prosthesis 30, as best seen in FIGS. 9 and 10, has its interior surface conforming to the shape of the margin, that is, the exterior surface of the articular cartilage 18. FIGS. 9 and 10 schematically illustrates depressions 46 in the articular cartilage 18 as, for example, may be formed due to damage to the cartilage 18. The prosthesis 30 preferably is provided to have a smooth continuous exterior surface 34 which adopts a profile of the articular cartilage 18 assuming that the depressions 46 were not present. The wall 31 of the prosthesis 30 in spanning across the depressions 46 assists in distributing any loading which normally would be applied to the depressions 46 over a greater surface area on the prosthesis 30 and on the surface of the articular cartilage 18.

The prosthesis 30 is preferably formed by a method including scanning the condyle of the mandibular to develop a computerized model of the condyle and notably the shape of the outer surfaces of its articular cartilage and adjacent non-contiguous surfaces. Such scanning may be carried out as by computerized tomography (CT) scans or other imaging techniques.

The computerized model of the condyle may preferably be used to make a physical three-dimensional model of the condyle, placing a foil or sheet of metal over the model and conforming the foil or sheet to adopt the shape of the model. Preferably, a thin sheet of metal as may be commercially available such as tantalum foil of thickness $2/1000^{th}$ of an inch may be manually placed over the model and stretched, formed, thermoformed and/or conformed to the shape of the model, preferably with fold lines or sharp edges minimized, rounded or avoided as far as possible over the contiguous surfaces.

The prosthesis 30 of FIG. 5 comprises a thin sheet member 39 of metal which has been formed over a model of the condyle. FIG. 5 and FIGS. 6 to 14 have not been drawn to scale for ease of illustration, at least in respect of when the thickness of the sheet member 39 is to represent a metal sheet of, say, $2/1000^{th}$ inch.

The prosthesis 30 as illustrated in FIG. 5 may be seen to have its sheet member 39 comprise an interpositional sheath portion 37 of substantially constant width between its inner surface 32 and outer surface 34 adapted to overlie the outer surface of the articular cartilage 18 of the condyle 15 of the mandibular 13 with coupling portion 38 bridging from the sheath portion 37 to overlie non-contiguous surfaces 19 of the condyle 15 adjacent to the articular cartilage 18 thereof and about the reduced circumference neck 42.

The prosthesis 30 may be made as by various processes not limited to making a physical model of the condyle and forming material of the prosthesis over the model. The prosthesis could be made otherwise as by computer controlled machining from a block of metal to have the desired shape and polishing.

The prosthesis 30 is to be secured onto the actual mandibular 13 of a human by a surgical process, namely, open arthrotomy in which the condyle of the mandibular is exposed, the prosthesis is placed over the condyle 15 and secured to the mandibular.

Providing the prosthesis to be made from sheet materials or to have its interpositional sheet portion to be of constant thickness is not necessary. However, providing the thickness of the wall to be of constant thickness is of assistance in achieving the objective of having the outer surface of the prosthesis closely mimic the shape and size of the outer surface of the articular cartilage of the condyle of the mandibular. However, any prosthesis may be adjusted or modified so as to have a wall which may not have a uniform thickness. For example, certain instances may be desirable to provide the prosthesis 30 with increased features of strength, resistance to deformation or resiliency for different portions on the prosthesis. For example, it may be desired to have increased thickness and resistance to deformation over central portions of the articular cartilage and it could be possible as by suitable machining to provide increased thickness over the central end areas without significantly altering the outside surface to have a surface which is different from the shape of the condyle. Such central portions of increased thickness could, having regard to the material of the prosthesis, increase the extent that any forces are distributed over an enlarged area to reduce localizing forces on smaller areas of the articular cartilage. Similarly, the thickness of the wall of the cup-like member proximate its circumferential perimeter for over an area proximate the circumferential perimeter could be reduced in thickness.

Figure 11:
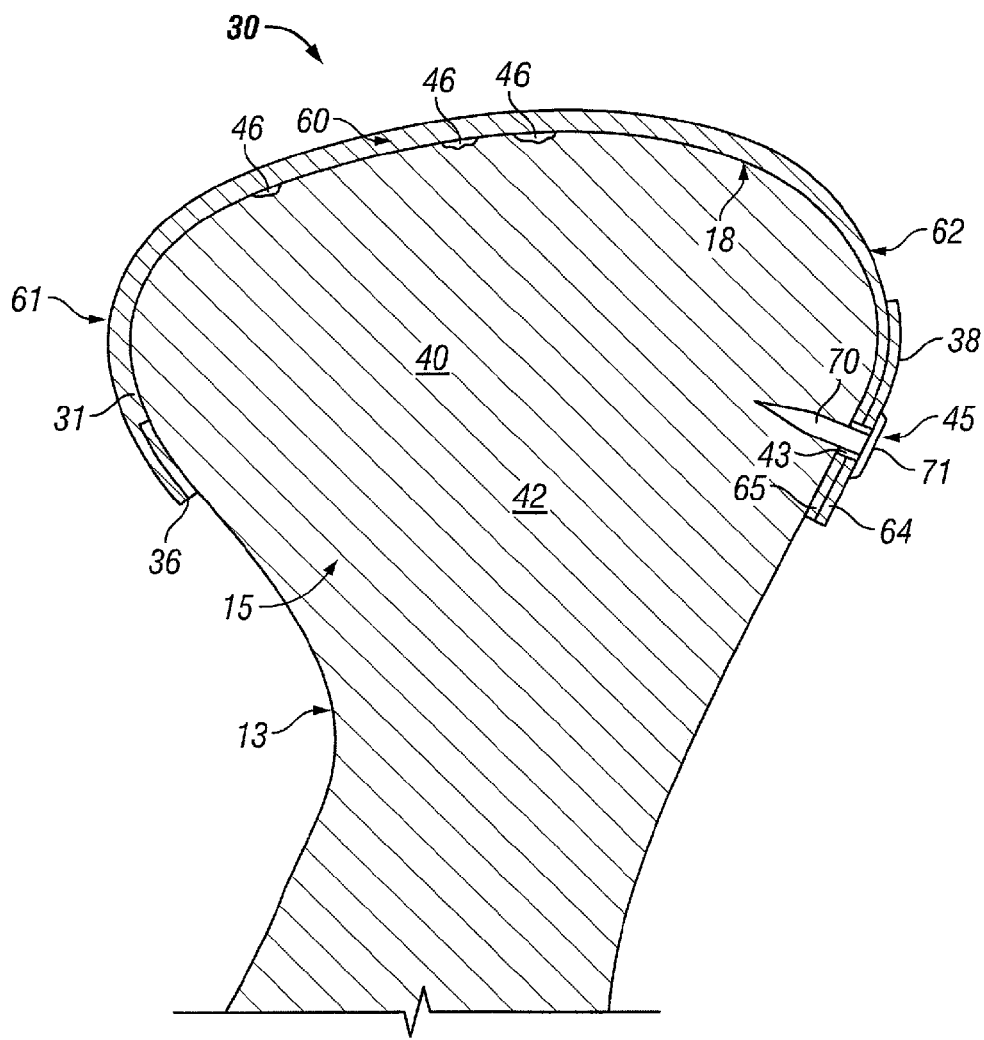
FIG. 11 is a cross-sectional view similar to that in FIG. 9 but with the prosthesis having a central portion of its wall of increased thickness and being additionally secured by a surgical screw.

Reference is made to FIG. 11 which shows a cross-sectional view similar to that in FIG. 9, however, of a modified embodiment of the prosthesis 30. As one modification, the prosthesis 30 has a central portion 60 of its wall of an increased thickness compared to side portions 61 and 62. The increased thickness of the central portion 60 of the wall assists in distributing localized forces applied to areas on either side of the central portion 60 being distributed to enlarged areas as is believed to provide increased protection to the articular cartilage with which the central portion contacts.

As a second modification, aligned holes 43 are provided through the overlapping flaps 64 and 65 and a surgical screw 45 is shown extending through the holes 43 and into the condyle 15 to mechanically fasten the coupling portion 38 of prosthesis to the condyle 15 over its non-contiguous surface. While the screw 45 could be tightened sufficiently to draw the flaps 64 and 65 into the condyle 15 against relative movement, it is preferred as shown that the holes 43 be larger than the shank 70 of the screw 45 and the screw 45 be tightened so as to permit relative sliding of the flaps 64 and 65 underneath the head 71 of the screw 45.

As a third modification, FIG. 11 shows on a left-hand side only the wall 31 at the lower edge 36 bent back underneath itself to provide a reinforced and smooth edge at the edge 36.

Figure 12:
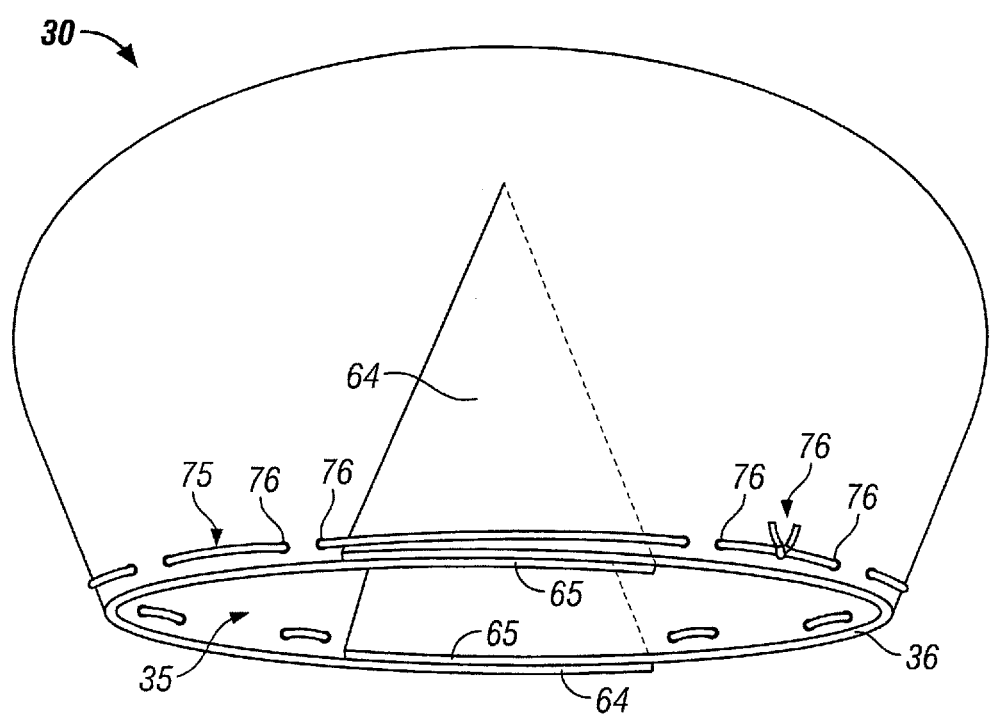
FIG. 12 is a pictorial view of a second embodiment of a prosthesis similar to that in FIG. 5 and including a closing ligature.

Reference is made to FIG. 12 which shows a second embodiment of a prosthesis 30 as in FIG. 5 but modified firstly to provide cut lines and corresponding flaps 64 and 65 on two sides and, secondly, to provide circumferential ligature 75. As seen, a plurality of small spaced eyelet openings 76 are provided circumferentially inwardly from the edge 36 through which the ligature 75 is passed. The ligature may comprise a suture-like string or wire which may have its ends secured together as at 76 to maintain the opening 35 with its reduced circumference. As is to be appreciated from the Figures with the prosthesis 30 applied to the joint, in the resultant modified joint during normal movement of the joint, the prosthesis 30 and the circumferential ligature 75 consist of the only elements foreign to the joint.

Figure 13:
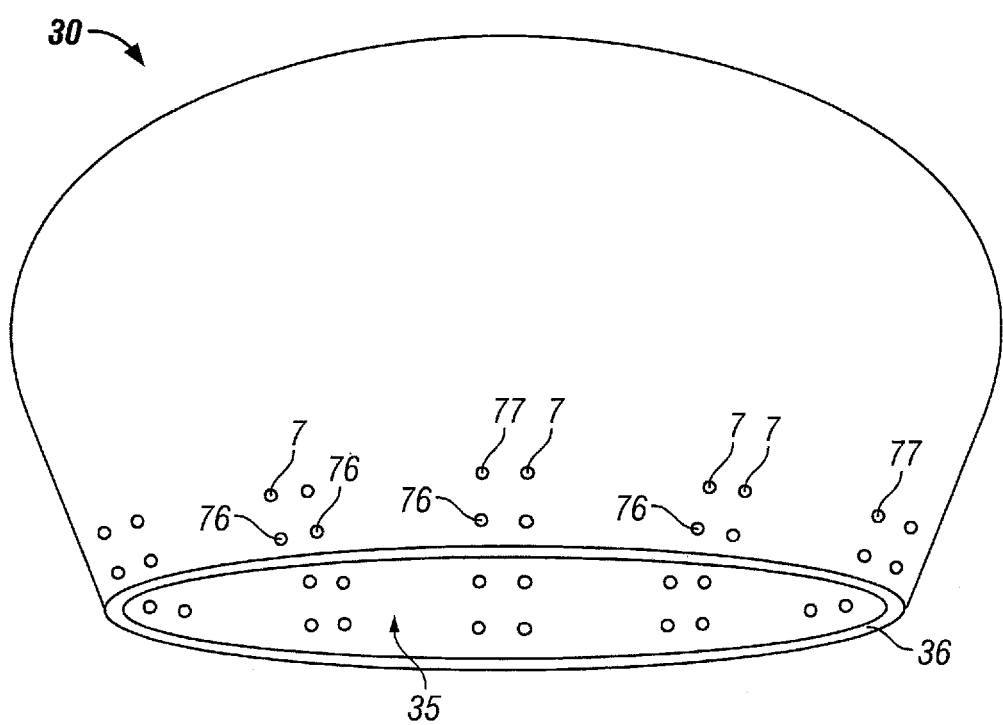
FIG. 13 is a pictorial view of a third embodiment of a prosthesis in accordance with the present invention similar to that in FIG. 5.

Reference is made to FIG. 13 which shows a third embodiment of a prosthesis 30 as in FIG. 5 but modified firstly so as to avoid the cut line and flaps and modified, secondly, to provide two sets of circumferentially extending eyelets 76 and 77 to receive one or more ligatures, not shown, in FIG. 13 but similar to that shown in FIG. 12. The prosthesis of FIG. 13 could be made from materials to be capable of being stretched over its coupling portion 38 for application onto the condyle.

Figure 14:
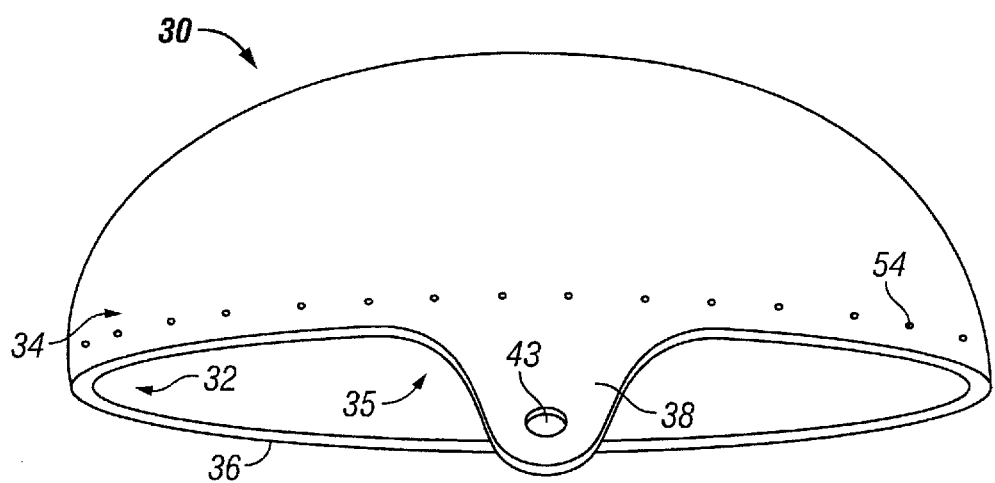
FIG. 14 is a pictorial view of a fourth embodiment of a prosthesis in accordance with the present invention.

Reference is made to FIG. 14 which shows a fourth embodiment of a prosthesis 30 which has its edge 36 about its opening 35 proximate the largest diameter circumference 54 of the prosthesis other than where a tab-like coupling portion 38 extends outwardly to overlie non-contiguous surfaces. A hole 43 through the coupling portion 38 is for coupling to the condyle as with a screw 45 in a manner similar to that shown in FIG. 11. The prosthesis 30 of FIG. 14 has a shape which permits it to merely be placed over the bulbous end 40 of the condyle 15.

Figure 15:
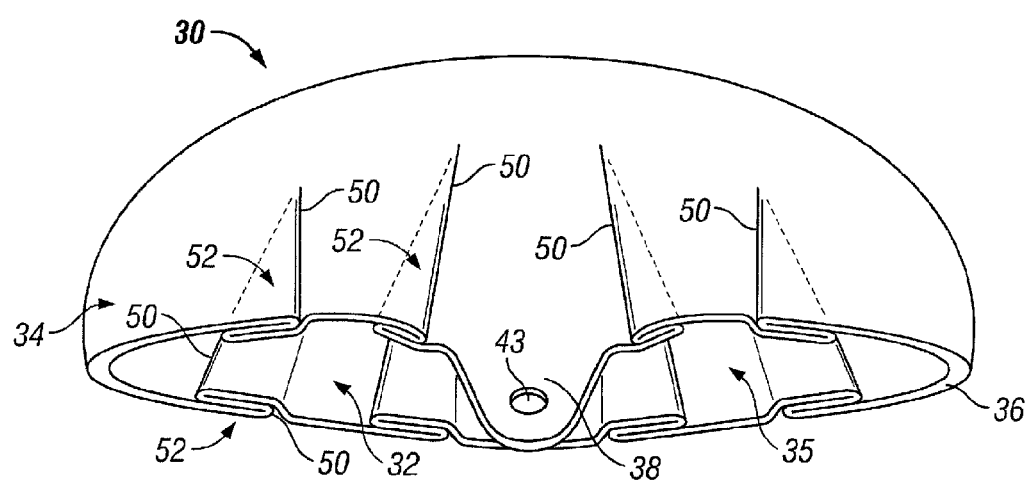
FIG. 15 is a pictorial view of a fifth embodiment of a prosthesis in accordance with the present invention.

Reference is made to FIG. 15 which illustrates a fifth embodiment of the prosthesis 30 substantially the same as the prosthesis shown in FIG. 14 but formed by a process in which a physical three-dimensional model is made of the condyle, placing a foil or sheet of metal over the model and conforming the foil or sheet to adopt the shape of the model. A thin sheet of metal as may be commercially available such as tantalum foil of thickness $2/1000^{th}$ of an inch may be manually placed over the model and conformed to the shape of the model preferably with fold lines or sharp edges minimized or avoided for the extent necessary substantially provided merely over non-contiguous surfaces. Excess portions of the sheet may be trimmed preferably leaving the coupling portions through which the opening is provided. Insofar as the foil or sheet cannot be stretched or deformed to adopt the desired shape, but must be folded, as with darts, then such folds as may be necessary are, as far as possible, arranged to occur over the non-contiguous surface of the mandibular 13 and the folds may be mechanically flattened to provide as uniform and smooth a surface as possible. In FIG. 15, a plurality of fold lines 50 for various spaced darts 52 are shown along the outward lateral sides of the prosthesis 30 which is to overlie at least in part the non-contiguous surface of the mandibular. The prosthesis of FIG. 15 has effectively a constant thickness between its inner surface 32 and outer surface 34 preferably at least where it is to overlie the articular cartilage centrally of the condyle where most of the forces are transferred.

FIG. 12 shows the use of a string-like ligature. Various other forms of ligatures may be utilized which may be separate elements from the element forming the prosthesis or may be integrally formed as part of the prosthesis. For example, the flaps 63 and 64 could have some form of interconnection such as hooks or slot members or, alternatively, ligatures could be formed as integral parts of the prosthesis about its outer end as like one or more circumferentially extending straps for engagement. Various ligatures and straps could be used. Additionally, after the prosthesis, for example, of FIG. 5 is located and placed in the closed position, the overlapping flaps could be secured together as by a mechanical device or bonding by cement or the like.

While the prosthesis is shown as adapted for extending over a single condyle, in various instances such like a knee in which two condyles are provided proximate each other, separate prosthesis could be provided for each condyle or, alternatively, a saddle-like prosthesis could be provided to cover both condyles.

Figure 16:
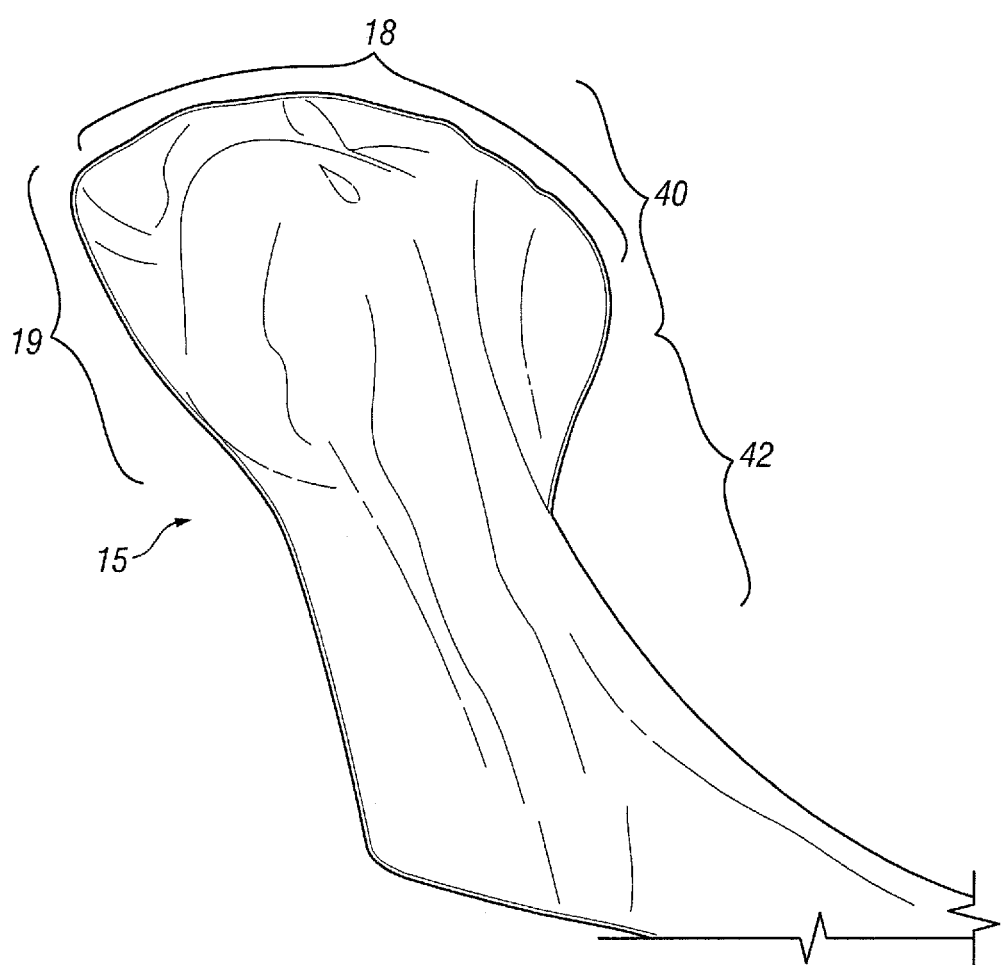
FIG. 16 is a pictorial view of a condyle of a temporomandibular joint.

Reference is made to FIGS. 16 to 23 which show a condyle 15 of the mandible from a TMJ joint and a prosthesis 30 in accordance with a sixth embodiment of the present invention as applied to the condyle 15 in successive steps shown in FIGS. 17 to 20. The condyle 15, as best seen in FIG. 16, has a bulbous end 40 joined to the remainder of the bone by a neck 42. The bulbous end 40 has portions with larger circumferences than portions of the neck 42. As also seen in FIG. 16, the condyle 15 includes an articular surface carrying articular cartilage 18 which is naturally of a generally rounded convex configuration. The condyle 15 also has non-contiguous surfaces 19 adjacent the contiguous bony surfaces carrying the articular cartilage 18.

Figure 17:
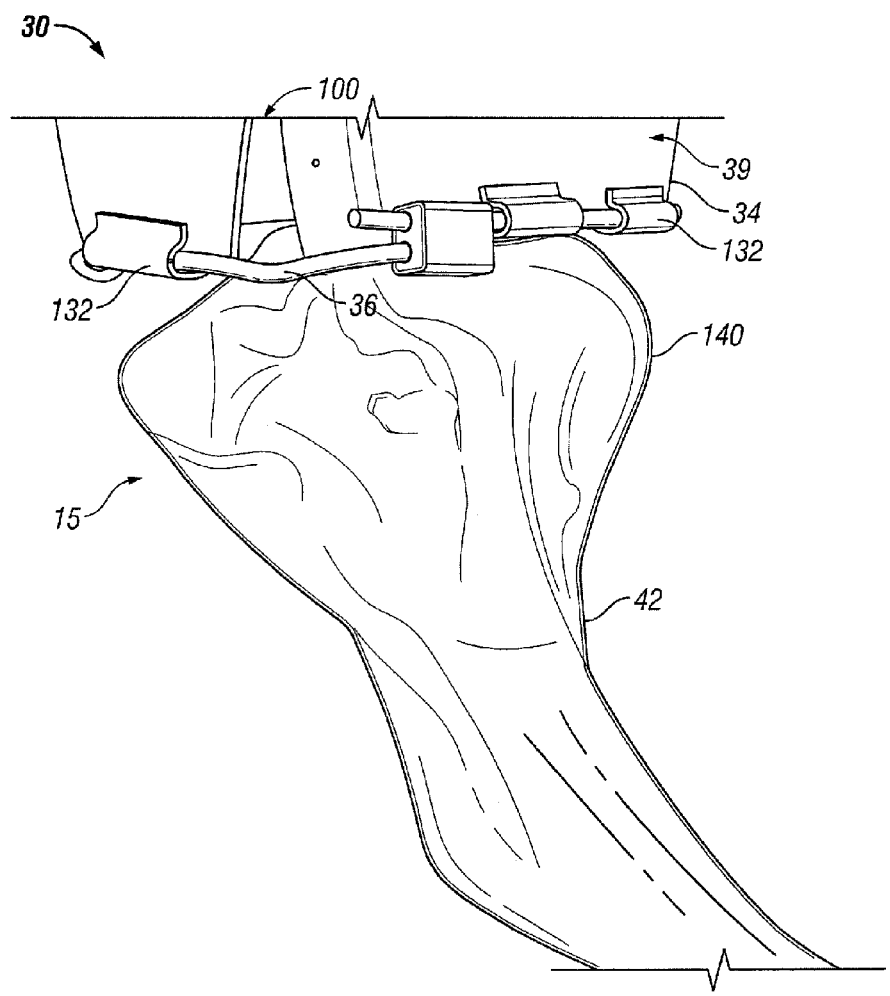
FIGS. 17 to 21 are pictorial views showing a sixth embodiment of a prosthesis in accordance with the present invention applied to the temporomandibular (TMJ) joint shown in FIG. 16 with FIGS. 17 to 20 showing a series of sequential steps of applying the prosthesis as seen from the same view and FIG. 21 showing a view of prosthesis applied to the joint as in FIGS. 19 and 20 but as seen from an opposite side.

The prosthesis 30 in accordance with the sixth embodiment of the present invention is partially shown in FIG. 17 and more fully shown in each of FIGS. 18 to 21. The prosthesis 30 comprises a thin sheet member 39 with an inner surface and an outer surface 34. The sheet member 39 has an interpositional sheath portion 37 adapted to overlie the outer surface of the articular cartilage 18 of the condyle 15. The sheet member 39 also has a coupling portion 38 extending away from the sheath portion 37 with the coupling portion 38 to overlie the non-contiguous surfaces 19 of the condyle 15 adjacent to the articular cartilage 18.

Figure 18:
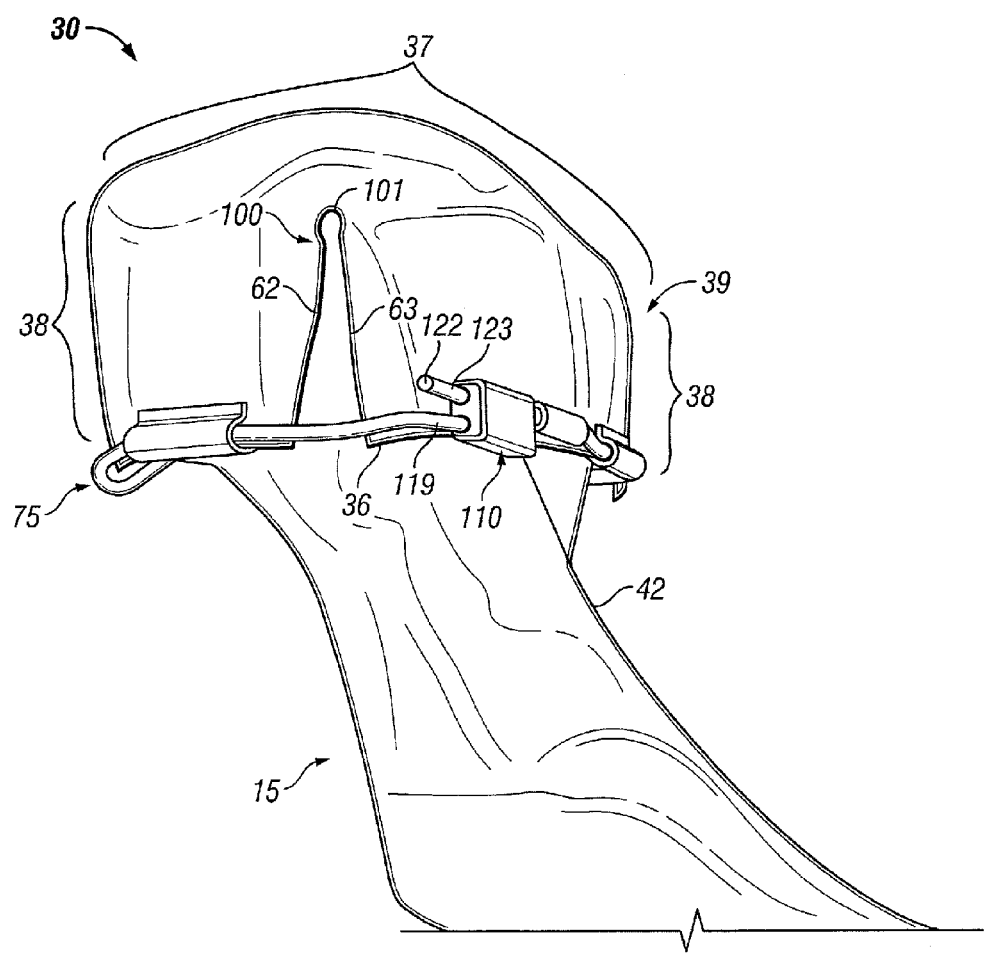

The sheet member 39 of the prosthesis 30 is pre-formed so as to have its inwardly directed surface over the contiguous bony surfaces carrying the articular cartilage 18 to substantially conform to the shape of the articular cartilage 18 of the condyle 15 onto which the prosthesis 30 is to be coupled. The sheath portion 37 effectively forms a continuous dome to overlie the outer surface of the articular cartilage 18 of the condyle 15. The coupling portion 38 bridges from the sheath portion 37 extending from the sheath portion 37 to overlie the non-contiguous surfaces 19 of the condyle adjacent to the articular cartilage 18 thereof and about the reduced circumference neck 42. A keyhole slotway 100 as seen in FIGS. 17 to 20 is provided through the sheet member 39 having a keyhole-like shape and defining two opposed cut edges 62 and 63 which merge at a keyhole blind end 101 having a truncated circular periphery. The blind end 101 is in the shape of a circular keyhole with each of the cut edges 62 and 63 merging with the keyhole blind end 101 at circumferentially spaced locations. The prosthesis 30 is shown in FIGS. 17 and 18 in an open condition as the prosthesis is being moved to become applied over the condyle 15. The prosthesis 30 is preferably pre-formed to have a configuration as shown in FIGS. 17 and 18 with one or more of the keyhole slotways 100. In FIGS. 17 and 18, each of the two cut edges 62 and 62 diverge away from each other as they extend outwardly from the keyhole blind end 101 such that, as seen in FIGS. 17 and 18, the two cut edges 62 and 63 are closer together proximate the keyhole blind end 101 and farther apart proximate the outer edge 36 of the sheet member 39.

Figure 22:
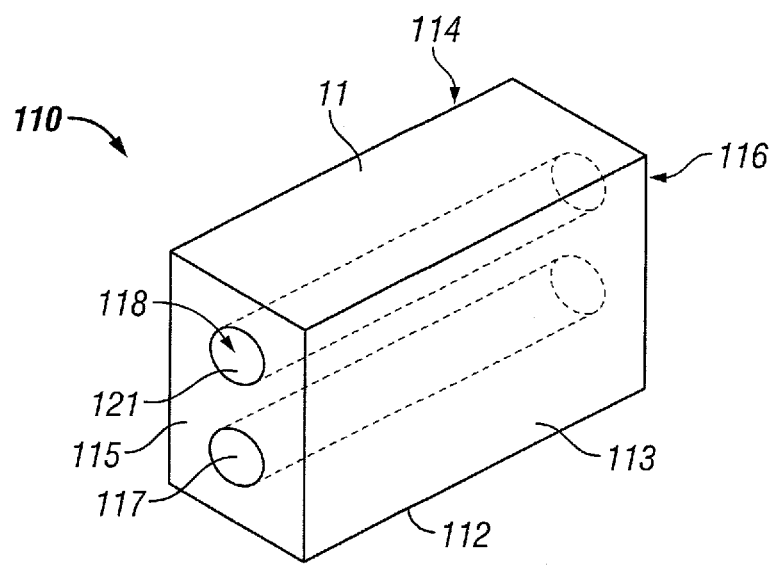
FIG. 22 is a first perspective end view of a clasp forming part of the prosthesis shown in FIGS. 17 to 21.
Figure 23:
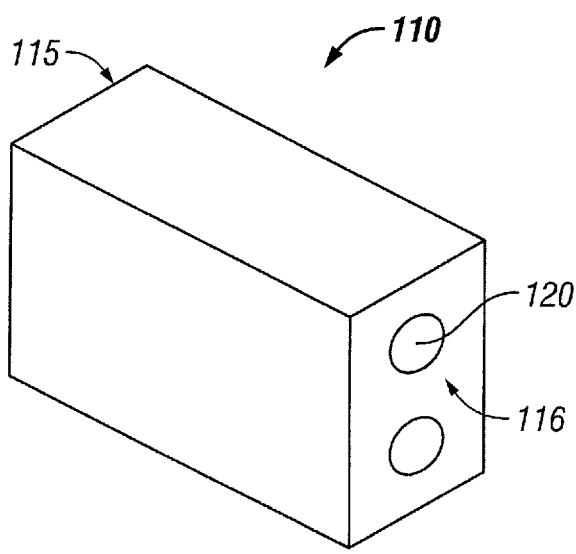
FIG. 23 is a second perspective end view of the opposite end of clasp shown in FIG. 22.

A circumferential ligature 75 is shown in FIG. 18 as an elongate member of constant preferably circular cross-section engaging a clasp member 110. The clasp member 110 is shown as seen in FIGS. 22 and 23 as having a top 111 and a bottom 112, a front 113, a rear 114 and two ends 115 and 116. Two passageways 117 and 118 extend from the first end 115 to the second end 116. One lower passageway 117 is shown as being generally cylindrical and in which a first end 119 of the ligature 75 is fixedly secured as, for example, by being welded or bonded therein. The upper passageway 118 is shown to extend parallel to the lower passageway but as having an opening 120 at the second end 116 which is smaller than the opening 121 at the first end 115. The smaller opening 120 at the second end 116 is sized so as to permit the ligature 75 to pass therethrough yet to frictionally engage the ligature 75. The ligature 75 is adapted to have an end portion 123 proximate a second distal end 122 extend out through the upper passageway 118 in the clasp entering at the second end 116 and accessible for engagement by a user at the first end 115. The end portion 123 of the ligature 75 is adapted for engagement so that the ligature may be drawn through the upper passageway 118 on the clasp out of the larger opening 121. As the ligature 75 is drawn through the clasp, progressing from the smaller opening 120 towards the larger opening 121, the ligature 75 is clamped in the smaller opening 121 in the manner which prevents the ligature 75 from moving relative the clasp 110 in a direction from the larger opening 121 to the smaller opening 120. Thus, the engagement between the upper passageway 118 and the ligature 75 effectively provides for one-way movement of the ligature 75 from an untightened position as shown, for example, in FIG. 18 to a tightened position as shown, for example, in FIGS. 19 to 20. The ligature is tightened about the condyle neck to assume a reduced circumference and the clasp operates to resist the ligature assuming an enlarged circumference and becoming loosened about the neck.

With tightening of the ligature 75 so as to reduce the circumferential extent of the ligature, the cut edges 62 and 63 about each keyhole slotway 100 are drawn towards each other to assist in engaging the prosthesis about the neck 42 of the condyle 15 against removal. As seen in each of FIGS. 19, 20 and 21, once secured on the condyle, the sheet member 39 does not overlap itself, that is, the two cut edges 62 and 63 are shown to remain spaced from each other by a gap 610, however, it is to be appreciated that the two edges 62 and 63 may abut each other without overlapping. The desired result is to avoid overlap of the sheet member at the edges 62 and 63 such that the relative thickness of the sheet member 39 from the condyle 15 will not abruptly change.

Preferably, in accordance with the present invention, the blind keyhole slotways 100 and any gap 610 which is provided between the two cut edges 62 and 63 are provided over the non-contiguous surface 19 rather than over the articular cartilage 18.

The configuration of the keyhole slotways 100 in a pre-formed prosthesis before application onto the condyle, and preferably the number, location and size of these keyhole slotways 100 are selected so as to assist in distributing stresses which may be developed at the inner blind end 101 of each slotway so as to assist the sheet member 39 in accepting localized forces applied at the inner blind end 101 of the slotway 100 as when forming the prosthesis and when there may be deformation and flexure of the prosthesis as in applying and securing the prosthesis over the condyle, and in use of the joint. Each keyhole slotway arrangement, for example, assists in preventing the sheet member from tearing at the junction between edges 62 and 63.

Figure 19:
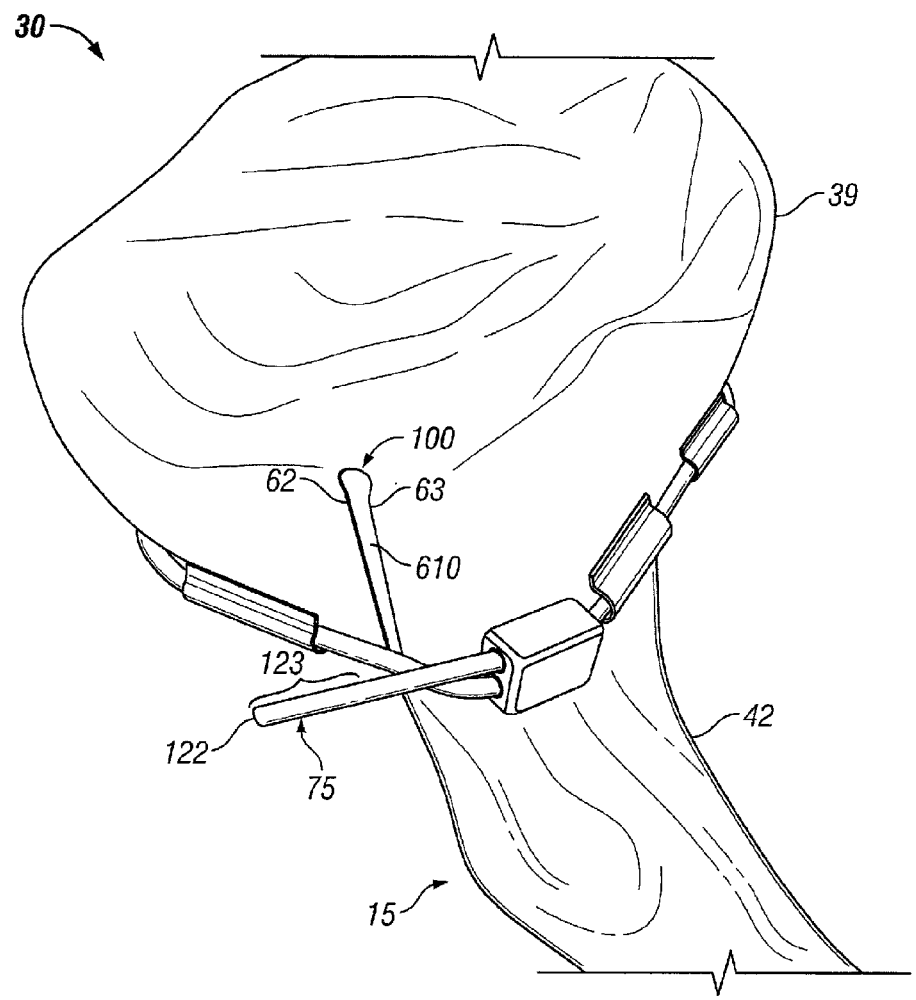
Figure 20:
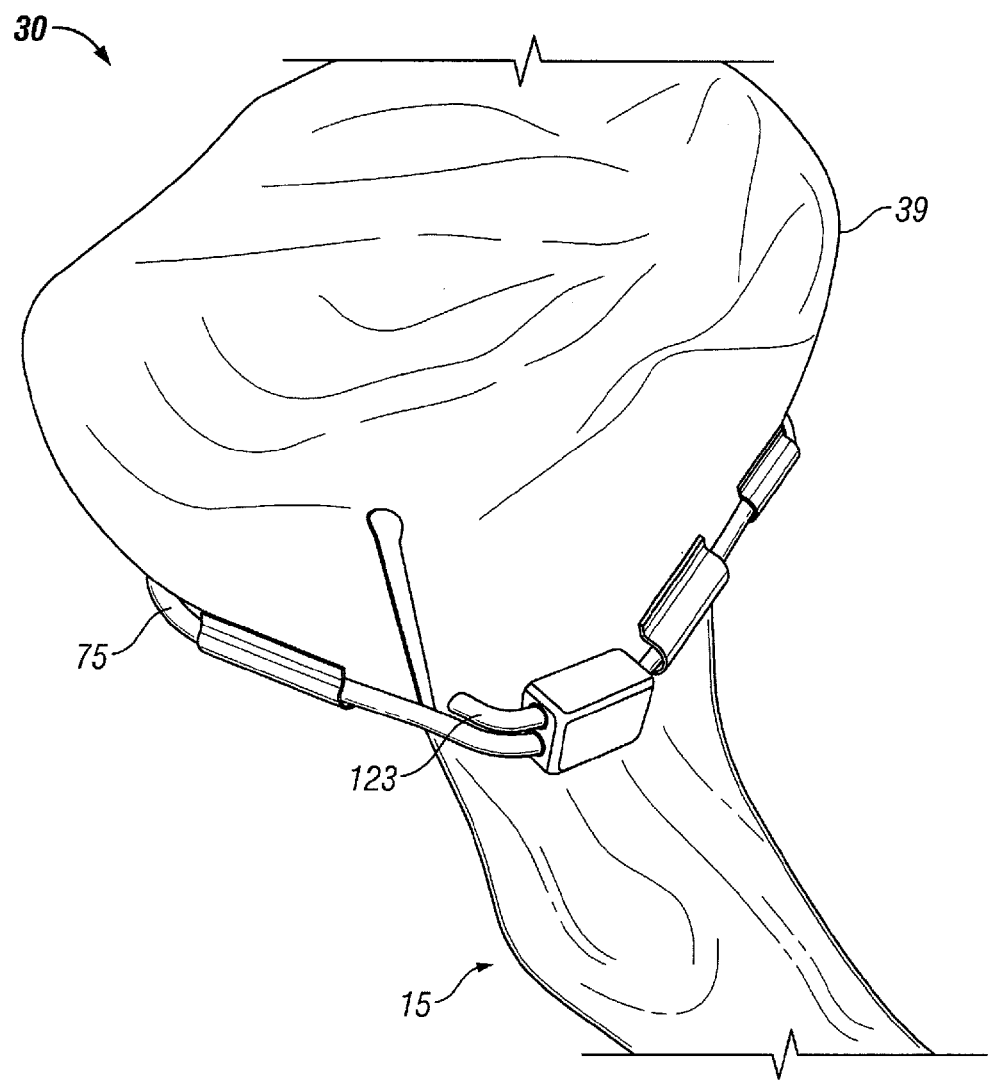
Figure 21:
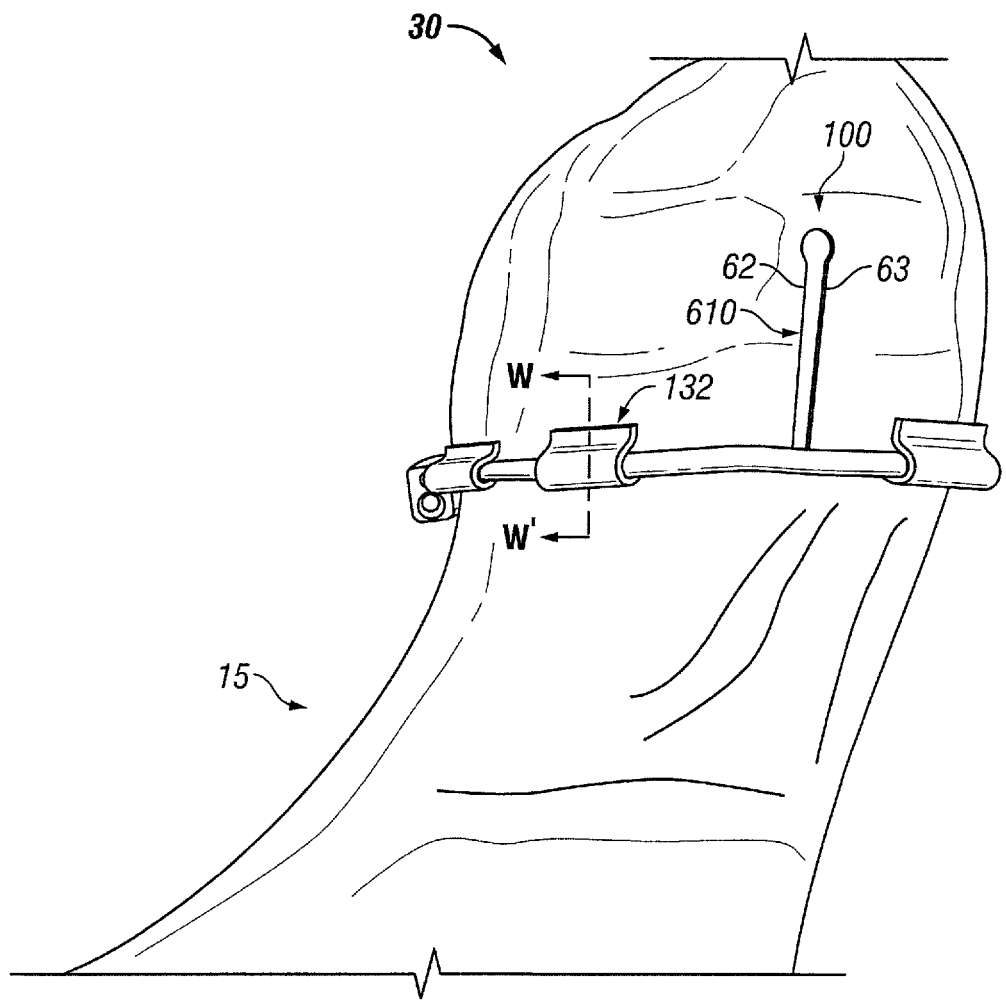

The sixth preferred embodiment of the prosthesis illustrated in FIGS. 17 to 21 is shown to have two keyhole slotways 100. A first keyhole slotway 100 as seen in FIGS. 17 to 20 and a second keyhole slotway 100 on an opposite side of the prosthesis as seen in FIG. 21. The number of keyhole slotways may be selected having regard to the nature of the bone about which the prosthesis 30 may be provided. Merely one keyhole slotway may be provided, however, a plurality of keyhole slots such as 2, 3, 4, 5 or other number of slotways may be provided. Each of the keyhole slotways 100 and its keyhole blind end 101 preferably overlies the non-contiguous surface 19, however, this is not strictly necessary and one or more keyhole slotways 100 could overlie a portion of the articular cartilage 18.

The preferred embodiment of the clasp 110 as best shown in FIGS. 22 and 23 is but one form of an arrangement to permit in use a person applying the prosthesis to easily reduce and maintain the circumferential extent of a ligature 75. Various other clasps or other circumferential ligatures may be utilized.

In the drawings, FIG. 18 illustrates a condition that the prosthesis 30 has merely been applied over the condyle with a circumferential ligature 75 having an enlarged circumferential extent. FIGS. 19, 20 and 21 illustrate conditions in which the circumferential ligature has had its circumferential extent reduced. FIG. 19 illustrates a condition that the circumferential ligature 75 has had its circumference reduced by drawing the end portion 123 of the circumferential ligature carrying the second distal 122 through the clasp. FIG. 20 illustrates a condition that the end portion 123 of the circumferential at the ligature has been cut and pushed to be closer to the condyle adjacent to the sheet member 39.

Figure 24:
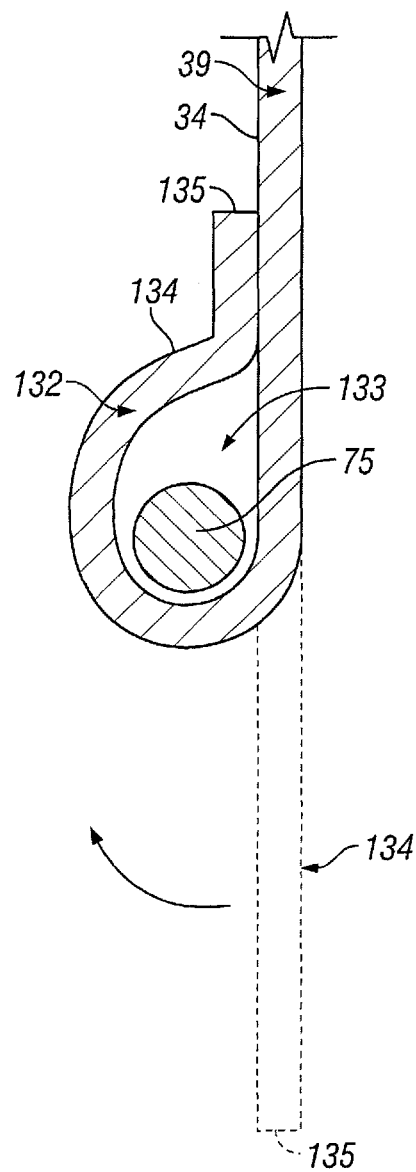
FIG. 24 is a cross-sectional side view of the prosthesis along section line W-W' in FIG. 21.

As seen in FIGS. 17 to 21 along the outer edge 36 of the sheet member 39, a number of loop members 132 are provided with circumferentially extending openings therethrough through which the ligature 75 extends and within which the ligature 75 is slidable. One loop member 132 is shown in cross-sectional in FIG. 24 as comprising a rectangular tab 134 which extends from the outer edge and is folded outwardly and upwardly to overlie the sheet member 39 of the coupling portion 38 with a distal end 135 welded to the outside surface 34 of the sheet member 39 to form the opening 133 through the loop member. When the ligature 75 is tightened preferably the gaps 610 between the edges 62 and 63 of the keyhole slotways 100 are small and the ligature 75, either engages the loop members 132 or the outside surface 34 of the sheet member 39 so that the ligature 75 effectively does not engage the condyle.

In the preferred embodiment illustrated in FIGS. 17 to 21, each of the sheet member 39, the ligature 75 and clasp 110 may preferably be formed from metal such as, for example, preferably tantalum. The invention is, however, not limited to the sheet, the ligature or the clasp being formed from metal.

As seen in FIG. 18 a keyhole slotway 100 is provided which is to have its edges 62 and 63 drawn together by use of the ligature 75 which extends entirely about the circumference of the neck of the bone. An alternate ligature could be used which extends merely circumferentially over only a segment of the circumference as, for example, merely over any slotways that may be provided. A separate ligature could be provided to merely span the gap of each slotway, either as a separate element or as an integral part of the sheet member 39.

Reference is made to FIGS. 26 to 27 illustrating a seventh embodiment of a prosthesis 30 in accordance with the present invention as applied over a condyle 15.

As seen in a comparison of FIGS. 25, 26 and 27, the condyle 15 is bulbous, however, with a bulbous projection 140 projecting merely from one side of the condyle 15, that is, protruding at a side indicated as 142 and not being protuberant on the opposite side 144, the front 146 and the rear 148. To maintain the prosthesis 30 about the condyle 15, the prosthesis carries (a) over the bulbous protruding side 142 a coupling portion 38 which extends to underneath the bulbous projection 140, and (b) over the side 144 of the condyle opposite the bulbous protruding side 142 with a coupling portion 38. A surgical fastener such as surgical screw 45 is shown extending through a hole 43 in the coupling portion 38 over the side 144 to prevent removal of the prosthesis from engagement on the condyle. For application, the prosthesis 38 is to be manipulated to have the coupling portion 38 on the side 142 engaged underneath the bulbous projection 140 and then be pivoted to have the coupling portion 38 slide down over the other side 144 whereupon the prosthesis is secured to the condyle with the screw 45. This an arrangement assists in maintaining the prosthesis on the condyle where merely relying on the engagement of the coupling portions 38 about reduced neck portions of the condyle shown might not be effective.

Figure 28:
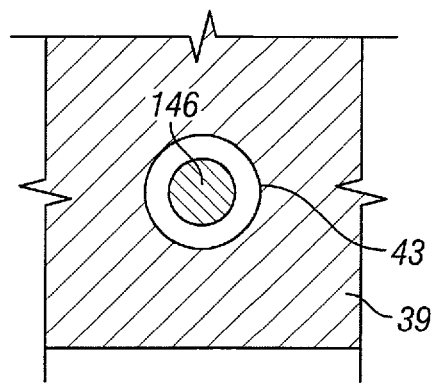
FIG. 28 is a cross-sectional side view along section line Z-Z' in FIG. 27.

As best seen in FIG. 28, the hole 43 through the sheet member 39 through which the shank 146 of the screw 49 is to pass is preferably is of a shape and size which permits relative movement of the sheet member 39 on the condyle 15 about the shank 146 of the screw as is advantageous to permit relative movement of the prosthesis 30 on the condyle 15.

Figure 29:
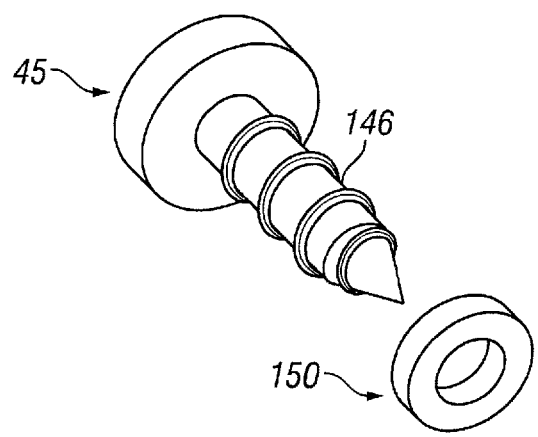
FIG. 29 is an exploded pictorial view showing a screw as shown in FIGS. 25 to 27, however, with an optional resilient washer.

FIG. 29 illustrates in schematic pictorial view the screw 45 shown in FIGS. 25 to 27 and also shows a resilient washer 150 which is adapted to be engaged about the shank 146 of the screw and secured within the hole 43 of the sheet. The resilient washer 150 may be deformed to permit relative movement of the sheet 39 to the screw 49 with deforming of the resilient washer. The resilient washer 150 has an inherent bias to assume an initial configuration which inherent bias provides forces attempting to return the prosthesis 30 to a desired initial position relative the screw shank 146.

Figure 30:
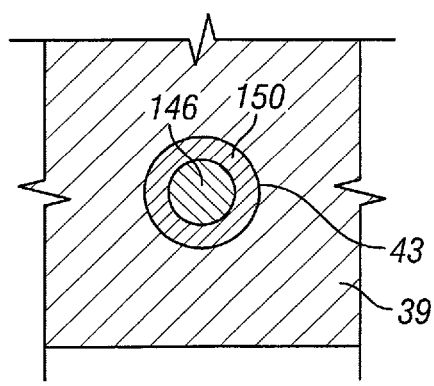
FIG. 30 illustrates a cross-section similar to FIG. 28, however, showing the prosthesis as applied with the washer shown in FIG. 29 disposed intermediate the shank of the screw and the opening in the prosthesis.
Figure 31:
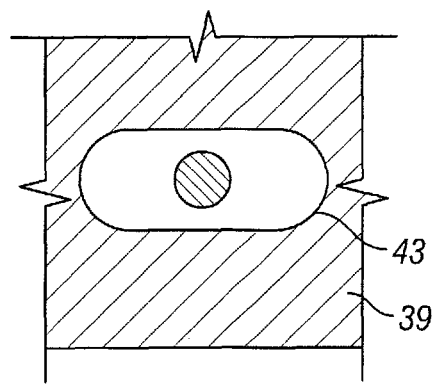
FIGS. 31, 32 and 33 are views the same as FIG. 28 but showing different openings through the prosthesis.
Figure 32:
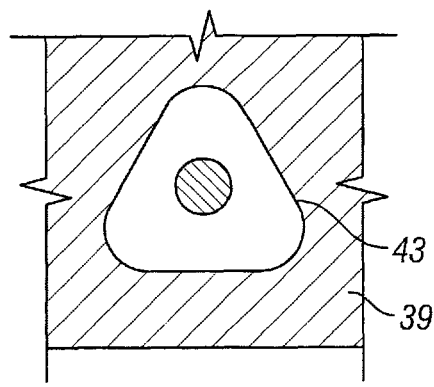
Figure 33:
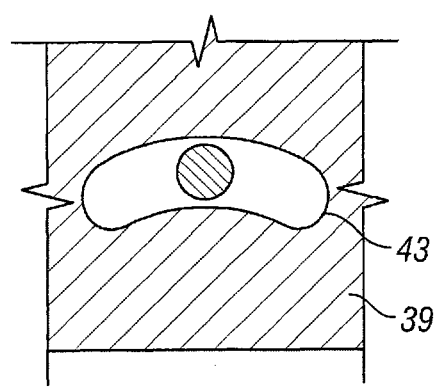

FIGS. 28 and 30 show the hole 43 through the sheet as being circular. This is not necessary. The hole may be provided with different shapes. For example, FIGS. 31, 32 and 33 provide views similar to FIG. 28 showing different configurations for the hole 43 which will serve the purpose of selectively limiting the relative range of movement of the sheet 30 relative to the screw 49 to preferred ranges. In the case of FIG. 31, the hole 43 is an elongate slot of constant width. In the case of FIG. 32, the hole 43 is triangular and in the case of FIG. 33, the hole 43 is an arcuate slot. If desired, suitably shaped resilient washers may be provided about the screw shank in the embodiments of FIGS. 31 to 33 which may partially or fully fill the hole 43 and suitably bias the screw 45 to assume preferred position or positions.

Figure 38:
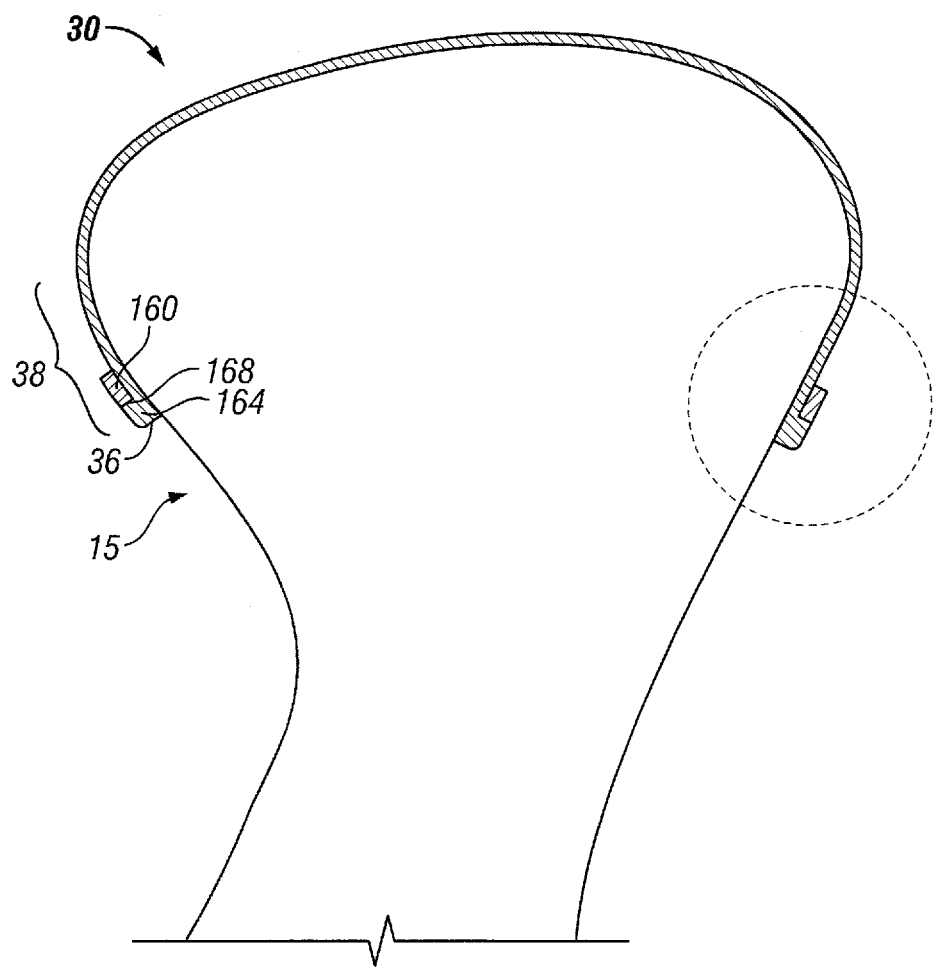
FIG. 38 is a cross-sectional side view similar to FIG. 9 but showing a prosthesis in accordance with an eighth embodiment of the present invention as secured to a condyle with a ring as shown in FIG. 36.
Figure 39:
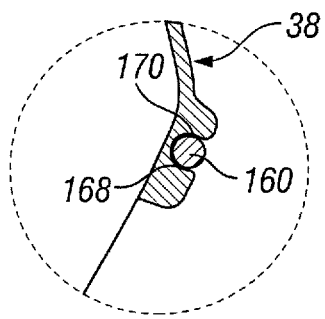
FIG. 39 is a partial cross-sectional side view similar to a portion of FIG. 39 within the broken line circle but showing a prosthesis in accordance with a ninth embodiment of the present invention as secured to a condyle with a ring as shown in FIG. 34.

The nature of the ligatures for use in accordance with the present invention is not limited. The ligatures may be elastic. For example, the ligature 75 illustrated in FIGS. 17 to 21 may comprise an elastic material which, when drawn through the clasp would, due to the inherent elasticity of the ligature, assist in maintaining the circumferential extent of the ligature reduced. The ligature 75 illustrated in FIGS. 17 to 21 could be replaced by ligatures as shown in FIGS. 34 and 36 each of which is an annular ring 160. The ring 160 may have, for example, a circular cross-section as seen in FIG. 35 or a rectangular cross-section as seen in FIG. 37. Various arrangements may be provided for elastomeric ligatures as shown in FIGS. 34 and 36 to engage the coupling portions 38 of the prosthesis. The elastomeric ring ligatures as shown, for example, in FIGS. 34 and 36 could be used in a manner that the prosthesis 30 is first applied over the condyle and then the ring is applied over at least some axially spaced coupling portions 38 preferably about a reduced circumference portion of a neck of a condyle. Various arrangements may be provided to assist the elastomeric ring ligature remaining engaged about desired portions of the coupling portions 38. For example, as seen in FIG. 38, at the end edge 36 of the coupling portion 38 is provided with an enlarged thickness stop portion 164 on its outside at least at circumferentially spaced locations so as to provide an upwardly directed shoulder 168 to engage a resilient ring 160 such as shown in FIG. 36 disposed about a reduced neck of a bulbous condyle, and retaining the ring 160 between the upwardly directed shoulder 168 and the enlarged portions of the bulbous condyle. Rather than merely provide an upwardly directed shoulder 160, as seen in FIG. 39 the coupling portions 38 could be provided with a suitable groove to receive a resilient ring 160 as shown in FIG. 34 between a lower upwardly directed shoulder 168 and a spaced downwardly directed shoulder 170.

Figure 40:
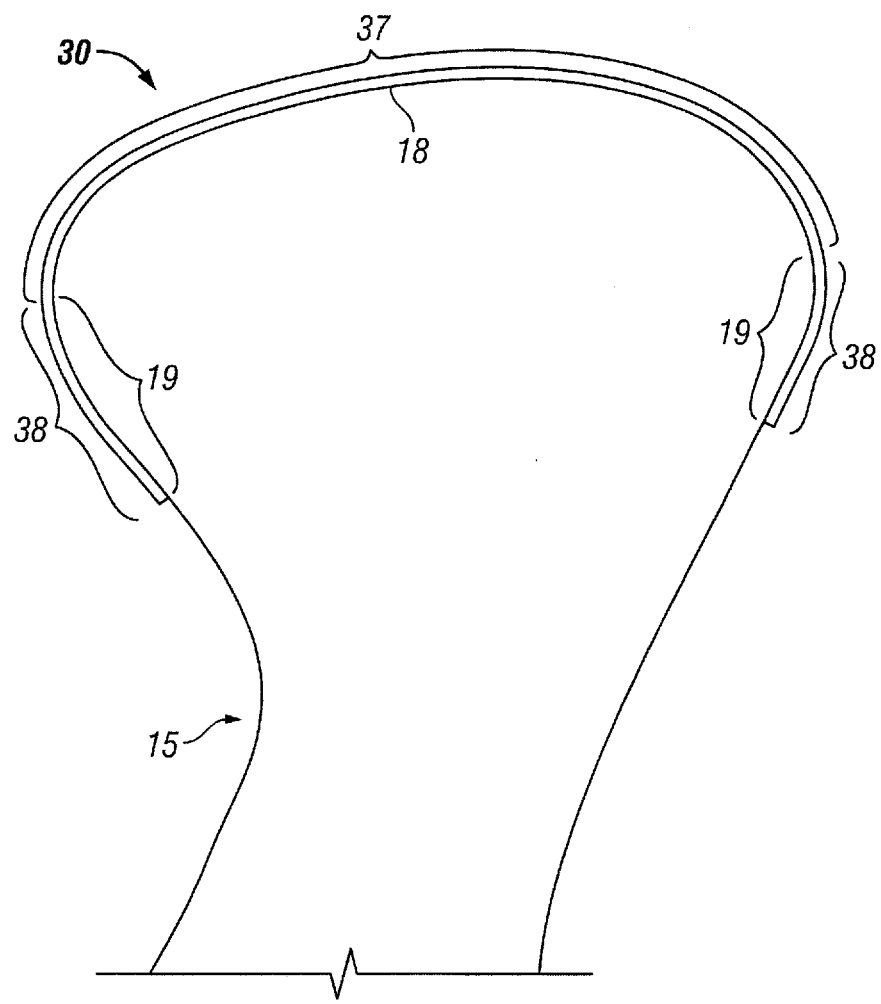
FIG. 40 is a partial cross-sectional side view similar to a portion of FIG. 39 but showing a prosthesis in accordance with a tenth embodiment of the present invention.
Figure 41:
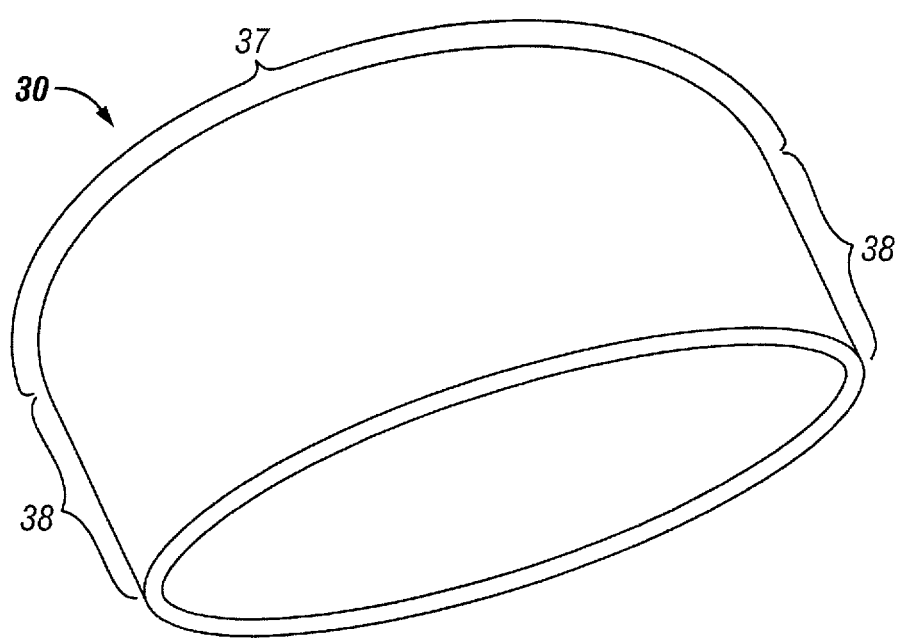
FIG. 41 is pictorial view of the prosthesis shown in FIG. 39 in an expanded configuration.

Reference is made to FIG. 40 which illustrates a prosthesis 30 in accordance with the tenth embodiment to the present invention disposed about a bulbous condyle 15. The prosthesis 30 in FIG. 40 has as its coupling portion 38 an annular tubular member which can be expanded circumferentially, for example, to assume an expanded configuration illustrated in FIG. 41 with the tubular member being able to have its diameter expanded from its edge 36 to the cap-like interpositional sheath portion 37 which is to overlie the articular surface 18 of the condyle 15. After being expanded and applied over the condyle, the tubular annular outer portion 38 is contracted to assume a configuration of reduced circumference about the neck of the condyle. Preferably, the tubular annular outer portion 38 is resilient and has an inherent bias to assume a configuration of reduced circumference but may be resiliently expanded at least circumferentially and when released will return to its inherent configuration of reduced circumference. Such a resilient tubular annular outer portion 38 may also be resilient in axial direction so as to assist in ensuring that the cap-like interpositional sheath portion 37 is free to at least some limited relative movement on the condyle. An arrangement as illustrated in FIGS. 40 and 41 could be accomplished, for example, by providing the sheet member over the interpositional sheath portion 37 to comprise a central sheet of polymer, preferably with metal covering at least one of its inside surface and outside surface and with the central sheet of polymer at a transition between the interpositional sheath portion 37 and the outer portion 38 merging into and being coupled to a sock-like tubular elastic sleeve forming the tubular annular outer portion 38. The elastic sleeve could have, for example, a mesh of crossing overlapping helically arranged elastomeric strands bonded together which sleeve may or may not have its inner or outer surfaces coated in part or whole with metal.

Figure 42:
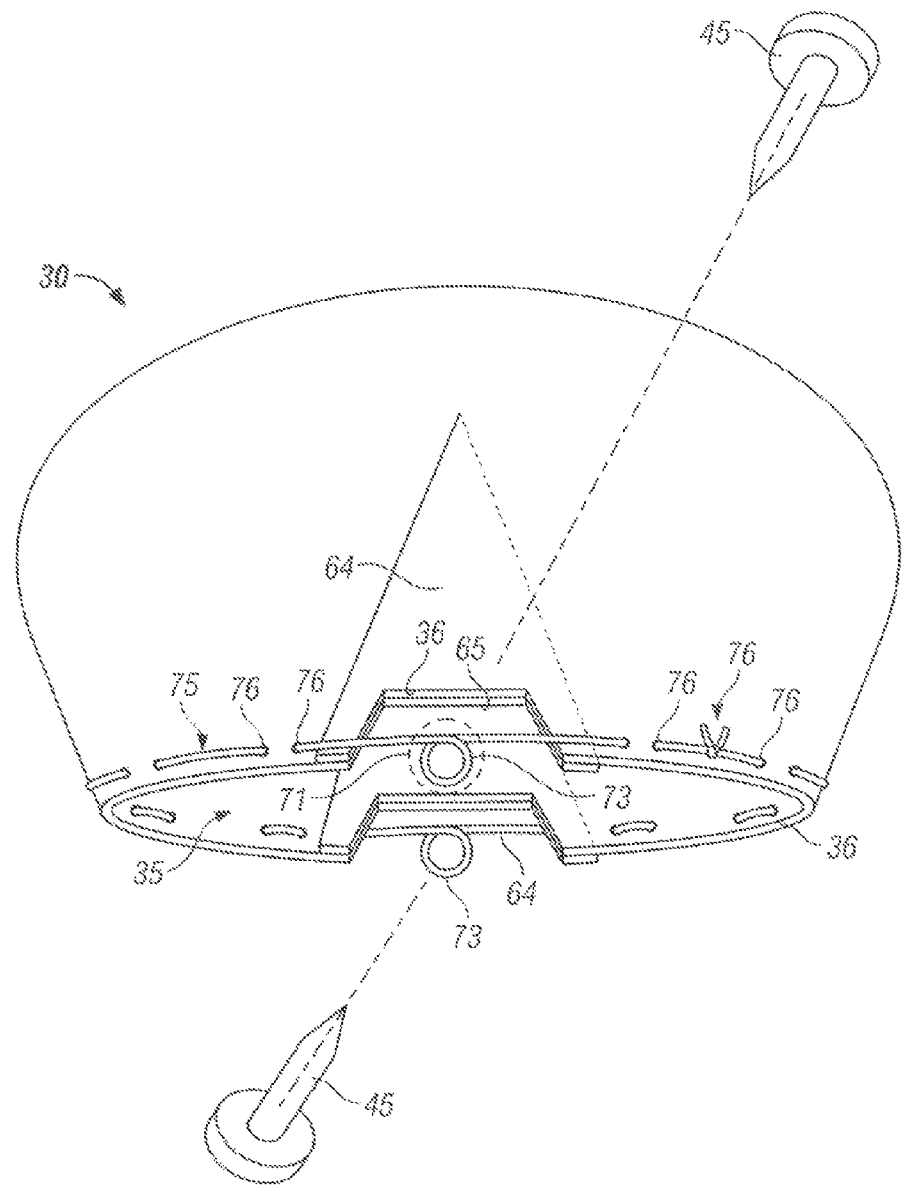
FIG. 42 is a schematic pictorial view of a prosthesis in accordance with an eleventh embodiment of the present invention.
Figure 43:
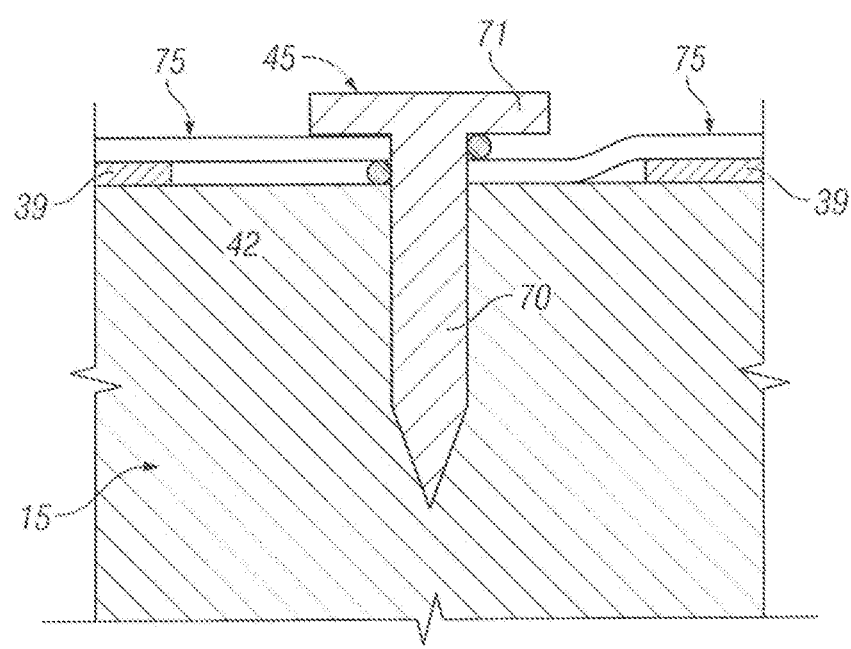
FIG. 43 is a partial cross-sectional side view showing a circumferential ligature of the prosthesis of FIG. 42 coupled to an underlying condyle.

Reference is made to FIGS. 42 and 43 which show an eleventh embodiment of a prosthesis in accordance with the present invention. The prosthesis shown in FIG. 42 is identical to the prosthesis shown in FIG. 12 with three exceptions. Firstly, the circumferential ligature 75 is shown as being provided with two loops 73. Secondly, a pair of fasteners in the form of screws 45 are provided such that as seen in FIG. 43, the screws may be secured into the condyle 15 about which the prosthesis 30 is disposed with the loops 73 of the ligature 75 extending circumferentially about the shaft 70 of the screw 45. Thirdly, the sheet member 39 is cut away from the prosthesis 30 on areas of the prosthesis proximate to the loops 43. In FIG. 42, each of the flaps 64 and 65 has a portion cut away and removed from the edge 36 inwardly such that, as may be seen in FIG. 43, a head 71 of a screw 45 when engaged through the loop 73 of the ligature 75 is spaced from the edge 36 of the prosthesis. A head 71 of one screw is illustrated schematically in dashed lines circumferentially about one of the loops 73 as in a position the head 71 of the screw would assume when the screw is engaged in the condyle 15. As seen in FIG. 43, the loop 73 of the ligature 75 wraps circumferentially about the shaft 470 of the screw 45 with the loop 73 of the ligature 75 received in an annular space underneath the screw head 71 between the screw head 71 and the condyle 15 about the shank 70.

In use, the prosthesis 30 is placed about the condyle 15, each of the two screws 45 may be threaded into the condyle 15 at suitable locations and then the ligature 75 may be manually looped about the shaft of the screw 45. Alternatively, the loops 73 may be pre-formed before the screws are secured into the condyle 15.

A purpose of the arrangement illustrated in FIGS. 42 and 43 is to couple the prosthesis 30 on the condyle 15 permitting the prosthesis 30 to move freely on the condyle 15 yet to constrain such movement particularly to limit rotation of the opening of the prosthesis 30 about the neck of the condyle 15. In the preferred arrangement as illustrated in FIGS. 42 and 43, each loop 73 extends away from the edge 36 of the prosthesis 30 relative to portions of the ligature 75 that extends circumferentially. In the embodiment of FIG. 42, the loops 73 and the ligature 75 are shown as being located below the edge 36 of the sheet member 39 as is preferred by removing and cutting away portions of the sheet member 39 proximate the desired locations of the screws so as to effectively move the edge inwardly from the loop 73. Alternately, so as to avoid cutting away portions of the sheet member 39, a screw 45 may be provided spaced sufficiently away from the edge 36 that the screw 45 does not have its head 71 overlie the sheet member 39. In the embodiment of FIG. 42, the screws are shown at a circumferential location proximate the flaps 64 and 65. This is not necessary and the screws may be provided at any circumferential portion of the ligature as, for example, spaced circumferentially from the location of the flaps 64 and 65. The embodiment illustrated in FIG. 42 shows two loops 73 in the circumferential ligature as secured by two screws 45. Merely one such screw 45 and one loop 73 need be provided and, as well, three or more such loops and screws may be provided at circumferentially spaced locations about the opening. Preferably, the loops and corresponding screws are provided at locations which minimize any interference of the loops and screws with the movement of the prosthesis 30 on the condyle 15 in the normal functioning of the joint.

In the embodiment of FIG. 42, the circumferential ligature 75 is shown as extending relatively straight annularly about the opening of the prosthesis 30. The relative tension of the ligature 75 can be selected so as to affect the extent to which the prosthesis 30 may relatively move on the condyle 15. Insofar as the ligature 75 may be relatively stiff as, for example, a metal wire, then the provision of a loop 73 in itself resists movement of the loop 73 effectively circumferentially relative to the remainder of the ligature 75.

Figure 44:
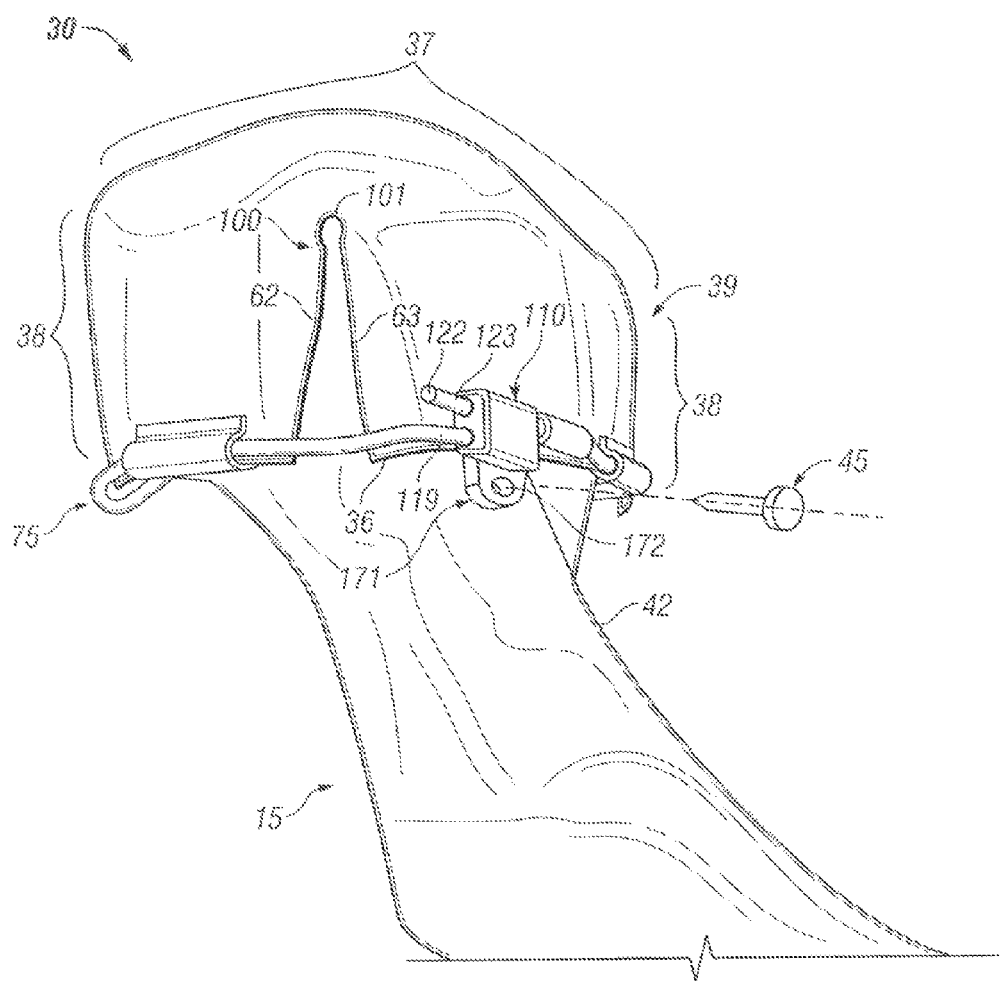
FIG. 44 is a pictorial view of a twelfth embodiment of a prosthesis in accordance with the present invention applied to the temporomandibular (TMJ) joint shown in FIG. 16, similar to FIG. 18, however, with a modified clasp.
Figure 45:
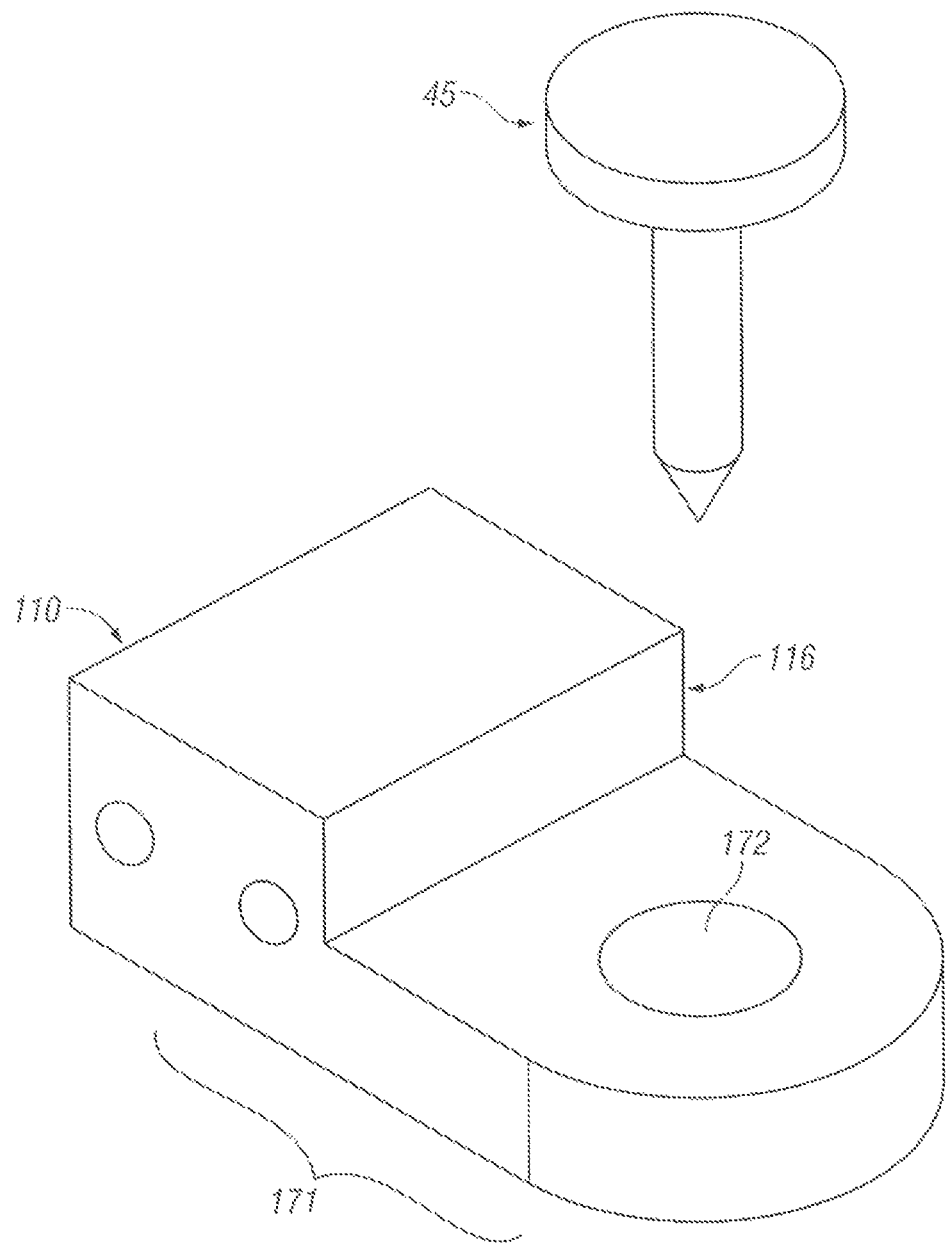
FIG. 45 is a perspective view of the clasp forming part of the prosthesis shown in FIG. 44.
Figure 46:
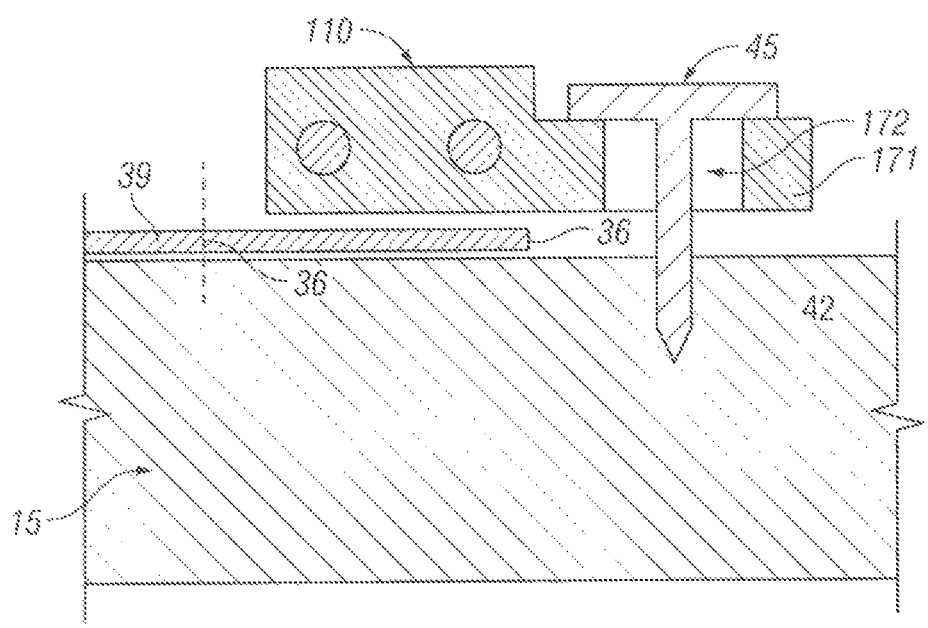
FIG. 46 is a partial cross-sectional side view through FIG. 44 showing the clasp as applied to the condyle.

Reference is made to FIGS. 44, 45 and 46 which show a twelfth embodiment of a prosthesis in accordance with the present invention. The prosthesis 30 shown in FIG. 44 is identical to that shown in FIG. 18 with the first exception that the clasp member 110 includes a coupling tab 171 integrally formed therewith with an opening 172 therethrough and the second exception that a screw 45 is provided to couple the coupling tab 171 to the condyle 15. The fastening tab 171 extends from the clasp member 110 away from the prosthesis 30 so as to position the fastening tab and particularly the opening 172 over a preferably non-contiguous surface 19 of the condyle 15. The screw 45 has a shank 70 and a head 71. The screw 45 extends through the opening 172 to secure the clasp member 110 to the condyle 15 against removal. As seen in side view in FIG. 46, preferably the opening 172 is larger than the diameter of the shank 70 of the screw 45 so as to permit limited relative movement of the clasp member 110 and hence the prosthesis 30 relative to the condyle 15. As seen in FIG. 46, the head 71 of the screw is larger than the opening 172. The screw 45 is engaged into the condyle 15 in a manner so as to permit the clasp member 110 to move axially relative to the shaft 70 and avoid forcing the clasp member 110 down onto the sheet member 39 in a manner which might pinch the sheet member 39 and prevent the sheet member 39 from being mobile relative to the condyle 15. In the embodiment illustrated in FIGS. 44 to 46, avoidance of pinching of the sheet member 39 underneath the clasp member 110 can be accomplished by providing for a cut-out of the sheet member 39 underneath areas which the clasp member 110 is to overlie. Thus, for example, as seen in FIG. 46, in a similar manner to that shown in FIG. 42, the sheet member 39 may be cut-away as, for example, seen in FIG. 46 to move the edge 36 from its position shown in a solid line to a position shown in a dashed line in FIG. 46.

Figure 47:
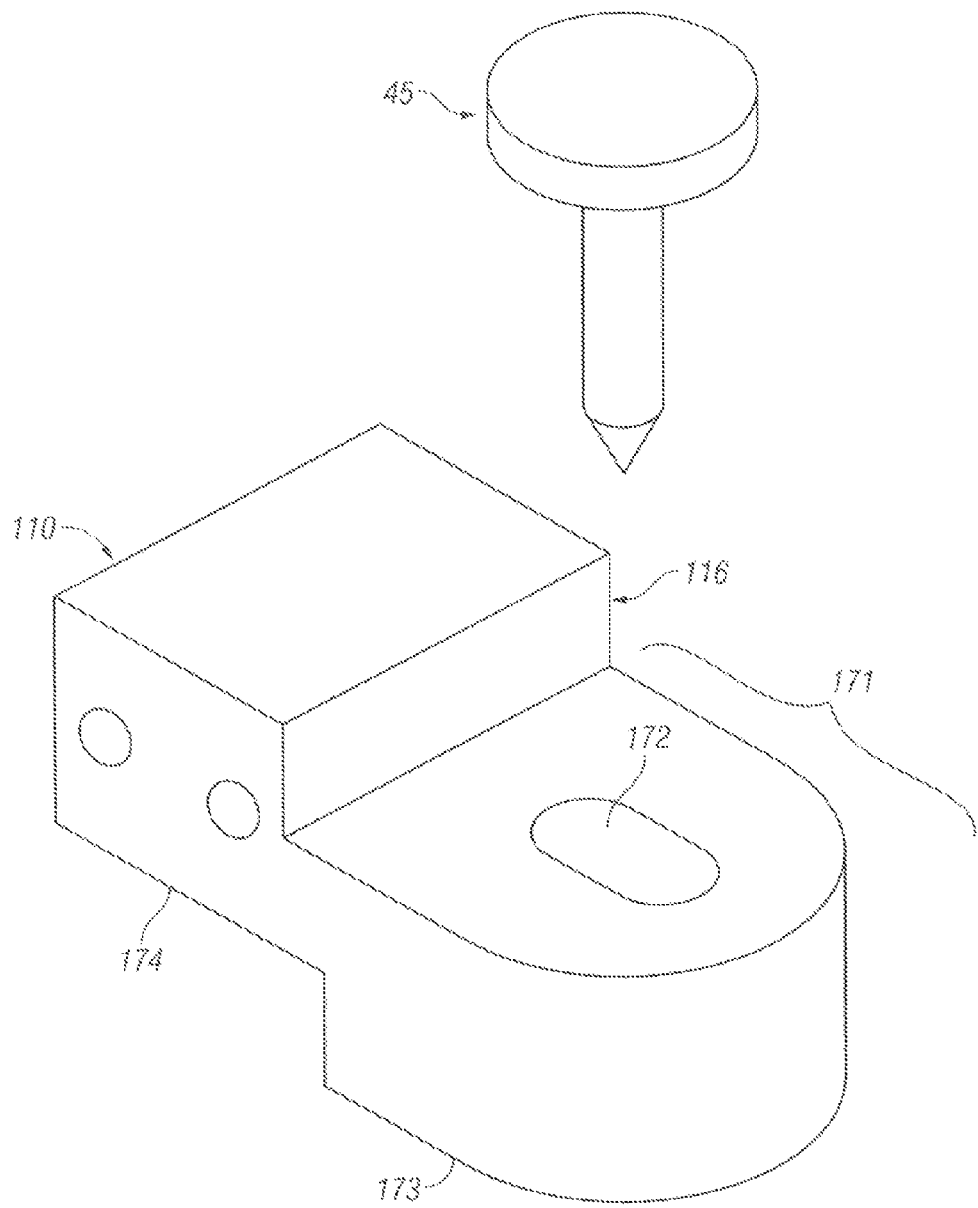
FIG. 47 is a pictorial view similar to FIG. 45 but of a second configuration of a clasp of the type shown in FIGS. 44 and 45.
Figure 48:
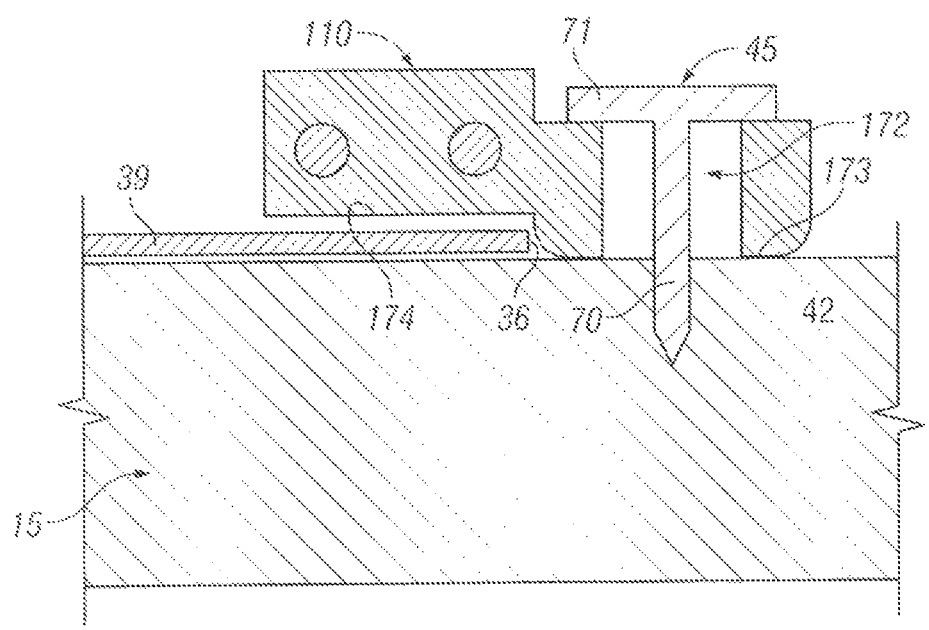
FIG. 48 is a partial cross-sectional side view similar to FIG. 45 but of the second embodiment of the clasp shown in FIG. 47.

Reference is made to FIGS. 47 and 48 which illustrate a variant of a clasp member 110 shown in FIGS. 45 and 46. The clasp member 110 in FIGS. 47 and 48 is provided with a lower surface which is stepped to provide a lower surface 173 over the fastening tab 171 which is located axially relative to the opening 172 farther than a lower surface 174 underneath the remainder of the clasp member 110. As seen in FIG. 48, the screw 45 is shown as pinning the fastening tab 171 to the condyle 15 with the lower surface 173 of the fastening tab engaged with the surface of the condyle 15, however, with the lower surface 174 of the clasp member 110 is sufficiently spaced from the surface of the condyle 15 to permit the sheet member 39 to be received therein without being pinched between the clasp member 110 and the condyle 15 and, therefore, free for relative movement. In FIG. 47, the opening 172 is shown to be an elongate slot extending normal to the circumferential extent of the ligature 75 and thus to provide for relative movement of the clasp member 110 relative to the screw 45 in a direction substantially normal to the direction of extension of the circumferential ligature 75.

Figure 49:
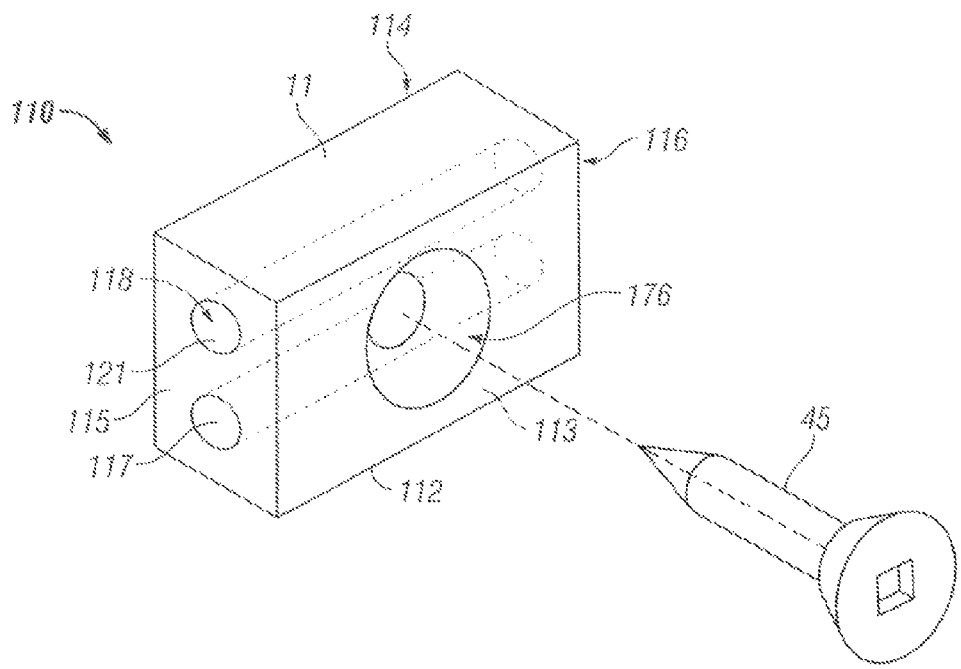
FIG. 49 is a pictorial view in accordance with a thirteenth embodiment showing schematically an alternate form of the clasp shown in FIG. 22 for use with a securing screw.
Figure 50:
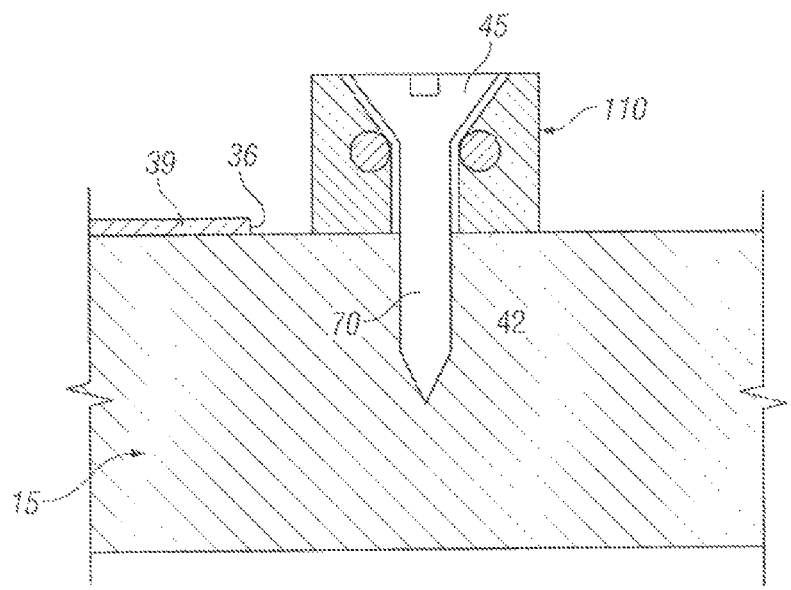
FIG. 50 is a partial cross-sectional view similar to that shown in FIG. 45 but utilizing the clasp of FIG. 49.

Reference is made to FIGS. 49 and 50 which illustrate a thirteenth embodiment in accordance with the present invention. As seen in FIG. 49, the clasp member 110 is identical to the clasp member 110 shown in FIGS. 17 to 23 with the exception that an opening 176 is provided through the clasp member. A screw 45 is adapted to pass through the opening 176 and into the condyle 15 to secure the clasp member 110 to the condyle. As seen in FIG. 50, the edge 36 of the sheet member 39 is preferably provided to be inwardly on the prosthesis 30 from the clasp member 110. Preferably, as seen in FIG. 50, the opening 176 is oval so as to permit relative movement of the clasp member 110 relative to the screw 45 in a left to right direction as seen in FIG. 50.

In each of the embodiments illustrated in FIGS. 42 to 50, the screw 45 is engaged in the condyle 15 and the circumferential ligature 75 secured to the screw 45 either directly as by winding the circumferential ligature 75 about the screw or by the screw securing to the condyle with clasp member 110 which is secured to the circumferential ligature 75. These arrangements provide an anti-rotational feature which assists in preventing the prosthesis 30 from rotating about the condyle, for example, rotating circumferentially relative to the ligature 75. Utilizing the circumferential ligature directly or indirectly coupled to a screw is advantageous to having a screw engage in a hole in the thin sheet member 39 since the thin sheet member 39 is more liable to be subject to tearing.

In each of the embodiments illustrated in FIGS. 42 to 50, the screws 45 are schematically shown without threads, however, typical such screws would have suitable threads to assist the screws to be securely secured into the condyle 15. Other suitable fasteners may also be provided. Throughout the Figures illustrating the preferred embodiments, screw members are shown as a preferred form of a bone engaging fastener. However, the invention is not limited to using screw members as fasteners and any fastener may be used in accordance with the present invention which will adequately engage a bone member and couple a desired element to a bone member. Such fasteners include threaded fasteners and surgical staples, nails and the like.

Relative movement of the prosthesis to the articular surfaces 18 may be accomplished by having at least a portion of the outer portion 38 of the prosthesis over the non-articular surfaces 19 fixed to the bone against movement and the interpositional sheath portion 37 of the prosthesis over the articular surfaces 18 free to move at least to some extent relative the outer portion 38 over the non-articular surfaces 19 as, for example, by providing one or more flexible connections between the interpositional sheath portion 37 and the outer portion 38.

The prosthesis 30 may be provided so as to have different thicknesses over different areas. More preferably, different thicknesses over different areas where the prosthesis overlies the articular surface 18. The different thicknesses may be selected so as to provide some inherent memory to the prosthesis 30 over the articular surfaces 18 as can be advantageous to distribute loading forces or greater areas of the articular cartilage 18 then would be the case if there was no memory. By providing memory, the prosthesis returns to an inherent configuration at least under a range of at least some loading forces applied to the prosthesis in use of the joint.

The prosthesis 30 preferably may have its inner or outer surfaces comprise metal. For example, metal may be deposited on the surface of non-metal sheet like substrates as by various techniques including splatter deposition and vacuum deposition.

Figure 51:
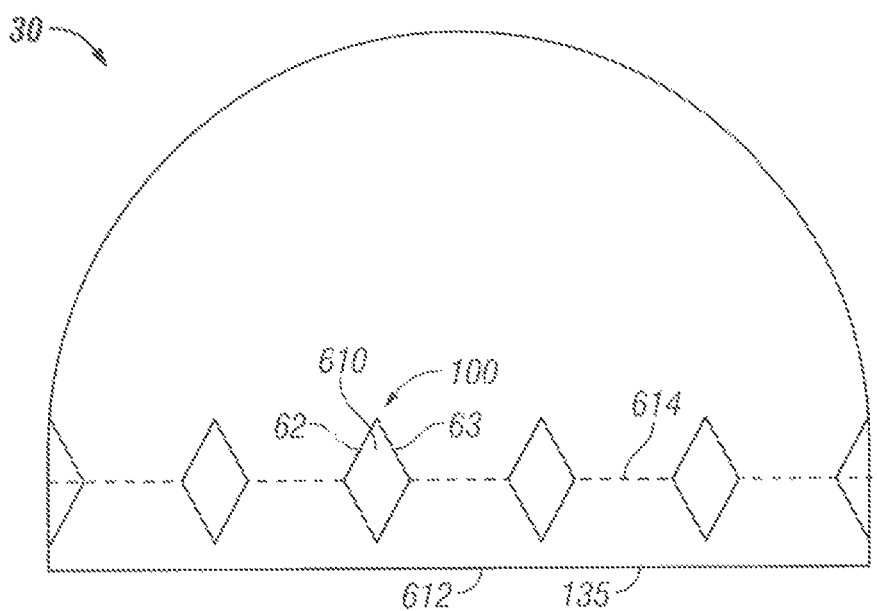
FIG. 51 is a schematic side view of a prosthesis in accordance with a fourteenth embodiment with the present invention in an unfolded state.
Figure 52:
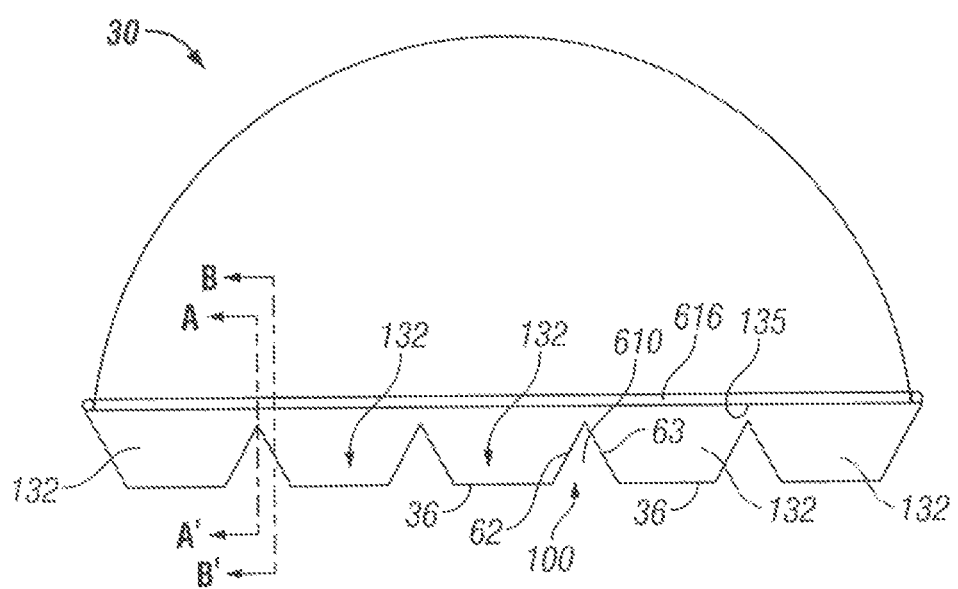
FIG. 52 is a side view of the prosthesis of FIG. 51 in a folded state ready for use.
Figure 53:
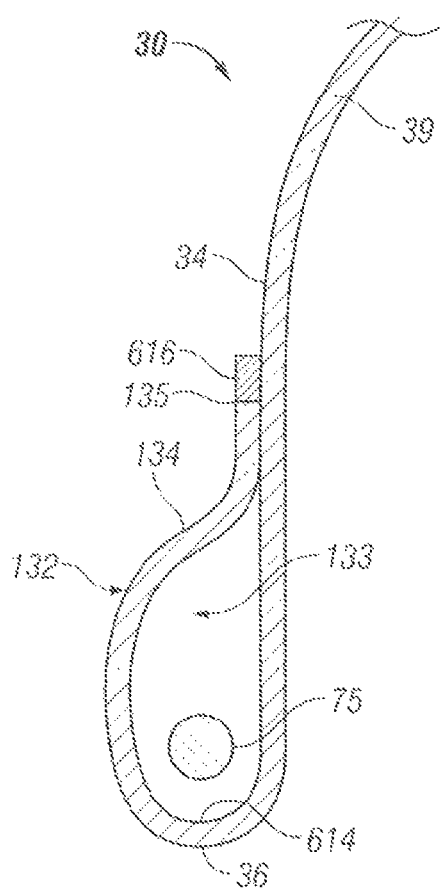
FIG. 53 is a cross-sectional side view of the prosthesis of FIG. 52 along section A-A'.
Figure 54:
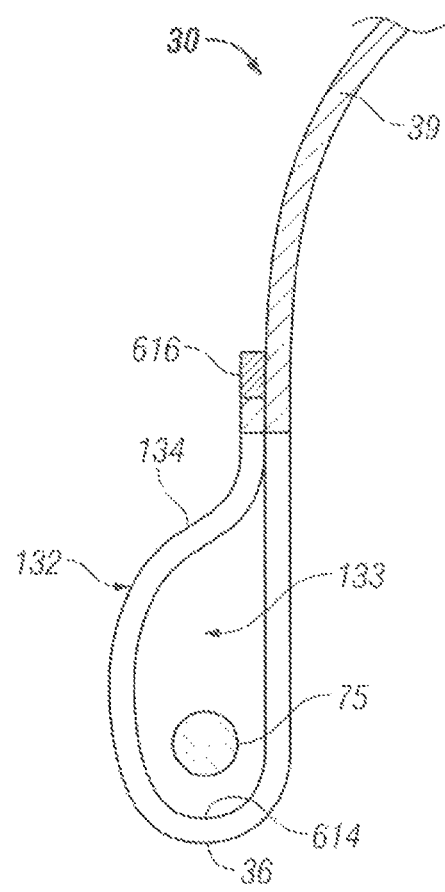
FIG. 54 is a cross-sectional side view of the prosthesis of FIG. 52 along section line B-B'.

Reference is made to FIGS. 51 to 54 which illustrate a fourteenth embodiment of a prosthesis 30 in accordance with the present invention. FIG. 51 shows the prosthesis 30 in a schematic side view. The prosthesis 30 is a cap-like member similar to that shown in FIG. 13, however, adapted to be provided with a plurality of slotways 100 and loop members 132 having similarities to the slotways 100 and loop members 132 in the embodiment of FIGS. 17 to 22. FIG. 51 shows the prosthesis 30 during its manufacture in which a plurality of diamond shaped slotways 100 have been cut from the sheet member 39 at circumferentially spaced locations. The sheet member 39 is shown to have a distal end 135 extending circumferentially of the pre-form shown in FIG. 51. The pre-form of FIG. 51 is folded about a circumferential fold line 614 to provide the prosthesis in its finished configuration ready for use as seen in side view in FIG. 52. As can be seen, for example, in FIG. 53, with folding of the sheet member 39 back upon itself along the fold line 614, the portion of the sheet member 39 between the distal end 135 and the fold line 162 comes to form loop members 132 between the slotways 100 with the distal end 135 welded to the outside surface 34 of the sheet member 39 to form the opening 133 through each loop member 132 within which opening 133 the circumferential ligature 75 extends as seen, for example, merely in FIGS. 53 and 54. As seen in FIGS. 52 to 54, a circumferential weld 616 is provided to assist in securing the distal end 135 to the outer surface 34 of the sheet member. The weld 616 extends circumferentially about the prosthesis 30 as best seen in FIG. 452. Each of the slotways 100 has a gap 610 between the edges 62 and 63. On the circumferential ligature being tightened, the edges 62 and 63 may be drawn together. The circumferential weld 616 assists in preventing any tearing which may occur at the juncture between the edges 62 and 63 extending from the slotway 100 upwardly into the sheet member 39 on the other side of the weld 616. In the embodiment of FIGS. 52 to 54, the edges 62 and 63 are shown to extend as straight lines to their junction meeting in an apex. However, as is the case with the embodiment of FIGS. 17 to 22, the slotway may have a keyhole blind end similar to the keyhole blind end 101 with a truncated circular periphery. As another alternative, the apex of the cut edges 62 and 63 may end proximate the weld element 616. The weld element 616 is preferably provided at a circumferentially extending location which overlies non-continuous surfaces of a bone that are not normally in contact during normal movement of the joint. Preferably, the circumferential weld 616 will be provided at a location on the prosthesis which does not need to have its circumferential extent be reduced when applying the prosthesis onto a bone.

Figure 55:
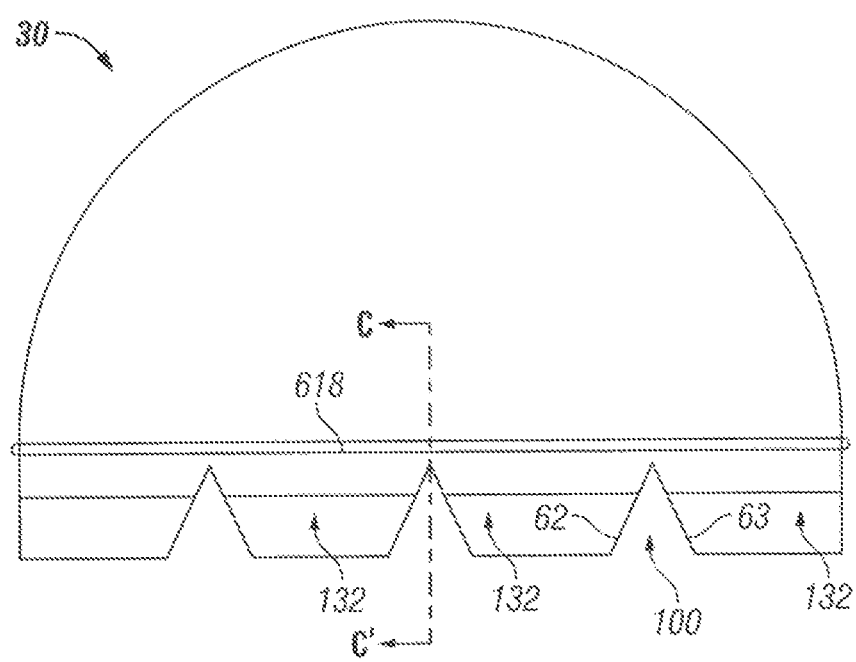
FIG. 55 is a schematic side view of a prosthesis in accordance with a fifteenth embodiment of the invention ready for use.
Figure 56:
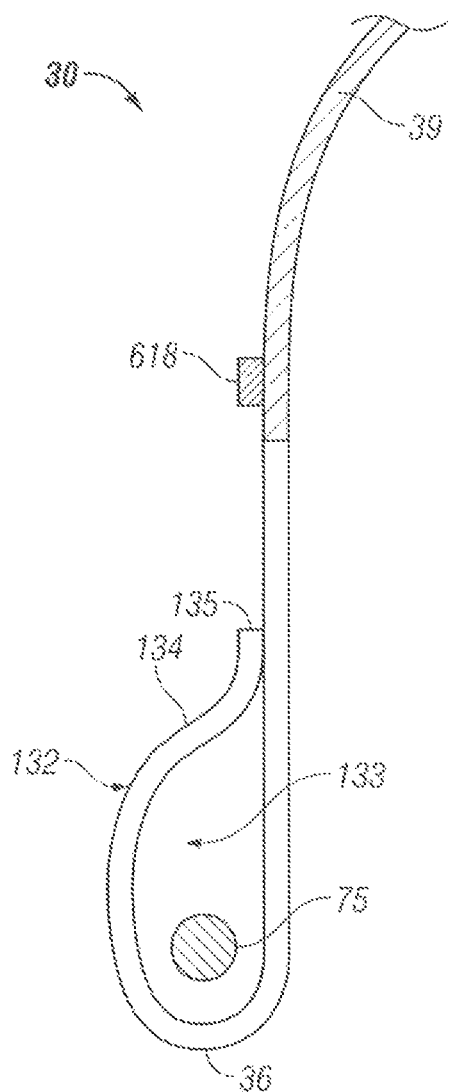
FIG. 56 is a cross-sectional side view of the prosthesis of FIG. 55 along section line C-C'.

Reference is made to FIGS. 55 and 56 which show a fifteenth embodiment of a prosthesis 30 in accordance with the present invention. The prosthesis 30 in FIG. 55 has similarities to the prosthesis of FIG. 52 with a notable exception that when the loops 132 are folded back, the distal end 135 does not extend as far as the circumferential weld 168. Thus, as seen in FIG. 55, the circumferential weld 168 is independent of the loops 132. As seen in FIG. 56, the distal end 135 is provided at a location outwardly from the junction of the cut edges 62 and 63, although this is not necessary, and the distal end 135 may be provided at any location in the embodiment of FIG. 5 outwardly from the circumferential weld 616.

Figure 57:
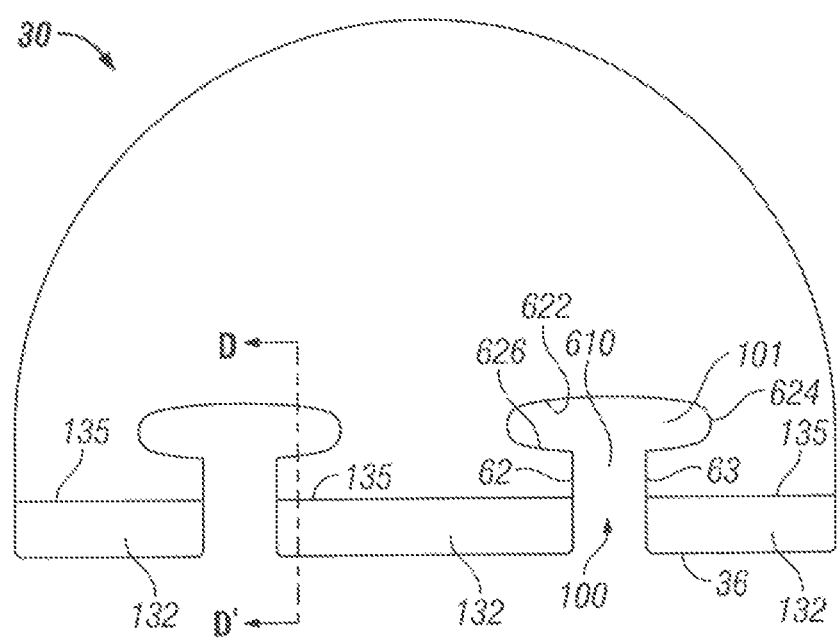
FIG. 57 is a schematic side view of a prosthesis in accordance with a sixteenth embodiment of the present invention ready for use.
Figure 58:
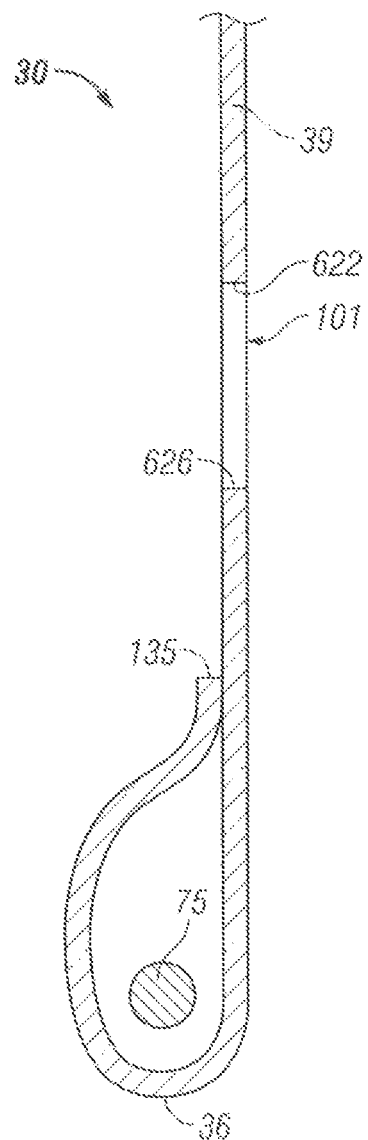
FIG. 58 is a cross-sectional side view of the prosthesis of FIG. 57 along section line D-D'.

Reference is made to FIGS. 57 and 58 which show a sixteenth embodiment of a prosthesis 30 in accordance with the present invention. The embodiment of FIG. 57 shows each keyhole slotway 100 as having an enlarged keyhole blind end 101 which is elongated in a circumferential direction. The keyhole blind end 101 has an elongate inner edge 622, two ovalled end edges 624 and outer edges 626. Each loop member 132 end at a distal end 135 which is preferably spaced from the outer edge 626 of the blind end 101. Providing the blind end 101 to have an increased circumferential extent with smoothly curved oval edges 624 assists the sheet member 39 in accepting localized forces applied at the inner blind end 101 of the slotway 100 to accommodate deformation and flexure towards preventing the sheet member 39 from tearing.

Figure 59:
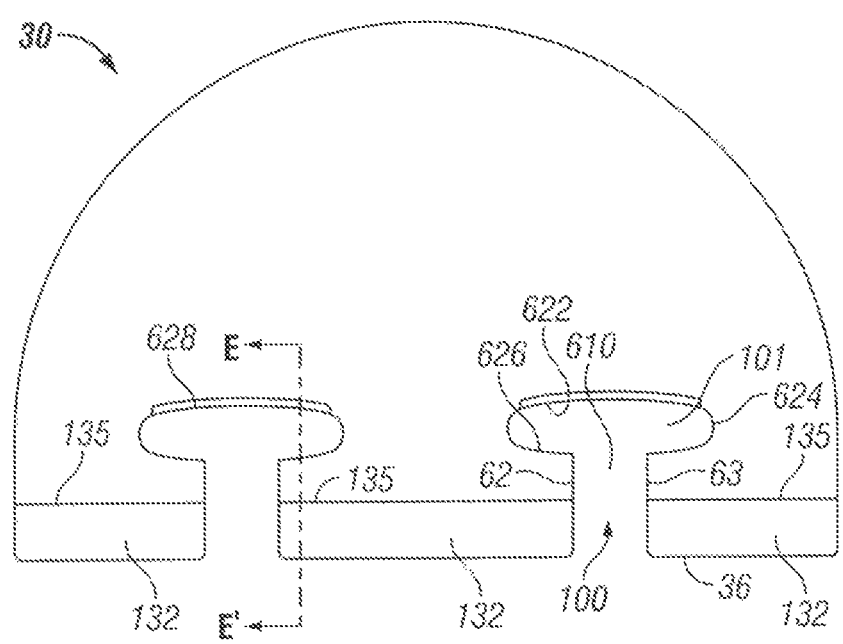
FIG. 59 is a schematic side view of a prosthesis in accordance with a seventeenth embodiment of the present invention.
Figure 60:
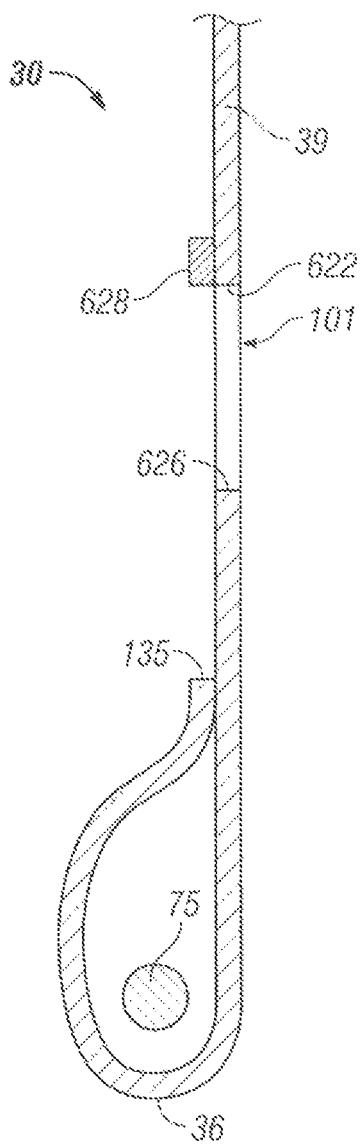
FIG. 60 is a cross-sectional side view of the prosthesis of FIG. 59 along section E-E'.

Reference is made to FIGS. 59 and 60 which illustrate a seventeenth embodiment of a prosthesis 30 in accordance with the present invention which is identical to the prosthesis illustrated in FIGS. 57 and 58 with the exception that a weld element or weld 628 is provided along a central portion of the inner edge 622 towards reinforcing this central portion of the inner edge 622 and assisting in resisting tearing of the sheet member 39 when deformed.

Figure 61:
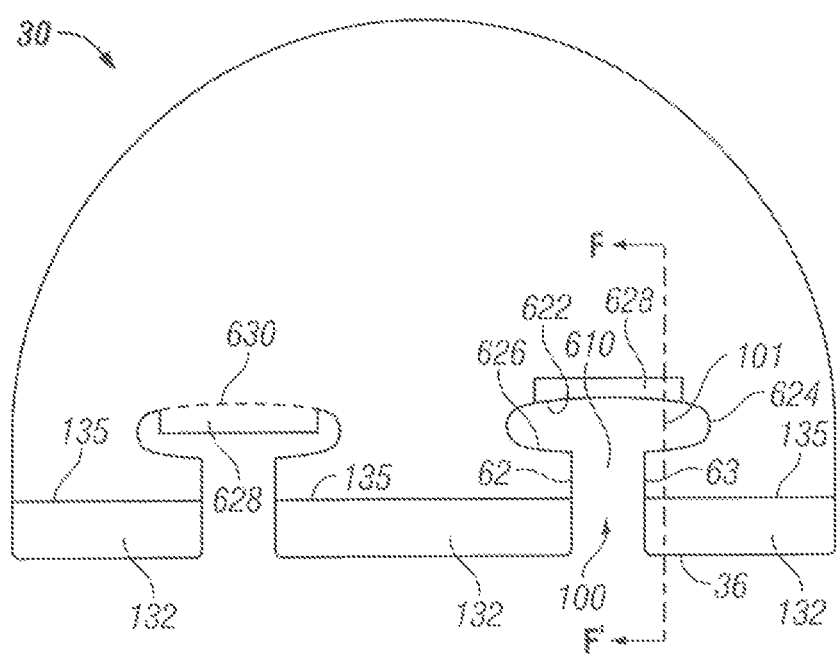
FIG. 61 is a schematic side view of a prosthesis in accordance with an eighteenth embodiment of the present invention ready for use.
Figure 62:
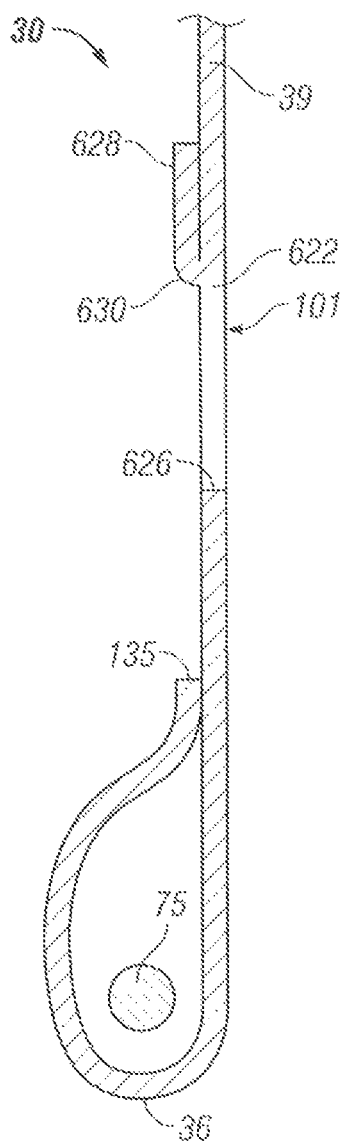
FIG. 62 is a cross-sectional side view of the prosthesis of FIG. 61 along section line F-F'.

Reference is made to FIGS. 61 and 62 which show an eighteenth embodiment of a prosthesis 30 in accordance with the present invention. The prosthesis 30 in FIG. 61 is identical to the prosthesis shown in FIGS. 57 and 58 with the exception that when manufacturing the blind end 101, a flap 628 of the sheet material 39 is maintained which flap 628 may be folded along a fold line 630 so as to provide as seen in the right hand keyhole slotway 100 in FIG. 61, the flap 628 folded back upon the sheet member 39 and secured as by welding thereto with the folded edge 36 of the flap 628 forming a central portion of the inner edge 622 of the blind end 101. FIG. 61 shows two keyhole slotways 100. The keyhole slotway on the right hand side shows a first keyhole slotway 100 in a final configuration ready for use whereas the left hand keyhole slotway 100 shows the keyhole slotway 100 during manufacture prior to a flap 628 being folded back upon the sheet member 39.

The folded back reinforcing 628 reinforces the inner edge 622 of the blind end 101 of the keyhole slotway 100 to resist tearing.

Selected portions of the prosthesis may have desired mechanical properties for different purposes, for example, of being rigid to distribute loading, of resisting deformation towards distribute loading, of deforming with resiliency as to provide memory, and deforming without memory to adopt a shape to which it is deformed as to maintain a shape about a neck of a condyle. These mechanical properties may be achieved by suitable selection of materials of construction and structure. For example, if a sheet of metal forming the sheath portion 37 in FIG. 19 is to be resilient than it may more preferably consist of a metal which has higher resiliency such as preferably zirconium or an alloy of zirconium. If, for example, the coupling portion 38 may be desired to adopt a shape to which it is deformed than it may more preferably consist of a metal which has low resiliency such as preferably tantalum or an alloy of tantalum.

In accordance with the present invention, while preferred, it is not necessary that either or both of the inner surface and the outer surface of the prosthesis to be in engagement with the articular cartilage may comprise metal. Non-metal surfaces may be utilized which permit relative sliding and movement of the one or both of the inner and outer surfaces of the prosthesis on the bone which the prosthesis overlies and achieves the desired objective of having a prosthesis which is free to move relative to at least one of the articular surfaces to which it is to be engaged and, preferably, relative to both of the articular surfaces which it is to engage. The entire prosthesis thus may comprise polymer materials without any metal, preferably with the inner surface and the outer surface selected to for relative movement of the prosthesis on the bone. Facilitating such movement is preferably accomplished by providing surfaces which are smooth, have a coefficient of friction sufficiently low to facilitate movement and/or resist bonding to the bone member. Preferably, both the outer surface and the inner surface are smooth.

The Figures illustrating the preferred embodiments of the invention are not to scale. The sheet member forming the prosthesis is thin as, for example, less than 0.01 inches. The drawings generally show the prosthesis and particularly the edge of the prosthesis as having a thickness which is selected for ease of illustration without being to scale.

Figure 63:
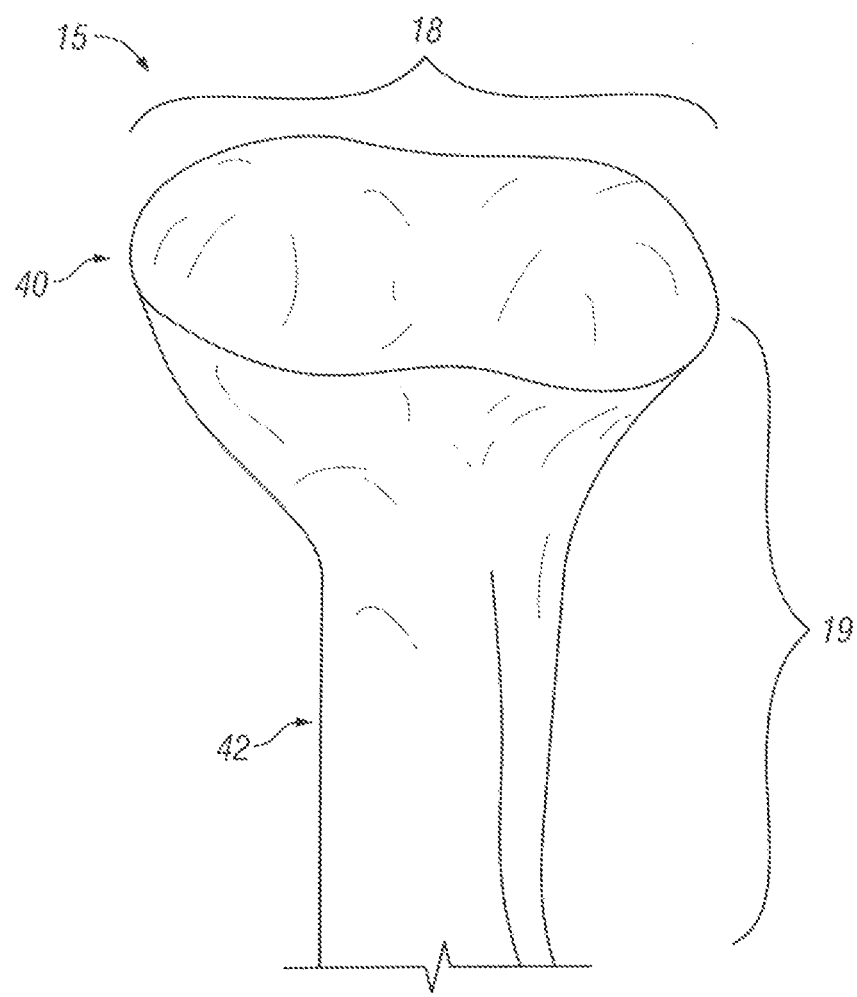
FIG. 63 is a schematic pictorial front view of the right side condylar process of the mandible shown in FIG. 7.
Figure 65:
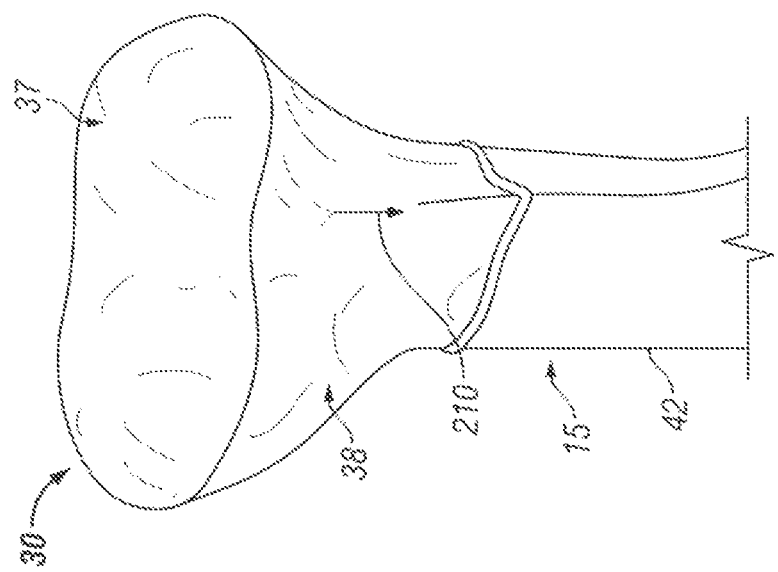
FIG. 65 is a schematic pictorial front view of the right side condyle of the mandible as shown in FIG. 63 on which there is engaged the prosthesis of FIG. 64.
Figure 64:
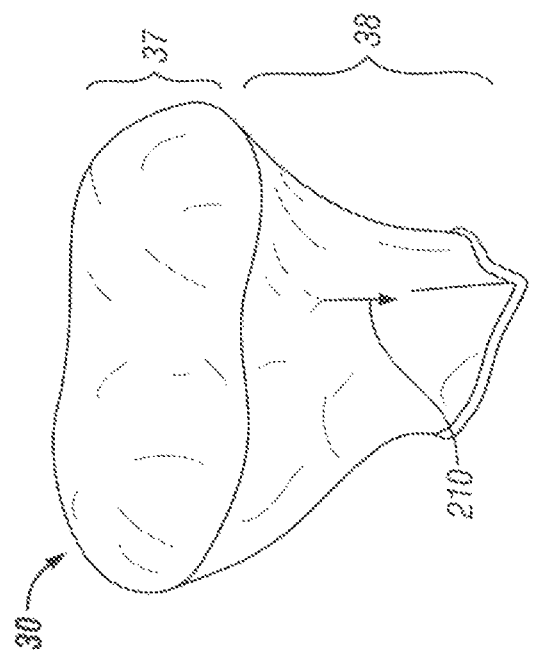
FIG. 64 is a schematic pictorial front view of position a nineteenth embodiment of a prosthesis in accordance with the present invention in an unbiased condition.

Reference is made to FIG. 63 which is a schematic pictorial front view of the right side condyle 15 of the mandible 13. The condyle 15 has a bulbous end 40 and a reduced diameter neck 42. FIG. 64 illustrates a prosthesis 30 in accordance with a nineteenth embodiment of the present invention for application unto the condyle 15 of FIG. 63. FIG. 65 is a pictorial view the same as FIG. 63, however, showing the prosthesis 30 of FIG. 64 coupled to the condyle 15 of FIG. 63.

Figure 66:
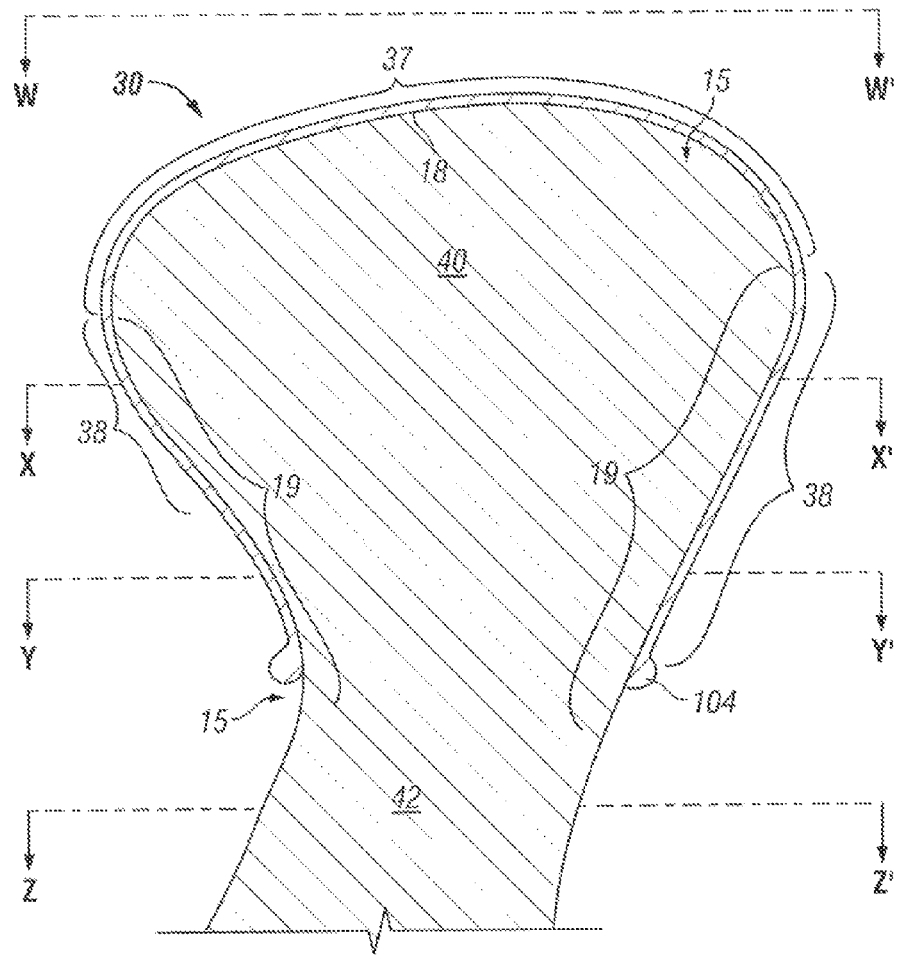
FIG. 66 is a cross-sectional view the same as FIG. 9 but of the prosthesis and condyle of FIG. 65.

As best seen in cross-section in FIG. 66, the condyle 15 has a convexly rounded outer surface over the bulbous end 40 which merges into the neck 42 of a reduced circumference smaller than a larger circumference of the bulbous end 40. The condyle 15 has an outer surface which includes articular cartilage 18 over an end portion of the bulbous end 40 and a non-contiguous surface 19 over the neck 42. The non-contiguous surface 19 is adjacent to and merges into the articular cartilage 18.

The prosthesis 30 comprises a cap-like portion 37 and a coupling portion 38. The cap-like portion 37 is shown separately in FIG. 73 to be closed at an inner end 99 and open at a circumferential peripheral outer edge 101. The coupling portion 38 comprises a tubular member with a circumferential side wall 102 that extends axially between a circumferential peripheral inner edge 103 and a circumferential peripheral outer edge 36. The outer edge 101 of the cap-like portion 37 is joined to the coupling portion 38 proximate the inner edge 103 of the coupling portion 38. The prosthesis 30 provides an opening 35 defined by the outer edge 36 of the tubular member of the coupling portion 38. The thickness of coupling portion 38 is enlarged about the edge 36 as a reinforcing annular ring member 104.

The prosthesis 30 is engaged on the condyle 15 with the cap-like portion 37 to overlie the articular cartilage 18 of the bulbous end 40 and the coupling portion 38 annularly about the non-contiguous surface 19 of the first bone member not in contact with a second bone member during normal movement of the joint. The cap-like portion 37 overlies an upper portion of the bulbous end 40 and the coupling portion 38 and its annular ring member 104 are about the neck 42.

Figure 73:
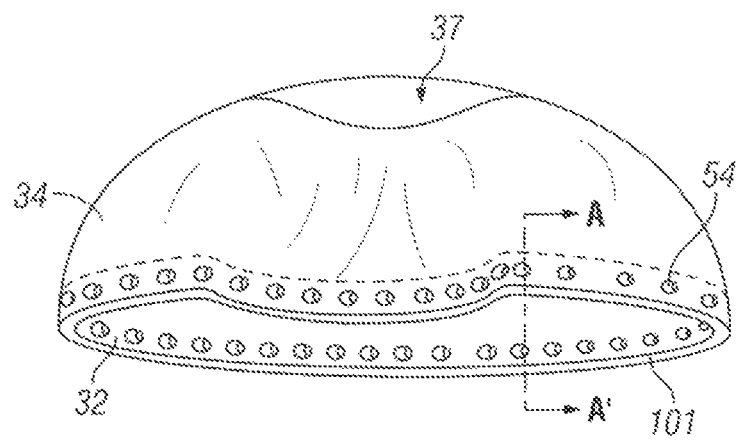
FIG. 73 is a perspective view of a cap-like portion of the prosthesis of FIG. 64.

The cap-like portion 37 in the embodiment shown in FIG. 73 to be shaped to somewhat like a dome for ease of illustration. The cap-like portion 37 is to match the shape of the end 40 which, in the embodiments, is shown as generally dome shaped for ease of illustration. However, the cap-like portion 37 is to have a shape and size to match the shape and size of the condyle 15. The shape and size of the condyle 15 may include both convex and concave surfaces, as with convex valleys between concave portions.

Figure 67:
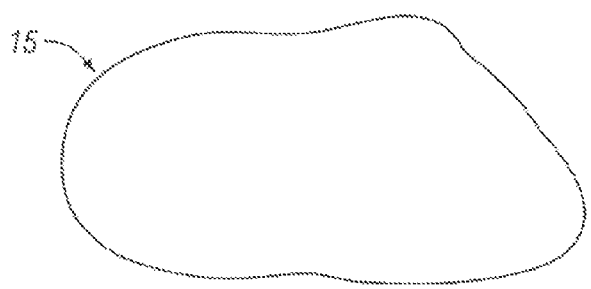
FIG. 67 is a top view of the condyle and prosthesis of FIG. 65 as seen from line W-W' in FIG. 66.
Figure 68:
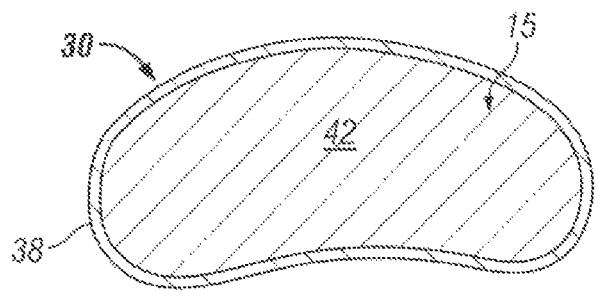
FIG. 68 is a cross-sectional view of the condyle and prosthesis of FIG. 65 along section line X-X' in FIG. 66.
Figure 69:
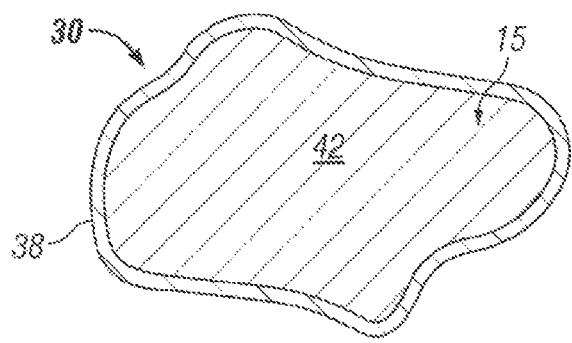
FIG. 69 is a cross-sectional view of the condyle and prosthesis of FIG. 65 along section line Y-Y' in FIG. 66.
Figure 70:
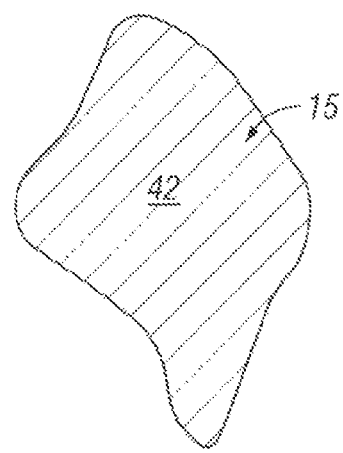
FIG. 70 is a cross-sectional view of the condyle and prosthesis of FIG. 65 along section line Z-Z' in FIG. 66.

The condyle 15 is difficult to illustrate in line drawings, however, as is well known by persons skilled in the art and typical of many condyles, the condyle 15 is typically not symmetrical but rather has defined outer surface portions which are often asymmetrical. Towards attempting to best understand the nature of the outer surfaces of the condyle 15, FIGS. 67 to 70 represent different top and top cross-sectional views showing how the circumferential shape and size of the condyle 15 changes along its axial length. FIG. 67 presents a top view of the condyle 15 and prosthesis 30 of FIG. 65 as seen from section line W-W' in FIG. 66 and each of FIGS. 68, 69 and 70 represent, respectively, cross-sectional views along parallel section planes X-X', Y-Y' and Z-Z' normal to the sectional access 9-9' in FIG. 7. As can be seen from a comparison of FIGS. 67 to 70, the cross-sectional shape of the condyle 15 varies considerably along the cross-section line 9-9' in FIG. 7. The cross-sections in FIGS. 68 and 69 show the coupling portion 38 of the prosthesis 30 about the neck 42. Of course, as this is the case throughout the application, the drawings are not to scale. As can be seen having regard to FIGS. 66, 68 and 69, the prosthesis 30 closely overlies the outer surface of the condyle 15 and, in particular, as can be seen in FIGS. 68 and 69, the coupling portion 38 preferably closely engages the non-contiguous outer surface 19 about the neck 42. Preferably, the coupling portion 38 when engaged upon the neck 42 has a shape and size that corresponds to the shape and size of the neck 42. This is advantageous such that the coupling portion 38 will engage the neck 42 in a manner that accurately locates the cap-like portion 37 to overlie the articular cartilage 18 of the end 40 of the condyle 15 in a desired position and orientation axially and circumferentially yet permitting for relative movement of the cap-like portion 37 over the articular cartilage 18 without the cap-like portion 37 becoming disengaged from the end 40.

As can be seen, the non-contiguous surface 19 about the neck 42 varies in an irregular manner both axially of the neck 42 and circumferentially of the neck 42. In accordance with the preferred arrangement of the nineteenth embodiment, the coupling portion 38 in a closed position about the neck 42 adopts a closed shape that has a shape and size which is substantially the same as the shape and size of the neck 42.

Preferably, the coupling portion 38 as seen in FIG. 64 is formed so as to inherently adopt the closed shape, that is, a shape and size which corresponds to the shape and size of the outer surface of the neck 42. This may be accomplished in a number of manners. In one manner, the coupling portion 38 may be formed so that it has an inherent shape corresponding closely to the shape of the neck 42. For example, in one preferred embodiment, the coupling portion 38 is formed from a resilient material that has an inherent bias to adopt a three-dimensional shape and size both as to axial shape and size and circumferential shape and size which corresponds substantially identically to the shape and size of the neck 42. Thus, the prosthesis 30 is be pre-formed separate from the condyle 15 so as to have interior surfaces of the coupling portion 38 and, preferably, also the cap-like portion 37 corresponding in shape to the outer surfaces of the condyle. The coupling portion 38 preferably comprises a material which is resilient and expandable so that the coupling portion 38 may be expanded to an open condition pass over the end 40 of the condyle 15 and then, under its inherent bias, contract to assume as its inherent shape the closed shape having the same shape and size as the neck 42. With the coupling portion 38 having an inherent shape substantially identical to the shape and size of the neck 42, the coupling portion 38 will in contracting from an expanded condition attempt to assume a configuration about the neck 42 which accurately locates the coupling portion 38 on the neck 42 at a desired location both axially and rotationally about the axis of the condyle 15. The prosthesis 30 may thus be engaged about the condylar process 100 approximately in the desired position and the resilient coupling portion 38 will inherently assist in locating itself in a preferred orientation in which the coupling portion 38 is substantially identical in shape to the neck and the closed shape of the coupling portion 28 and the matching shape and size of the outer surface of the neck 24 of the first bone member complementarily coincide.

The nineteenth embodiment of the prosthesis 30 of FIG. 64 shares functional similarities with the tenth embodiment of FIGS. 40 and 41 in that a coupling portion 38 of each is resilient and expandable so that the coupling portion 38 may be expanded to pass over the bulbous end 40 of the condyle 15 and contract for engagement about the neck 42 of the condyle 15. In each of FIGS. 40 and 64, the coupling portion 38 is a tubular member. In FIG. 64, the tubular coupling portion 38 has increased axial length compared to the tubular coupling portion 38 in FIG. 40.

Figure 71:
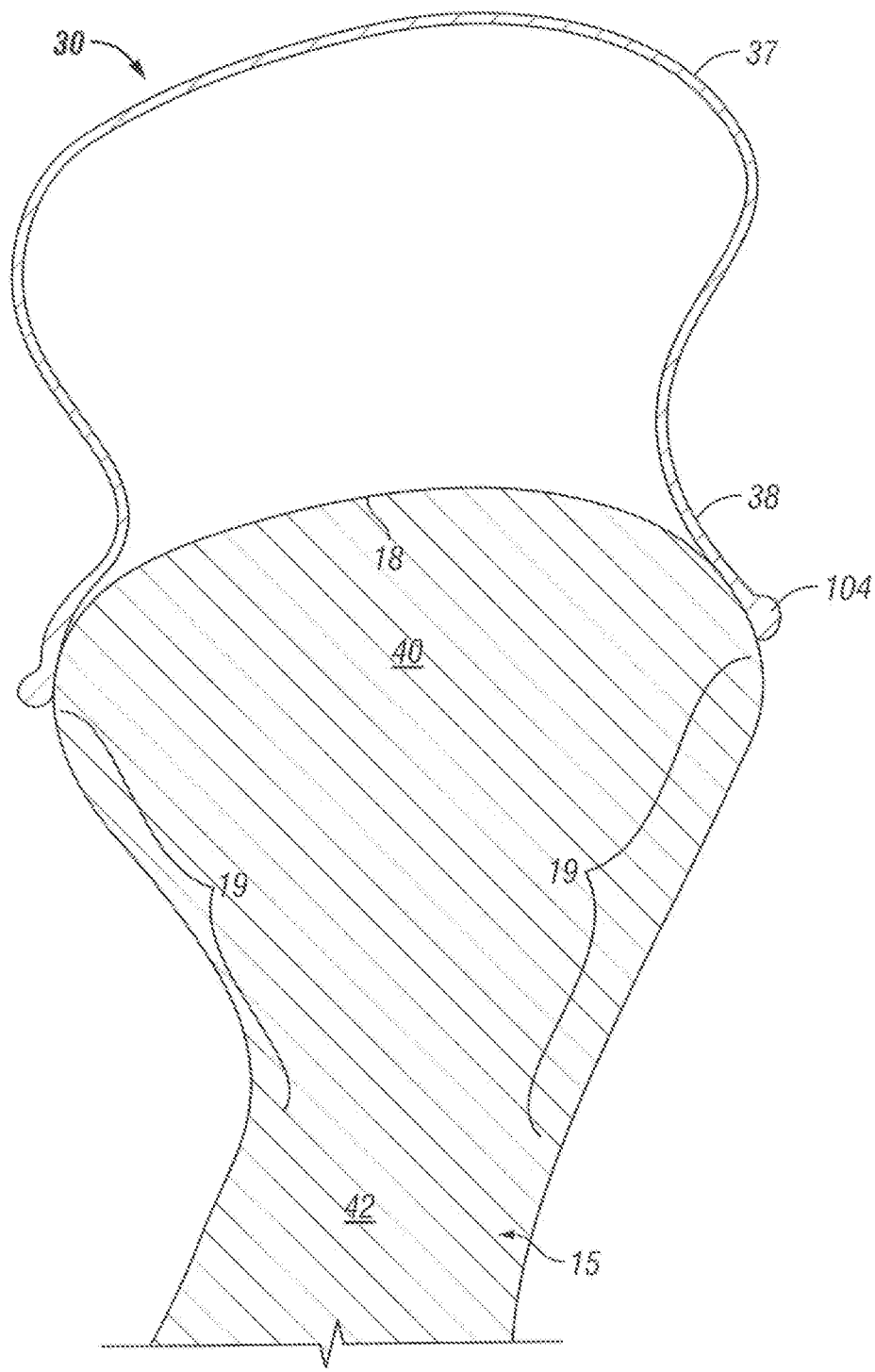
FIG. 71 is a side view of the condyle of FIG. 65 and the prosthesis of FIG. 64 in a first condition during coupling of the prosthesis to the condyle.
Figure 72:
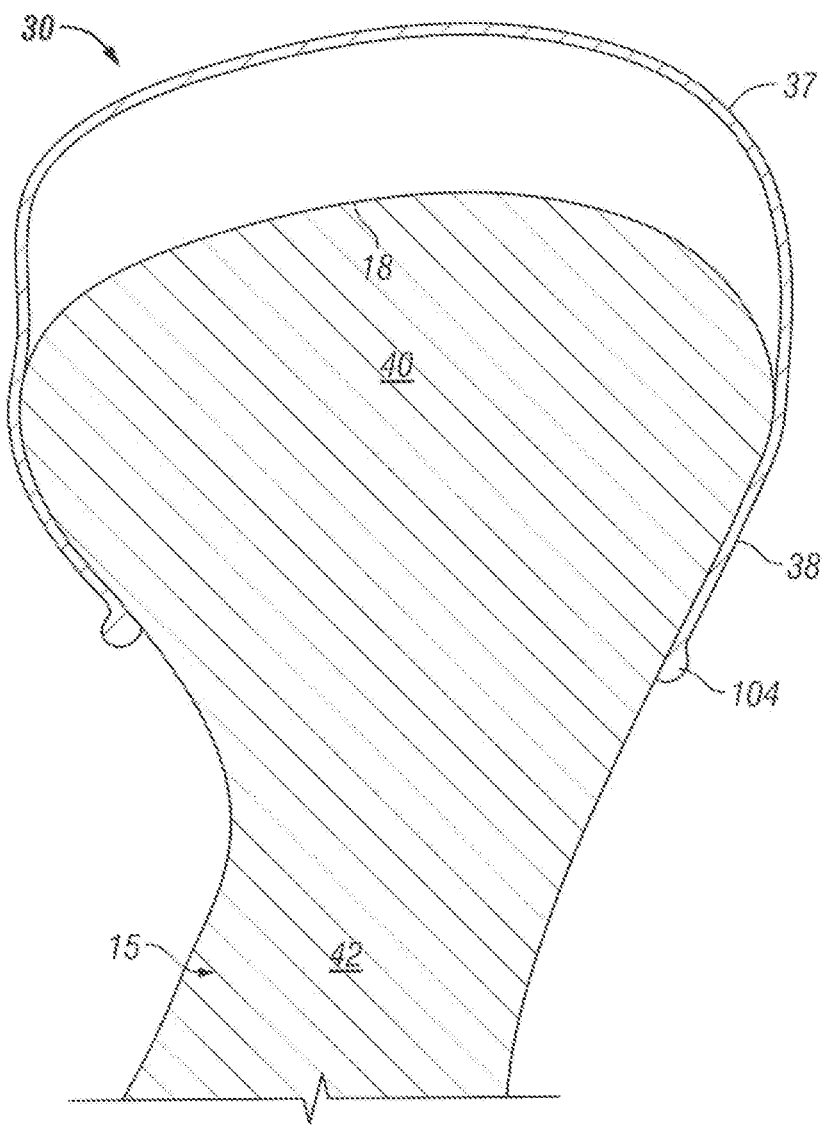
FIG. 72 is a side view of the condyle of FIG. 65 and the prosthesis of FIG. 64 in a second condition during coupling of the prosthesis to the condyle.

The tubular coupling portion 38 is resilient and can be expanded circumferentially from an unbiased contracted configuration as seen in solid lines in FIGS. 64 and 66 to expanded configurations such as seen in FIGS. 71 and 72. In the unbiased contracted configuration as seen in FIG. 66, the tubular coupling portion 38 has a first circumference at any point along its axial length and, when expanded circumferentially to one of the expanded configurations, the tubular coupling portion 38 has a second circumference at each point along its axial length greater than the corresponding first circumference. The tubular coupling portion 38 is resilient and has an inherent bias to assume the unbiased contracted condition of FIGS. 64 and 66. When expanded to any one of the expanded configurations, the tubular coupling portion 38 is biased under its inherent bias to return to the unbiased contracted configuration.

From the unbiased contracted configuration shown in FIG. 64, the prosthesis 30 may be applied onto the condyle 15 by passing the bulbous end 40 of the condyle 15 through the opening 36 of the prosthesis 30 expanding the resilient tubular coupling portion 38 as, for example, to adopt a first expanded configuration as shown in FIG. 71 and, subsequently, a second expanded condition as shown in FIG. 72 and, further subsequently, assuming the unbiased coupled condition as shown in FIGS. 65 and 66.

The inherent bias of the tubular member of the coupling portion 38 causes the tubular member to engage the neck 42 and assume a circumference corresponding to the circumference of the neck 42. This engagement of the coupling portion 38 about the neck 42 resists removal of the prosthesis 30 from the condyle 15 yet permits marginal movement of the cap-like portion 37 of the prosthesis 30 relative to the condyle 15. The cap-like portion 37 of the prosthesis is preferably pre-formed to have a shape and size the same as the shape of the outer surface of the articular cartilage 18 of the condyle 15 yet when coupled to the condyle 15, the cap-like portion 37 permits marginal movement of the prosthesis 30 relative the outer surface of the articular cartilage 18 of the condyle 15 without displacement from engagement with the outer surface of the articular cartilage 18 of the condyle 15.

The cap-like portion 37 in the nineteenth embodiment of FIGS. 65 to 75, as best seen in FIG. 73, preferably comprises a thin sheet of metal having an inner surface 32 and an outer surface 34, preferably with the thickness between the inner surface 32 and the outer surface 34 not greater than 0.01 inches. Preferably, the sheet of metal may consist merely of a thin sheet of metal, preferably of tantalum. As seen in the enlarged cross-sectional view of FIG. 75, the cap-like portion 37 has the peripheral outer edge 101 and an inner edge 103 of the coupling portion 38 is secured to the cap-like portion 37 proximate the outer edge 101. The coupling portion 38 in the embodiment of FIGS. 65 to 75 preferably comprises a polymer or plastic material. The polymer or plastic material is preferably resilient and has a desired inherent resiliency.

Figure 74:
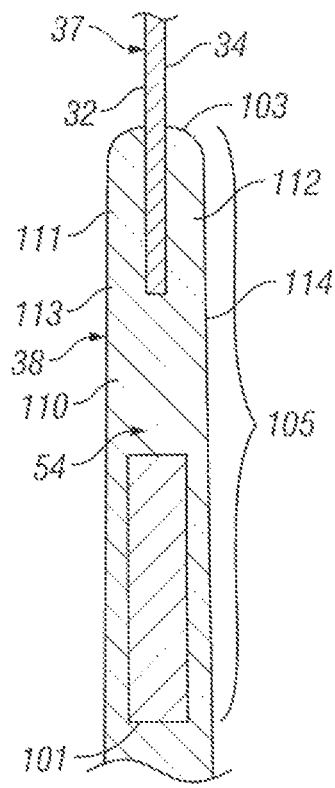
FIG. 74 is an enlarged portion of the cross-sectional view of FIG. 66 at the juncture of the cap-like portion and the coupling portion as along a section line shown as A-A' in FIG. 73.

As seen in FIG. 74 the inner edge 103 of the coupling portion 38 is secured to the outer edge 101 of the cap-like sleeve 37. As seen in FIG. 73, the cap-like portion 37 is provided with a plurality of circumferentially spaced holes 54 through the cap-like portion 37 in a circumferentially extending array about the outer edge 101 inwardly from the outer edge 101. As can be seen in cross-section in FIG. 74, the coupling portion 38 encapsulates a peripheral segment 105 of the cap-like portion 37 inward from the outer edge 101. As seen in FIG. 74, the coupling portion 38 is bifurcated providing an inner layer 111 of the coupling portion 38 inside the cap-like portion 37 and an outer layer 112 of the coupling portion 38 outside the cap-like portion 37. The inner layer 111 and the outer layer 112 merge outwardly from the outer edge 101 of the cap-like portion 37. The engagement of surfaces of the coupling portion 38 over both the inner surface 32 and the outer surface 34 of the cap-like portion 37 increases the surface area for bonding between the cap-like portion 37 and the cap-like portion 37.

The coupling portion 38 includes bridge members 110 with one bridge member 110 extending through each opening 54 of the cap-like portion 37 to couple the inner layer 111 of the coupling portion 38 inside the cap-like portion 37 with the outer layer 112 of the coupling portion 38 outside the cap-like portion 37. As seen in FIG. 74, the coupling portion 38 engages the cap-like portion 37 over the inner layer 111, the outer layer 112 and the bridge portions 110. Surfaces of the coupling portion 38 preferably bond or are adhesively secured to the surfaces of the cap-like portion 37. Each bridge member 110 is preferably formed integrally with the inner layer 111 and the outer layer 112 so that the coupling portion 38 is mechanically coupled to the cap-like portion 37 resisting separation of the coupling portion 38 and the cap-like portion 37 unless the bridge members 110 may be broken and severed.

Figure 75:
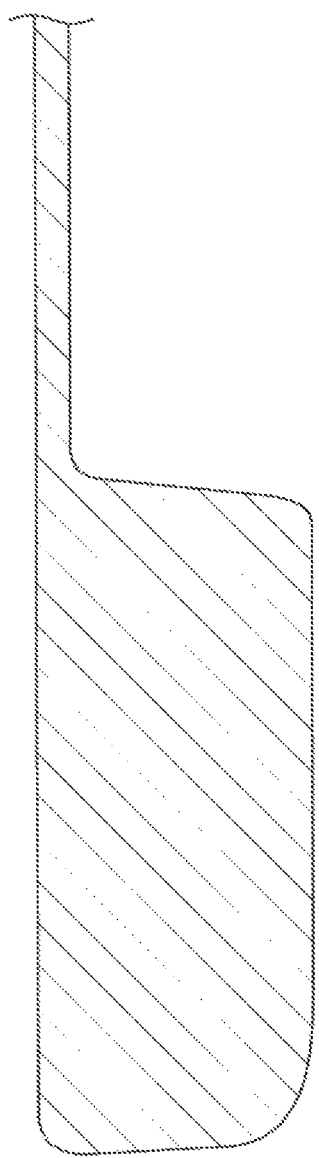
FIG. 75 is an enlarged portion of the cross-sectional view of FIG. 64 at the outer end of the coupling portion.

In the embodiment of FIGS. 65 to 75, the coupling portion 38 carries at its outer edge 36 the enlarged annular bead-like ring 104 of resilient material, best shown in enlarged cross-section in FIG. 75. The ring 104 is not necessary. However, the enlarged ring 104 is advantageous and serves a number of functions. Firstly, the ring 104 provides a reinforcement of the outer edge 36 so as to reduce the likelihood that the outer edge 36 may split either during application of the prosthesis 30 about the condyle 15 or after the prosthesis 30 may be applied to the condyle 15. The increased mass of the ring 104 provides increased forces that may be developed due to the inherent resiliency of the elastomeric material forming the ring 104 as can be advantageous to have the ring 104 under the inherent bias securely engage upon the neck 42 towards resisting movement of the ring 104 on the neck 42. The enlarged ring 104 also is of assistance in aiding engagement to facilitate application, and positioning of the prosthesis 30 on the condyle 15, such with the fingers or tools manipulated by a surgeon so as to apply the prosthesis 30 over the condyle 15 and located it in a desired position or orientation on the condyle 15.

As seen in FIG. 75, the enlarged annular bead-like ring 108 of the coupling portion 38 is shown to be generally rectangular in cross-section. The particular shape of the ring-like member may be varied to adopt broader shapes including circular, triangular, tapering and the like.

The coupling portion 38 may have varying thickness with more than one such ring extending circumferentially about the coupling portion and possibly similar rings disposed as to extend into a helical pattern about the coupling portion and which can be of assistance in assisting the coupling portion in assuming its axially inherent axial extent. The coupling portion 38 may be provided of varying thicknesses and may, for example, taper from an inner end to its outer end.

Figure 76:
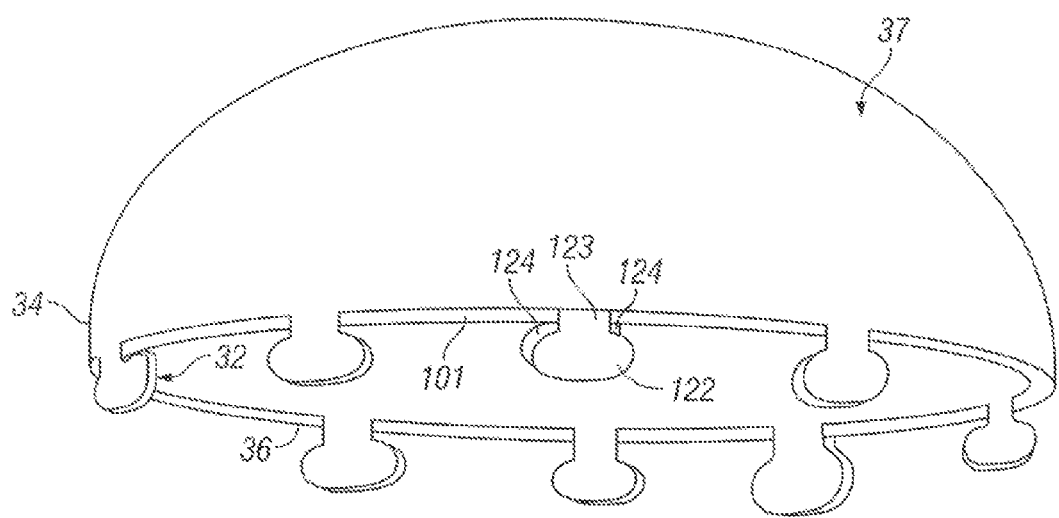
FIG. 76 is a perspective view similar to FIG. 73 but of an alternate configuration of a cap-like portion for prosthesis of FIG. 64.

Reference is made to FIG. 76 which shows an alternate version of the cap-like portion 37 for substitution of the cap-like portion of FIG. 73. For ease of illustration in FIG. 76, the cap-like portion 37 is shown as a simple dome shape. In FIG. 76, the outer edge 101 of the cap-like portion 37 includes a plurality of circumferentially spaced outwardly extending fingers 122 each of the fingers having a stem 123 with an enlarged end so as to provide two an axially inwardly directed shoulders 124 which may engage with an oppositely directed portions of the coupling portion 38 to mechanically resist separation of the coupling portion 38 and the cap-like portion 37 in a similar manner to that provided with the bridge members in FIG. 69. As with the cap like-portion 37 in FIG. 73, the cap like-portion 37 in FIG. 77 preferably consists of metal but may alternatively comprise a relatively rigid plastic or polymer coated with metal on both surfaces.

Figure 77:
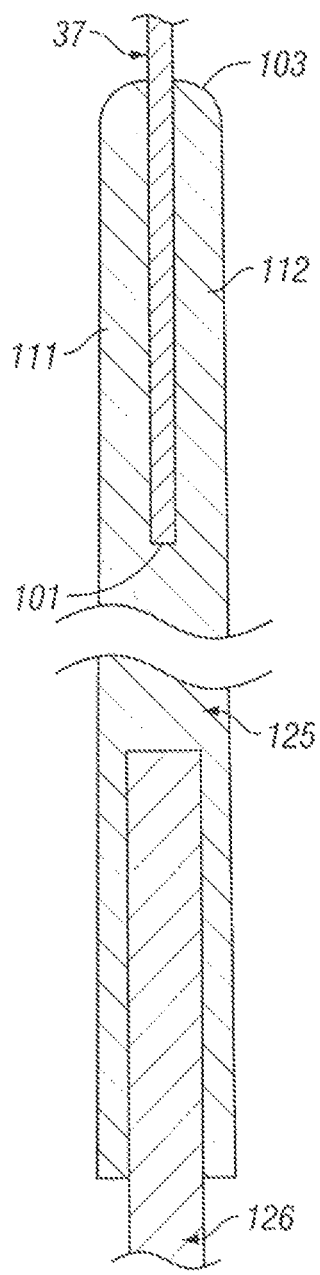
FIG. 77 is a cross-sectional side view similar to FIG. 74 showing a junction between a cap-like portion and a coupling portion but of an alternate configuration for coupling of the cap-like portion and the coupling portion with an intermediate portion.

Reference is made to FIG. 77 which illustrates a cross-sectional view similar to FIG. 74, however, showing the coupling portion 38 as comprising an inner tubular section 125 and an outer tubular section 126. The outer tubular section 126 is preferably to be resilient. The inner tubular section 125 is selected to have advantageous properties for fixedly securing the inner tubular section 125 to both the cap-like portion 37 preferably consisting of a metal sheet and to the outer tubular section 126. The inner tubular section 125 need not be resilient, however, may be resilient with a resiliency less than the resiliency of the outer tubular section 126. The inner tubular section 125 may preferably be provided to overlie the condyle 15 proximate the outer edge 101 of the cap-like portion 37 at locations where there is not a need for any substantial resiliency in order for the prosthesis 30 to be applied over the condyle 15.

The embodiments shown in cross-section of FIGS. 74 and 77 provide for mechanical securement of the metal sheet of the cap-like portion 37 to the coupling portion 38 as by material being received, for example, within the openings 54 as seen in FIG. 74 or inwardly from the axially inwardly directed shoulders 124 of the fingers 123 in FIG. 77. Such mechanical securement is not necessary. For example, in the embodiment of FIG. 74, the holes 54 may be eliminated and mere bonding of the engaged surfaces of the coupling portion 38 with surfaces of the cap-like portion 37 can be adequate.

In the embodiment of FIGS. 74 and 77, the coupling portion 38 has both the inner layer 111 and the outer layer 112. As a first alternative arrangement, the inner layer 111 may be eliminated such that merely the outer layer 112 is provided preferably with the inner surface 32 of the coupling portion 38 being coplanar with the inner surface 113 of the cap-like portion 37 at their juncture at the outer edge 101 of the cap-like portion 37. As a second alternative arrangement, the outer layer 111 may be eliminated such that merely the inner layer 111 is provided in which case the outer surface 114 of the coupling portion 38 may be coplanar with the outer surface 34 of the cap-like portion 37 at their juncture at the outer edge 101 of the cap-like portion 37.

The inherent shape and size of the coupling portion 38 is be selected so as to provide for advantageous engagement between the coupling portion 38 and the neck 42. For example, as seen in FIG. 64, the entirety of the coupling portion 38 may be shaped and sized so that its interior surface is an exact replication of the outer surface of the neck 42 and to provide a very close fit. Alternatively, the coupling portion 38 may be provided over its entirety or portions to provide a looser fit and, for example, to be circumferentially marginally greater than the circumference of the neck 42 at any portion. As a further alternative, the coupling portion 38 may over its entirety or selected portions be selected so as to have a shape and size corresponding to the shape and size of the neck 42 but marginally smaller in circumference such that, for example, when the coupling portion 38 is applied over the neck 42, the correspondence in shape will provide for relative axial and circumferential location, however, the resiliency, preferably at least circumferential resiliency of the coupling portion 38 will tend to contract the coupling portion 38 circumferentially about the neck 42.

Figure 79:
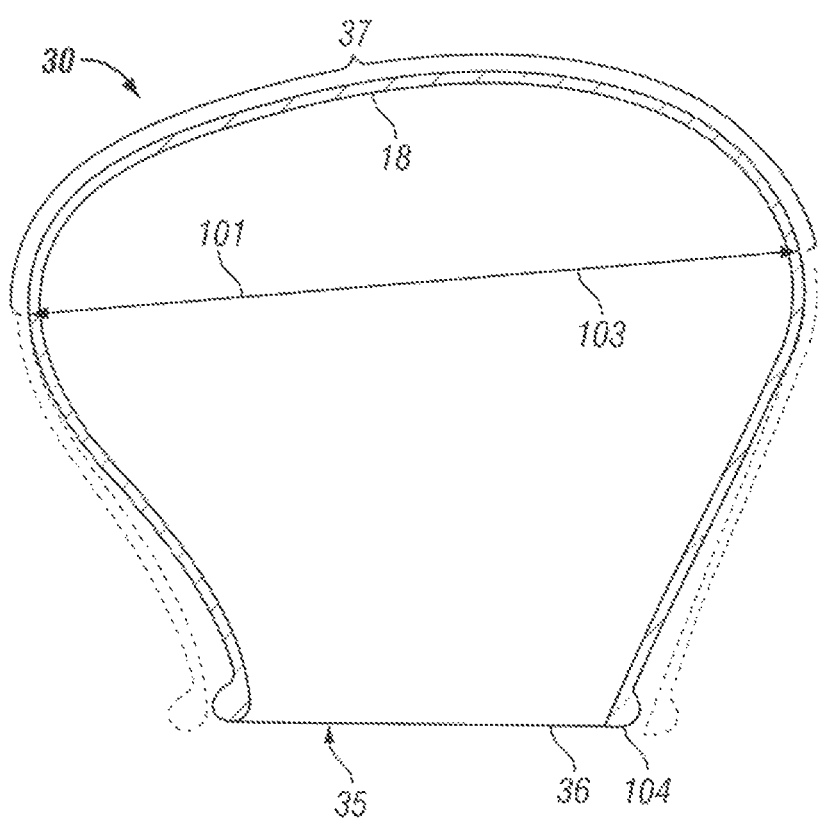
FIG. 79 is a cross-sectional view showing in solid lines a twentieth embodiment of a prosthesis in accordance with the present invention in an unbiased collapsed configuration.

An alternate embodiment of a resilient prosthesis 30 in accordance with a twentieth embodiment of the invention is illustrated in FIG. 79 in solid lines as showing its inherent shape and size and in broken lines as showing the closed shape that the prosthesis adopts when applied over the first bone member. The coupling portion 38 of FIG. 79 is resilient and has an inherent bias to assume the inherent shape when displaced from the inherent shape has as an inherent. The inherent shape has a circumference less than the closed shape. The coupling portion 38 has a shape and size corresponding to the shape and size of the neck 42 but marginally smaller in circumference such that, for example, when the coupling portion 38 is applied over the neck 42, the correspondence in shape will provide for relative axial and circumferential location, however, the resiliency, preferably at least circumferential resiliency of the coupling portion 38 will tend to contract the coupling portion 38 circumferentially about the neck 42. When in the expanded configuration, as seen in broken lines in FIG. 79, the inherent bias of the coupling portion 38 biases the coupling portion 38 from the expanded condition shown in broken lines in FIG. 79 toward the unbiased contracted configuration shown in solid lines in FIG. 79 and, thus, with the prosthesis 30 disposed about the condyle 15 in a manner as in FIG. 65, the coupling portion 38 under its inherent bias engages about the neck 42 adopting a circumference of a size and shape corresponding to the circumference of the neck 42.

To achieve the particular properties desired for the coupling portion 38 as, for example, such that it will be resilient and may be expanded circumferentially against its inherent bias and contract circumferentially about the neck 42, the coupling portion 38 may be made from known polymers, plastics and composites of the same by suitable selection from known materials by persons skilled in the art by simple experimentation.

The prosthesis 30 of FIGS. 64 to 77 may be manufactured by many different processes. Preferably, the cap-like portion may 37 be formed separately from a sheet of metal to have a desired shape. After making the cap-like portion 37, the coupling portion 38 may be secured to the cap-like portion 37. As one example, the coupling portion 38 may be made in situ on the cap-like portion 38 by a 3-dimensional printing process to deposit polymers and/or plastic material in a tubular shape starting with depositation about a peripheral section of the cap-like portion 37 proximate its outer edge 101. The composition of the materials deposited may be varied as the depositation proceeds as with a first composition suited to strongly bond with or engage the metal sheet and progressing into a different second more resilient composition towards the outer edge 36. As another example, the cap-like portion 37 may be placed within a mold for the coupling portion 38 and the coupling portion 38 formed within the mold in engagement with the cap-like portion 37. As yet another example, the coupling portion 38 may be formed within a mold as a separate element and then bonded as with suitable adhesives to the cap-like portion 38.

The manner of manufacture of the coupling portion 38 can be a factor in providing the coupling portion as a composite of materials, for example, to include a helical matrix of fibers forming an expandable and contractible open tubular structure to be impregnated with a resilient polymer or plastic material.

The nature of the plastic and/or polymer materials forming the coupling portion 38 can facilitate the coupling portion 38 serving an eluting device for elution of advantageous agents such as medications, therapeutics, pharmaceuticals, biologicals and bio-active substances into the joint including, for example, lubricants, anti-inflammatory, anti-microbials, antibacterials, anti-fungicides, growth promoting factors, healing factors, and analgesics. The incorporation of such agents in the plastics and/or polymers forming the coupling portion 38 may be as by impregnation. However, the agents may be provided merely in selected segments of the coupling portion 38 where the agents will not degrade performance of the coupling portion 38 as, for example, in the inner tubular section 125 of the coupling portion 38.

In the embodiment of FIGS. 64 to 77, preferably, the metal sheet member forming the cap-like portion 37 has a thickness between its inner surface and its outer surface not greater than 0.01 inches where the sheet member is to overlie the contiguous bony surfaces on the condyle 15 that are to be in contact with another bone during normal movement of the joint. However, since the junction between the cap-like portion 37 and the coupling portion 38 overlies the non-contiguous surface 19 of the condyle 15 which non-contiguous surface 19 is not normally in contact with a second bone member during movement of the joint, the junction between the cap-like portion 37 and the coupling portion 38 and the coupling portion 38 adjacent to and remote from this junction may have a thickness greater than the thickness of the cap-like portion 37. The thickness of the junction between the cap-like portion 37 and the coupling portion 38 can be selected so as to provide adequate strength to maintain the integrity of the coupling of the cap-like portion 37 and the coupling portion 38 under stresses to be expected to be accommodated with the prosthesis 30 in the joint during normal operation of the joint. The coupling portion 38 and particularly the junction of the coupling portion 38 and the cap-like portion 37 may have thicknesses greater than that of the cap-like portion 37, for example, 0.02 inches, or substantially greater, for example, in a range of 0.02 to 0.10 inches, or less than 0.1 inches, and greater.

As with all the Figures in this application, FIGS. 63 to 79 are not to scale.

The tubular coupling portion 38 in some of the preferred embodiments is resilient and capable of being expanded circumferentially to permit the bulbous end 40 to pass therethrough and then to contract circumferentially about the neck 42 so as to assume a circumference equal to that of the neck 42. It is not, however, necessary that tubular coupling portion 38 be resilient. Since the prosthesis 30 needs to be applied to the condyle 15 but once, it is merely necessary that the coupling portion 38 be capable of having a circumferential extent that permits the end 40 to pass therethrough a single time and it is merely necessary that the tubular coupling portion 38 be contracted circumferentially onto the neck 42 once. As one arrangement, the coupling portion 38 may be formed as a tubular member of either an initial size to permit the end 40 to pass therethrough or with a resiliency permitting the bulbous end 40 to pass therethrough. After the end 42 has been passed through the coupling portion 38, the coupling portion 38 needs to be circumferentially reduced onto the neck 42. The reduction in the circumferential extent of the tubular coupling portion 38 may be accomplished by various means other than those relying merely on inherent resiliency. For example, the polymer or plastic forming the coupling portion 38 may be selected such that it shrinks by the application of radiation, heat or a chemical agent. Preferably, by the localized application of radiation such as light, preferably ultraviolet light, to the coupling portion 38, the coupling portion 38 can have its circumference reduced to adopt a shape and size corresponding to the shape and size of the neck 42 without the coupling portion 38 necessarily having to be resilient.

The embodiment of FIGS. 64 to 77 has been described preferably utilizing as the cap-like portion 37 a thin sheet of metal. The sheet of metal preferably is a continuous sheet of metal with the inner surface and the outer surface which are to engage the articular surfaces of adjacent bones spaced by the prosthesis to each be a continuous surface without any openings or pores therethrough other than at the subatomic level. Such a sheet of metal preferably has low friction to permit relative sliding of both the both spaced bone relative the prosthesis 30 and with the cap-like portion 37 to move marginally relative to the bulbous end 40. In accordance with the embodiments of FIGS. 64 to 77, insofar as the coupling portion 38 is resilient and/or flexible, then resiliency of the coupling portion 38 can accommodate marginal relative movement of the cap-like portion 37 on the bulbous end 40 even though sections of the coupling member 38, may engage the neck 42 substantially against relative movement. For example, should the annular ring 104 engage about the neck 42 in a manner substantially against relative movement, then the resiliency of the coupling portion 38 between the annular ring 104 and the cap-like portion 37 can permit marginal relative movement on the cap-like portion 37 on the end 40.

Figure 78:
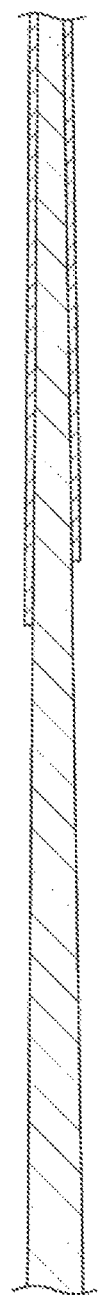
FIG. 78 is a cross-sectional side view similar to FIGS. 74 and 77 showing a junction between a cap-like portion and a coupling portion but of another alternate configuration with the cap-like portion and the coupling portion formed as an integral member.

Reference is made to FIG. 78 which illustrates a cross-sectional view similar to FIG. 74, however, showing the prosthesis 30 as having a continuous polymer member 200 which extends from the cap-like portion 37 to the coupling portion 38 and preferably throughout the coupling portion 38. Over the cap-like portion 37 the polymer member 200 carries an inner layer 201 of metal and an outer layer 202 of metal, preferably applied to the member 200 as by vapor deposition. The continuous polymer member 200 preferably is relatively rigid and not resilient over the cap-like portion 37 as to aid retention of the metal layers 201 and 202. The continuous polymer member 200 may preferably be resilient over the coupling portion 38.

The materials from which the coupling portion 38 is made may be selected such that after the prosthesis 30 may be applied to the first bone member and placed into the joint the coupling portion will come to set in the closed position so that the coupling portion will have an inherent memory to maintain the closed shape. For example, setting of the coupling portion 38 can arise by and be subject to conditions which arise within the joint including, for example, constant conditions of temperature, interaction with fluids in the joint, the elution from the coupling member of components of the materials forming the coupling member that provide resiliency and the elution from the coupling member of components that may be active medical incipients and the like that are desired to be eluded into the joint. Additionally, insofar as the coupling portion 38 may, to some extent, rely on its inherent resiliency to adopt the closed position, once in the closed position, the coupling portion 38 may be set in its closed shape by the application, for example, of radiation such as light or ultraviolet light, heat or chemical reagents, to effectively reduce the resiliency of the coupling portion and preferably set the coupling portion to substantially maintain the closed shape.

In respect of a coupling portion which may be shrunk from the open position to the closed position, preferably, after the coupling portion reaches its closed shape, the coupling portion may be set in the closed state.

The prosthesis 30 of the embodiments illustrated in FIGS. 63 to 79 may be applied to the first bone member in accordance with a method of use in accordance with the present invention. The method comprises longitudinally sliding the prosthesis 30 over the end 40 of the first bone member through the tubular portion in the open position and its outer opening to locate the end of the first bone member within the cap-like portion and the coupling portion about the neck of the first bone member and, subsequently, changing the tubular portion from the open position to the closed position. In a first version of the method, the method includes locating the cap-like portion relative the end of the first bone member so that the shape and size of the inner surface of the cap-like portion and the matching shape and size of the outer surface of the end of the first bone member complementary coincide. Subsequent to so locating the cap-like portion on the end, the method then carries out the step of changing the tubular portion from the open position to the closed position. In this manner, the first version of the method relies on the inter action of the cap-like portion and the end of the first bone member to provide appropriate juxtaposition of the prosthesis on the first bone member and, the tubular portion is then secured about the neck in the closed position. Once the tubular portion is secured about the neck in the closed position, the method involves preferably setting the material comprising the coupling position in the closed position so the coupling position has an inherent memory to maintain the closed shape.

In a second version of the method, the coupling portion is resilient and has an inherent bias to assume an inherent shape when displaced from the inherent shape and the coupling portion is changeable from the open position to the closed position due to the resiliency of the coupling portion. The method involves the step of juxtaposition of the prosthesis on the first bone member by locating the coupling portion relative the neck so that the closed shape and size of the coupling portion and the matching shape and size of the outer surface of the neck of the first bone member complementary coincide. Using the second method, the engagement of the coupling portion on the neck relatively juxtapositions the prosthesis on the first bone member and will thereby locate the cap-like portion in an appropriate location relative the end of the first bone member. Once the tubular portion is secured about the neck in the closed position, the method involves preferably setting the material comprising the coupling position in the closed position so the coupling position has an inherent memory to maintain the closed shape.

The prosthesis 30 may preferably carry over the coupling portion location indicia so as to assist in correctly locating the prosthesis on the first bone member 52 in a desired position. Referring to FIG. 64, the prosthesis 30 is shown to carry on the coupling portion 38 an arrow indicating, for example, a position on the prosthesis that is to align with the position on the bone. In the case of FIG. 64, as seen in FIG. 65, the arrow is indicated to align with a ridge on the bone. Suitable other indicias such as these arrows which may be embossed in the exterior surface of the coupling member may be provided at front and back, side and rear locations as may be desired to assist in orienting the prosthesis 30 on the first bone member. As well, the locating indicia, such as 210, may be provided in or on the annular ring 104.

While the invention has been described with reference to preferred embodiments, many modifications and variations of the invention will now occur to persons skilled in the art. For a definition of the invention, reference is made to the following claims.

I claim:

1. A method of use of a spacing prosthesis for enveloping an end and a neck of a first bone member in a mammalian joint and spacing the end of the first bone member from a second bone member normally in contact with the end of first bone member within the joint, the outer surface of the first bone member over the end of the first bone member comprising a contiguous bony outer surface which engages with a contiguous bony outer surface of the second bone member in normal movement of the joint, the neck of the first bone member comprising a non-contiguous surface of the first bone member which non-contiguous surface is not normally in contact with the second bone member during movement of the joint, the prosthesis comprising a thin member having an inner surface and an outer surface, the thin member comprising an inner closed cap portion and an outer tubular coupling portion extending outwardly from the cap portion, the cap portion having an inner closed end and extending outwardly to a circumferentially extending peripheral cap opening, the coupling portion extending outwardly from a circumferentially extending inner opening at a peripheral inner end of the coupling portion to a circumferentially extending peripheral outer opening at a peripheral outer end of the coupling portion, the cap opening of the cap portion coupled to the inner opening of the coupling portion whereby the inner surface of the sheet member over the cap portion and the coupling portion defines a bone receiving cavity from the inner closed end of the cap portion outwardly through the cap portion to the coupling portion and through the coupling portion to the outer opening, the sheet member over the cap portion consisting of a sheet-like substrate carrying as each of the inner surface and the outer surface a layer of metal, the inner surface over the cap portion conforming in shape and size to an outer surface of the end of the first bone member and permitting the cap member to be longitudinally slidable over the end of first bone member through the outer opening to receiving the first bone member within the first bone receiving cavity within the cap portion, the coupling portion being changeable from an open position to a closed position, in the open position the coupling portion longitudinally slidable over the end of the first bone member through the coupling portion and its outer opening to locate the end of the first bone member within the cap portion and the coupling portion about the neck of the first bone member, the coupling portion changeable from the open position to the closed position in which closed position the inner surface over the coupling portion adopts a closed shape and size that conforms in shape and size to the shape and size of the outer surface of the neck of the first bone member to resist relative movement of the prosthesis relative the first bone member, the method comprising:

longitudinally sliding the prosthesis over the end of the first bone member through the tubular portion in the open position and its outer opening to locate the end of the first bone member within the cap portion and the coupling portion about the neck of the first bone member and, subsequently, changing the coupling portion from the open position to the closed position.

2. A method as claimed in claim 1 including locating the cap portion relative the end of the first bone member so that the shape and size of the inner surface of the cap portion and the matching shape and size of the outer surface of the end of the first bone member complementarily coincide.

3. A method as claimed in claim 2 including after the step of changing the tubular portion from the open position to the closed position, setting the material comprising the coupling portion in the closed position so that the coupling portion has an inherent memory to maintain the closed shape.

4. A method as claimed in claim 1 wherein the coupling portion is resilient and has an inherent bias to assume an inherent shape when displaced from the inherent shape, the coupling portion being changeable from the open position to the closed position due to the resiliency of the coupling portion, the inherent shape corresponding to the closed shape, the method including locating the coupling portion relative the neck so that closed shape of the coupling portion and the matching shape and size of the outer surface of the neck of the first bone member complementarily coincide.

5. A method as claimed in claim 1 wherein the sheet substrate having a thickness between the inner surface and the outer surface not greater than 0.01 inches, the sheet substrate is selected from the group consisting of:

a. member consisting of metal, and b. a member comprising a composite of plastic or polymer materials with metal providing the inner surface and the outer surface as metal, the thin member over the coupling portion comprising plastic or polymer materials.

6. A method as claimed in claim 5 wherein the sheet substrate consisting of metal.

* * * * *